United States Patent
Ho et al.

(10) Patent No.: US 9,527,926 B2
(45) Date of Patent: Dec. 27, 2016

(54) HETERODIMERIC PROTEINS AND METHODS FOR PRODUCING AND PURIFYING THEM

(75) Inventors: Wei-Hsien Ho, Belmont, CA (US); Jaume Pons, San Francisco, CA (US); Arvind Rajpal, San Francisco, CA (US); Pavel Strop, San Mateo, CA (US)

(73) Assignee: RINAT NEUROSCIENCE CORP., South San Francisco, CA (US)

( * ) Notice: Subject to any disclaimer, the term of this patent is extended or adjusted under 35 U.S.C. 154(b) by 218 days.

(21) Appl. No.: 13/697,683

(22) PCT Filed: May 13, 2011

(86) PCT No.: PCT/US2011/036419
§ 371 (c)(1),
(2), (4) Date: Jan. 17, 2013

(87) PCT Pub. No.: WO2011/143545
PCT Pub. Date: Nov. 17, 2011

(65) Prior Publication Data
US 2013/0115208 A1     May 9, 2013

Related U.S. Application Data

(60) Provisional application No. 61/345,047, filed on May 14, 2010, provisional application No. 61/485,097, filed on May 11, 2011.

(51) Int. Cl.
C07K 16/46 (2006.01)
C07K 16/28 (2006.01)
C07K 16/30 (2006.01)
A61K 39/00 (2006.01)

(52) U.S. Cl.
CPC ......... *C07K 16/468* (2013.01); *C07K 16/2809* (2013.01); *C07K 16/2887* (2013.01); *C07K 16/30* (2013.01); *C07K 16/46* (2013.01); *A61K 2039/505* (2013.01); *C07K 2317/31* (2013.01); *C07K 2317/526* (2013.01); *C07K 2317/53* (2013.01); *C07K 2317/73* (2013.01); *C07K 2317/92* (2013.01)

(58) Field of Classification Search
CPC .............. C07K 16/00–16/468; C07K 2316/52; C07K 2317/30; C07K 2317/31; C07K 2317/526; C07K 2317/53; C07K 2317/56; C07K 2317/60–2317/64; C07K 2317/94
See application file for complete search history.

(56) References Cited

U.S. PATENT DOCUMENTS

| 5,807,706 | A | 9/1998 | Carter et al. |
| 7,695,936 | B2 | 4/2010 | Carter et al. |
| 2010/0015133 | A1 | 1/2010 | Igawa et al. |
| 2010/0105874 | A1 | 4/2010 | Schuurman et al. |

FOREIGN PATENT DOCUMENTS

| WO | WO2008/119353 A1 * | 10/2008 |
| WO | WO 2009/006520 | 1/2009 |
| WO | WO 2009/089004 | 7/2009 |
| WO | WO2009/089004 A1 * | 7/2009 |
| WO | WO2011/131746 A2 * | 10/2011 |
| WO | WO 2011/1131746 | 10/2011 |

OTHER PUBLICATIONS

Kleinschmidt et al., J. Mol. Biol. 2003; 327:445-452.*
Saphire et al., J. Mol. Biol., 2002; 319:9-18.*
International Search Report dated Oct. 14, 2011 for PCT application No. PCT/US2011/036419, published on Nov. 17, 2011 as WO2011143545.
Gunasekaran, K., et. al., "Enhancing Antibody Fc Heterodimer Formation through Electrostatic Steering Effects," 2010, The Journal of Biological Chemistry, vol. 285:25: 19637-19646.
Written Opinion dated Nov. 20, 2012 for PCT application No. PCT/IB2011/036419, published on Nov. 17, 2011 as WO2011143545.

* cited by examiner

*Primary Examiner* — Jessica H Roark
(74) *Attorney, Agent, or Firm* — Jenny J. Yeh; Deborah A. Martin

(57) ABSTRACT

The present invention relates to engineered heteromultimeric proteins, and more specifically, to methods for producing and purifying heterodimeric proteins, such as bispecific antibodies and other heterodimeric proteins comprising immunoglobulin-like hinge sequences. Methods for producing and purifying such engineered heterodimeric proteins and their use in diagnostics and therapeutics are also provided.

10 Claims, 36 Drawing Sheets

FIG. 2

Human IgG2AA Fc region sequence (SEQ ID NO: 1):

GCCTCCACCAAGGGCCCATCTGTCTTCCCACTGGCCCCTTGCTCCCGAGAGCACCTCCGAGAGCACAGCCGCCCTGGGCTGCCTGGTC

AAGGACTACTTCCCAGAGCCTGTGACCGTGTCCTGGAACTCTGGAGCCCTGACCAGCGGCGTGCACACCTTCCCAGCTGTCCTGCAG

TCCTCAGGTCTCTACTCCCTCAGCAGCGTGGTGACCGTGCCATCAGCAACTTCGGCACCCAGACCTACACCTGCAACGTAGATCAC

AAGCCAAGCAACACCAAGGTCGACAAGACCGTGGAGAGAAAGTGTTGTGTGGAGTGTCCACCTTGTCCAGCCCCTCCAGTGGCC

GGACCATCCGTGTTCCTGTTCCCTCCAAAGCCAAAGGACACCCTGATGATCTCCAGAACCCCAGAGGTGACGTGTGGTGGTGGAC

GTGTCCCACGAGGACCCAGAGGTGCAGTTCAACTGGTATGTGGACGGAGTGGAGGTGCACAACGCCAAGACCAAGCCAAGAGAGG

AGCAGTTCAACTCCACCTTCAGAGTGGTGAGCGTGCTGACCGTGGTGCACCAGGACTGGCTGAACGGAAAGGAGTATAAGTGTAAG

GTGTCCAACAAGGGACTGCCATCCAGAGGAGATGACCAAGAACCAGGTGTCCCTGACCTGTCTGGTGAAGGATTCTATCCATCGCCGTG

TGCCCCCATCCAGAGAGGAGATGACCAAGAACCAGCAGCAGAACAACTATAAGACCACCCCTCCAATGCTGGACTCCGACGGATCCTTCCTGTATTCC

GAGTGGGAGTCCAACGGACAGCCAGAGAATGGCAGCAGGAAACGTGTTCTCTTGTTCCGTGATGCACGAGGCCCTGCACAACCACTATAC

AAGCTGACCGTGGACAAGTCCAGATGGCAGCAGGAAACGTGTTCTCTTGTTCCGTGATGCACGAGGCCCTGCACAACCACTATAC

CCAGAAGAGCCTGTCCCTGTCTCCGGGTAAATAGGCGGCCGC

FIG. 4

Human IgG1 wild-type Fc region sequence (SEQ ID NO: 11)

```
GCGTCCACCAAGGGCCCATCGGTCTTCCCCCTGGCACCCTCCTCCAAGAG
CACCTCTGGGGGCACAGCGGCCCTGGGCTGCCTGGTCAAGGACTACTTCC
CCGAACCGGTGACGGTGTCGTGGAACTCAGGCGCCCTGACCAGCGGCGT
GCACACCTTCCCGGCTGTCCTACAGTCCTCAGGACTCTACTCCCTCAGCAG
CGTGGTGACCGTGCCCTCCAGCAGCTTGGGCACCCAGACCTACATCTGCA
ACGTGAATCACAAGCCCAGCAACACCAAGGTCGACAAGAAAGTTGAGCCC
AAATCTTGTGACAAAACTCACACATGCCCACCGTGCCCAGCACCTGAACTC
CTGGGGGGACCGTCAGTCTTCCTCTTCCCCCCAAAACCCAAGGACACCCT
CATGATCTCCCGGACCCCTGAGGTCACATGCGTGGTGGTGGACGTGAGCC
ACGAAGACCCTGAGGTCAAGTTCAACTGGTACGTGGACGGCGTGGAGGTG
CATAATGCCAAGACAAAGCCGCGGGAGGAGCAGTACAACAGCACGTACCG
TGTGGTCAGCGTCCTCACCGTCCTGCACCAGGACTGGCTGAATGGCAAGG
AGTACAAGTGCAAGGTCTCCAACAAAGCCCTCCCAGCCCCCATCGAGAAA
CCATCTCCAAAGCCAAAGGGCAGCCCCGAGAACCACAGGTGTACACCCTG
CCCCCATCCCGGGATGAGCTGACCAAGAACCAGGTCAGCCTGACCTGCCT
GGTCAAAGGCTTCTATCCCAGCGACATCGCCGTGGAGTGGGAGAGCAATG
GGCAGCCGGAGAACAACTACAAGACCACGCCTCCCGTGCTGGACTCCGAC
GGCTCCTTCTTCCTCTACAGCAAGCTCACCGTGGACAAGAGCAGGTGGCA
GCAGGGGAACGTCTTCTCATGCTCCGTGATGCATGAGGCTCTGCACAACC
ACTACACGCAGAAGAGCCTCTCCCTGTCCCCGGGTAAATAGAGCGGCCGC
```

FIG. 5

Human IgG4 wild-type Fc region sequence (SEQ ID NO: 12)

```
GCGTCCACCAAGGGCCCATCGGTCTTCCCCCTGGCACCCTCCTCCAAGAG
CACCTCTGGGGGCACAGCGGCCCTGGGCTGCCTGGTCAAGGACTACTTCC
CCGAACCGGTGACGGTGTCGTGGAACTCAGGCGCCCTGACCAGCGGCGT
GCACACCTTCCCGGCTGTCCTACAGTCCTCAGGACTCTACTCCCTCAGCAG
CGTGGTGACCGTGCCCTCCAGCAGCTTGGGCACCCAGACCTACATCTGCA
ACGTGAATCACAAGCCCAGCAACACCAAGGTCGACAAGAAAGTTGAGCCC
AAATCTTGTGACAAAACTCACACATGCCCACCGTGCCCAGCACCTGAACTC
CTGGGGGACCGTCAGTCTTCCTCTTCCCCCCAAAACCCAAGGACACCCT
CATGATCTCCCGGACCCCTGAGGTCACATGCGTGGTGGTGGACGTGAGCC
ACGAAGACCCTGAGGTCAAGTTCAACTGGTACGTGGACGGCGTGGAGGTG
CATAATGCCAAGACAAAGCCGCGGGAGGAGCAGTACAACAGCACGTACCG
TGTGGTCAGCGTCCTCACCGTCCTGCACCAGGACTGGCTGAATGGCAAGG
AGTACAAGTGCAAGGTCTCCAACAAAGGCCTCCCAGCCCCCATCGAGAAA
ACCATCTCCAAAGCCAAAGGGCAGCCCCGAGAACCACAGGTGTACACCCT
GCCCCCATCCCGGGATGAGCTGACCAAGAACCAGGTCAGCCTGACCTGCC
TGGTCAAAGGCTTCTATCCCAGCGACATCGCCGTGGAGTGGGAGAGCAAT
GGGCAGCCGGAGAACAACTACAAGACCACGCCTCCCGTGCTGGACTCCG
ACGGCTCCTTCTTCCTCTACAGCAAGCTCACCGTGGACAAGAGCAGGTGG
CAGCAGGGGAACGTCTTCTCATGCTCCGTGATGCATGAGGCTCTGCACAA
CCACTACACGCAGAAGAGCCTCTCCCTGTCCCCGGGTAAATAGGGCCGC
```

FIG. 6A

Alignment of IgG Hinge region

```
hIgG4  ESKYGPP---CPSCP
                    228 hIgG2  ERKCCVE---CPPCP
           223 225    228 hIgG1  EPKSCDKTHTCPPCP
          221         228
```

FIG. 6B

IgG4 mutants (hinge mutation at S228)

| group | clones | hinge mutation | group | clones | hinge mutation |
|---|---|---|---|---|---|
| A | 3.9A | K | B | 3.3A | D |
|   | 3.11A | R |   | 3.2A | E |

IgG4 mutants (hinge mutation at D221 and P228 or at P228 only)

| group | clone | hinge mutation | group | clone | hinge mutation |
|---|---|---|---|---|---|
| A | hFc1.RR.K409R | R R | B | 3.3A | E E |
|   | hFc1.R.K409R |   R |   | 3.2A |   E |

IgG2 mutants (hinge mutations at C223, E225, and P228)

| group | clones | HM* | group | clones | HM* | group | clones | HM* | group | clones | HM* |
|---|---|---|---|---|---|---|---|---|---|---|---|
| AI | 2.1F | D E R | AII | 2.11F | D E R | BI | 1.6B | R K E | BII | 1.1F | K K D |
|  | 2.2F | D E K |  | 2.11G | D E K |  | 1.8B | R K D |  | 1.5F | R K E |
|  | 2.7F | E E R |  | 2.11H | E E R |  | 1.9A | K K D |  | 1.7G | K R E |
|  | 2.2G | E E D |  | 2.2H | E E R |  | 1.9B | R R E |  | 1.9F | K R D |
|  | 2.3G | D E E |  | 2.3H | E E E |  | 1.11B | K R E |  | 1.9G | R R D |
|  | 2.10G | E E E |  | 2.5H | D E E |  | 1.12B | R R D |  | 1.10F | K R E |
|  | 2.1E | E E K |  | 2.2C | D E E |  | 1.3D | R R R |  | 1.7H | R R R |
|  | 2.2D | E R D |  | 2.9C | E R E |  | 1.6C | K K R |  | 1.10H | K R R |
|  | 2.4E | D R E |  | 2.10B | D R E |  | 1.7C | K R R |  | 1.11H | R K R |
|  | 2.5E | D K D |  |  |  |  | 1.8C | R K R |  | 1.12H | R K R |
|  | 2.9E | E R E |  |  |  |  | 1.8D | R K K |  | 2.1A | K K K |
|  | 2.10D | E K D |  |  |  |  | 1.9C | R R K |  | 2.3A | K R K |
|  | 2.11D | E K E |  |  |  |  | 1.10D | K R K |  | 2.8A | R R K |
|  | 2.121D | D R E |  |  |  |  | 1.7E | R E K |  | 2.9A | R E R |
|  |  |  |  |  |  |  | 1.8E | K E K |  | 2.10A | K E R |
|  |  |  |  |  |  |  | 1.9E | K E R |  |  |  |
|  |  |  |  |  |  |  | 1.12F | R E R |  |  |  |

*HM=hinge mutation

FIG. 6C

| | GroupA clones | hinge mutation | GroupB clones | hinge mutation |
|---|---|---|---|---|
| A | 3.11A (hIgG4.R.wt.Ab1.Ab1) | R | 3.2A (hIgG4.E.wt.Ab1.Ab1) | E |
| B | 3.9A (hIgG4.K.wt.Ab1.Ab1) | K | 3.2A (hIgG4.E.wt.Ab1.Ab1) | E |
| C | 3.11A (hIgG4.R.wt.Ab1.Ab1) | R | 3.3A (hIgG4.D.wt.Ab1.Ab1) | D |
| D | 3.9A (hIgG4.K.wt.Ab1.Ab1) | K | 3.3A (hIgG4.D.wt.Ab1.Ab1) | D |
| E | Ab1.wild-type hIgG4 | | | |

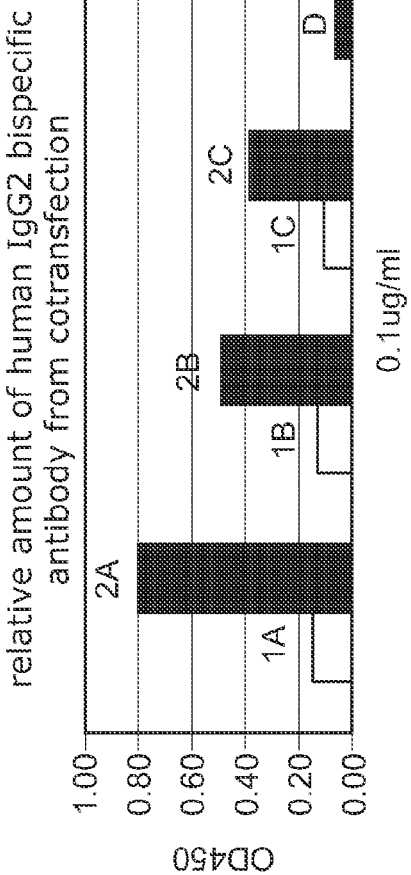

| | Group A clones | hinge mutation | GroupB clones | hinge mutation |
|---|---|---|---|---|
| 1A | 2.2F (hIgG2ΔA.DEK.wt.Ab1.Ab1) | D_E_K_ | 1.12B (hIgG2ΔA.RRD.wt.Ab1.Ab1) | R_R_D_ |
| 2A | 2.11G (hIgG2ΔA.DEK.K409R.Ab1.Ab1) | D_E_K_ | 1.9F (hIgG2ΔA.RRD.K409R.Ab1.Ab1) | R_R_D_ |
| 1B | 2.3G (hIgG2ΔA.DEE.wt.Ab1.Ab1) | D_E_E_ | 1.8B (hIgG2ΔA.RKR.wt.Ab1.Ab1) | R_K_R_ |
| 2B | 2.5H (hIgG2ΔA.DEE.K409R.Ab1.Ab1) | D_E_E_ | 1.11B (hIgG2ΔA.RKR.K409R.Ab1.Ab1) | R_K_R_ |
| 1C | 2.10D (hIgG2ΔA.ERE.wt.Ab1.Ab1) | E_R_E_ | 1.7E (hIgG2ΔA.REK.wt.Ab1.Ab1) | R_E_K_ |
| 2C | 2.2C (hIgG2ΔA.ERE.K409R.Ab1.Ab1) | E_R_E_ | 1.11H (hIgG2ΔA.REK.K409R.Ab1.Ab1) | R_E_K_ |
| D | Ab1.wild type hIgG2ΔA | | | |

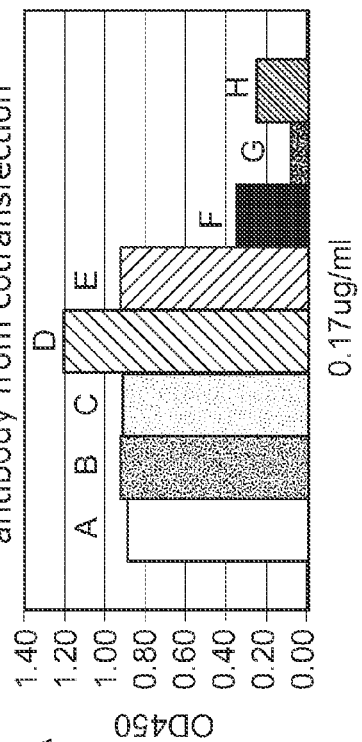

| | Group A clones | hinge mutations | Group B clones | hinge mutations |
|---|---|---|---|---|
| A | 2.11H (hIgG2ΔA.EER.K409R.Ab1.Ab1) | _E_E_R_ | 1.5F (hIgG2ΔA.RKE.K409R.Ab1.Ab1) | _R_K_E_ |
| B | 2.9C (hIgG2ΔA.DRE.K409R.Ab1.Ab1) | _D_R_E_ | 2.10A (hIgG2ΔA.KER.K409R.Ab1.Ab1) | _K_E_R_ |
| C | 2.11F (hIgG2ΔA.DER.K409R.Ab1.Ab1) | _D_E_R_ | 1.10F (hIgG2ΔA.RRE.K409R.Ab1.Ab1) | _R_R_E_ |
| D | 2.2H (hIgG2ΔA.EEE.K409R.Ab1.Ab1) | _E_E_E_ | 1.10H (hIgG2ΔA.RRR.K409R.Ab1.Ab1) | _R_R_R_ |
| E | 2.10B (hIgG2ΔA.EKE.K409R.Ab1.Ab1) | _E_K_E_ | 2.9A (hIgG2ΔA.RER.K409R.Ab1.Ab1) | _R_E_R_ |
| F | 2.5H (hIgG2ΔA.DEE.K409R.Ab1.Ab1) | _D_E_E_ | 1.11H (hIgG2ΔA.RKR.K409R.Ab1.Ab1) | _R_K_R_ |
| G | Ab1.wild type hIgG2ΔA | | | |
| H | Ab1.wild type hIgG4 | | | |

FIG. 10

"Glu" scanning in hIgG1, hIgG2, and hIgG4 CH3 domains

| | 341 | 342 | 343 | 344 | 345 | 346 | 347 | 348 | 349 | 350 | 351 | 352 | 353 | 354 | 355 | 356 | 357 | 358 | 359 | 360 | 361 | 362 | 363 | 364 | 365 | 366 | 367 | 368 | 369 | 370 | 371 | 372 | 373 | 374 | 375 | 376 | 377 | 378 | 379 | 380 |
|---|---|---|---|---|---|---|---|---|---|---|---|---|---|---|---|---|---|---|---|---|---|---|---|---|---|---|---|---|---|---|---|---|---|---|---|---|---|---|---|---|
| hIgG1 CH3 | G | Q | P | R | E | P | Q | V | Y | T | L | P | P | S | R | D | E | L | T | K | N | Q | V | S | L | T | C | L | V | K | G | F | Y | P | S | D | I | A | V | E |
| hIgG2ΔA CH3 | G | Q | P | R | E | P | Q | V | Y | T | L | P | P | S | R | E | E | M | T | K | N | Q | V | S | L | T | C | L | V | K | G | F | Y | P | S | D | I | A | V | E |
| hIgG4 CH3 | G | Q | P | R | E | P | Q | V | Y | T | L | P | P | S | Q | E | E | M | T | K | N | Q | V | S | L | T | C | L | V | K | G | F | Y | P | S | D | I | A | V | E |

Positions marked: 1, 2, 3, 4 (347-351); 5 (366); 6 (368); 7 (370)

| | 381 | 382 | 383 | 384 | 385 | 386 | 387 | 388 | 389 | 390 | 391 | 392 | 393 | 394 | 395 | 396 | 397 | 398 | 399 | 400 | 401 | 402 | 403 | 404 | 405 | 406 | 407 | 408 | 409 | 410 | 411 | 412 | 413 | 414 | 415 | 416 | 417 | 418 | 419 | 420 |
|---|---|---|---|---|---|---|---|---|---|---|---|---|---|---|---|---|---|---|---|---|---|---|---|---|---|---|---|---|---|---|---|---|---|---|---|---|---|---|---|---|
| hIgG1 CH3 | W | E | S | N | G | Q | P | E | N | N | Y | K | T | T | P | P | V | L | D | S | D | G | S | F | F | L | Y | S | K | L | T | V | D | K | S | R | W | Q | Q | G |
| hIgG2ΔA CH3 | W | E | S | N | G | Q | P | E | N | N | Y | K | T | T | P | P | M | L | D | S | D | G | S | F | F | L | Y | S | K | L | T | V | D | K | S | R | W | Q | Q | G |
| hIgG4 CH3 | W | E | S | N | G | Q | P | E | N | N | Y | K | T | T | P | P | V | L | D | S | D | G | S | F | F | L | Y | S | R | L | T | V | D | K | S | R | W | Q | E | G |

Positions marked: 8 (392); 9 (395); 10, 11 (397-398); 12, 13 (406-407); 14 (409)

| | 421 | 422 | 423 | 424 | 425 | 426 | 427 | 428 | 429 | 430 | 431 | 432 | 433 | 434 | 435 | 436 | 437 | 438 | 439 | 440 | 441 | 442 | 443 | 444 | 445 | 446 | 447 |
|---|---|---|---|---|---|---|---|---|---|---|---|---|---|---|---|---|---|---|---|---|---|---|---|---|---|---|---|
| hIgG1 CH3 | N | V | F | S | C | S | V | M | H | E | A | L | H | N | H | Y | T | Q | K | S | L | S | L | S | P | G | K |
| hIgG2ΔA CH3 | N | V | F | S | C | S | V | M | H | E | A | L | H | N | H | Y | T | Q | K | S | L | S | L | S | P | G | K |
| hIgG4 CH3 | N | V | F | S | C | S | V | M | H | E | A | L | H | N | H | Y | T | Q | K | S | L | S | L | S | L | G | K |

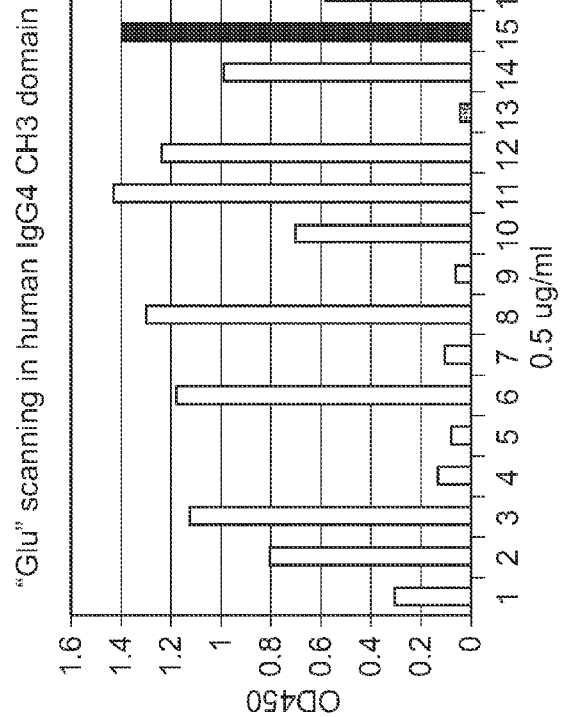

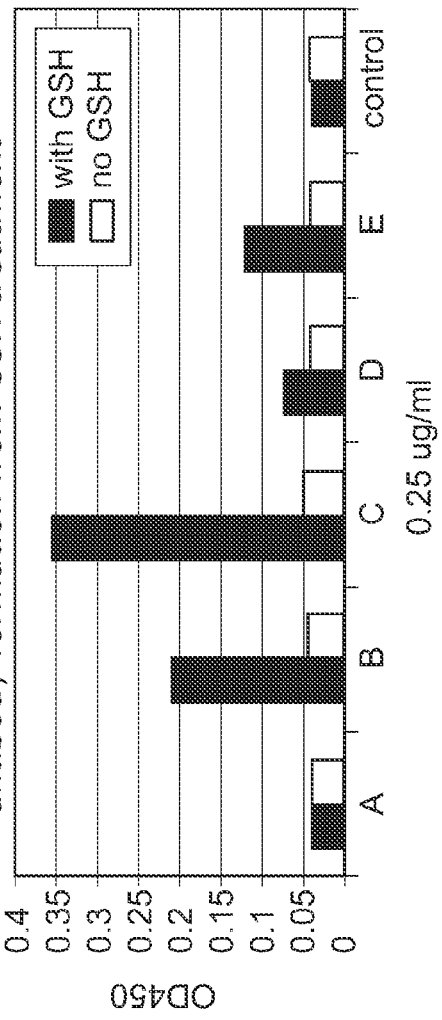

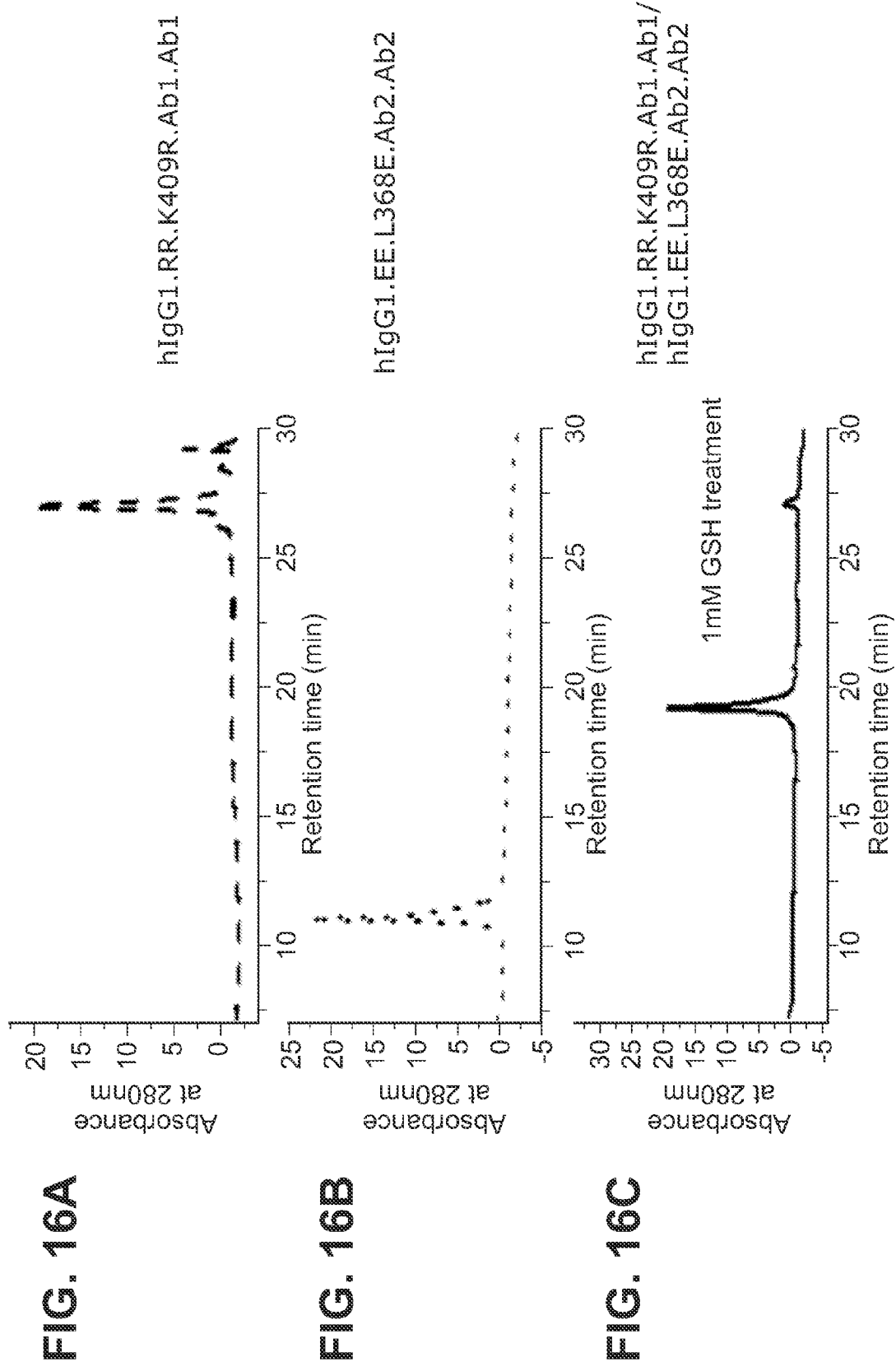
FIG. 16A  hIgG1.RR.K409R.Ab1.Ab1
FIG. 16B  hIgG1.EE.L368E.Ab2.Ab2
FIG. 16C  hIgG1.RR.K409R.Ab1.Ab1/hIgG1.EE.L368E.Ab2.Ab2 — 1mM GSH treatment

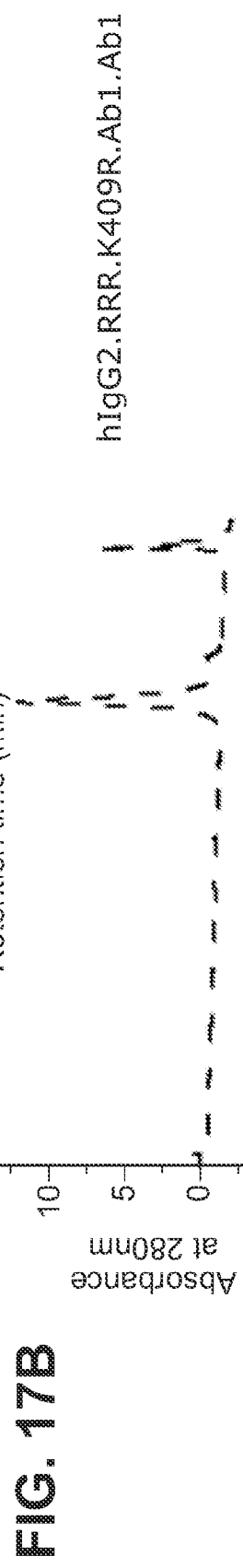
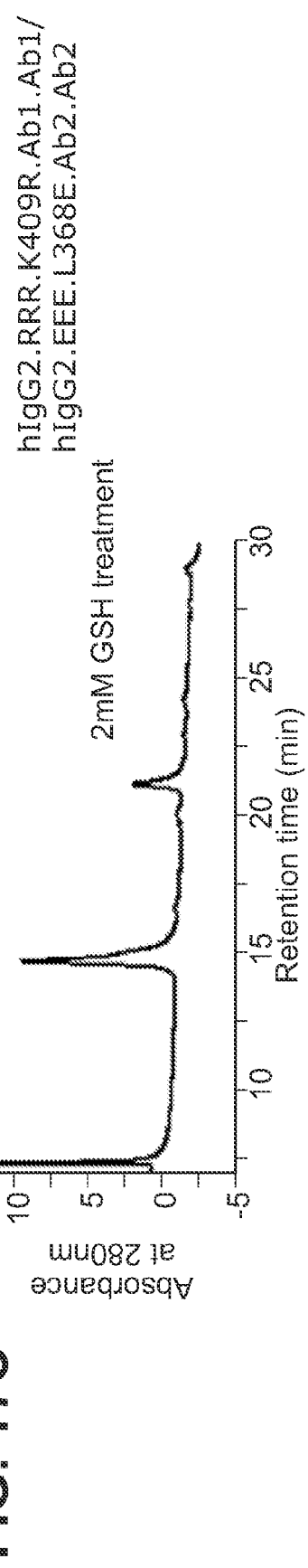
FIG. 17A
FIG. 17B
FIG. 17C

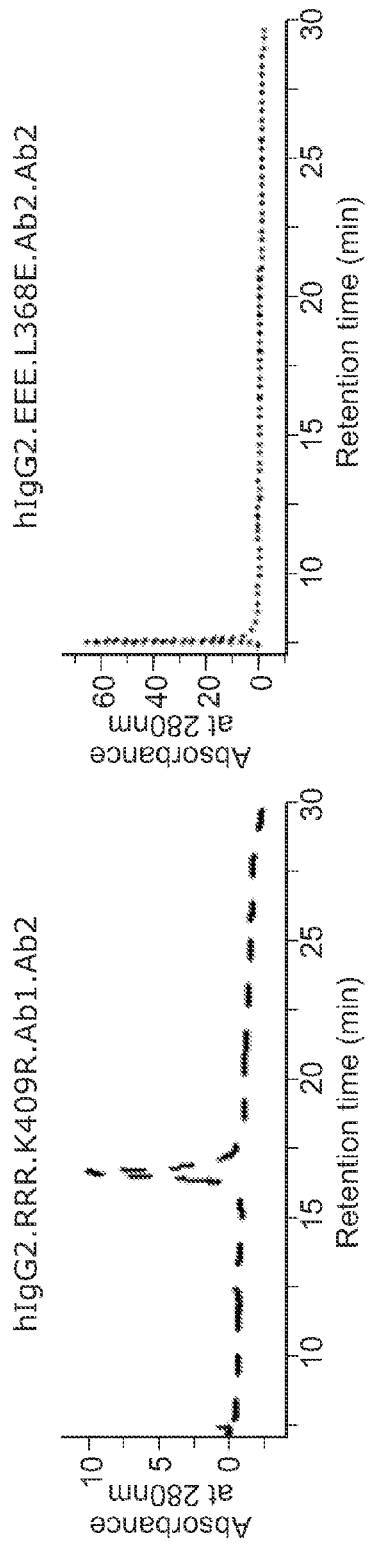
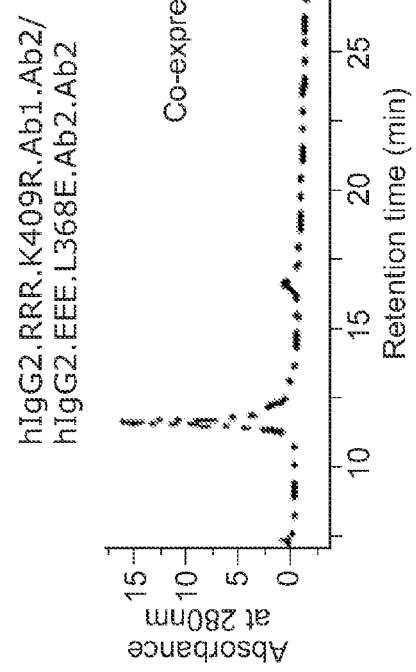
FIG. 19A
FIG. 19B
FIG. 19C
FIG. 19D

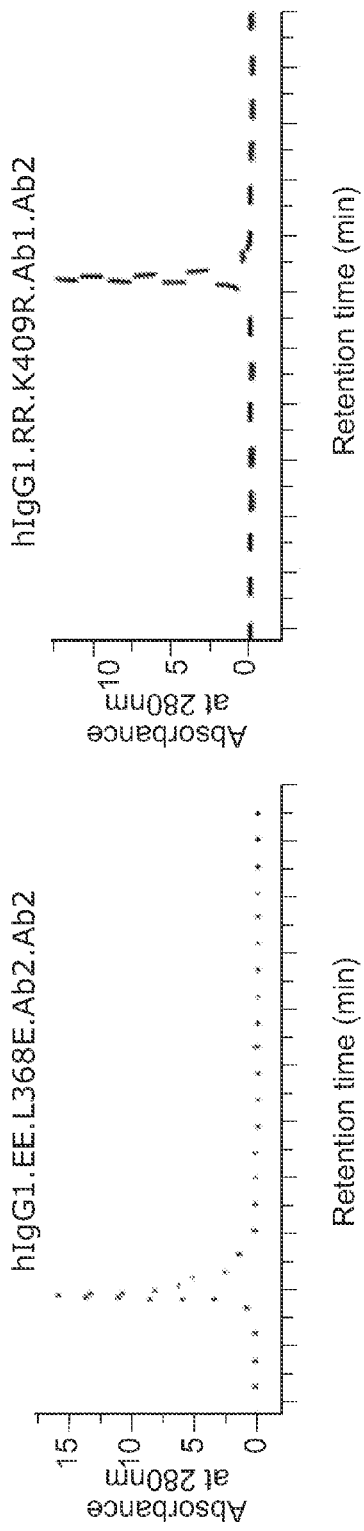
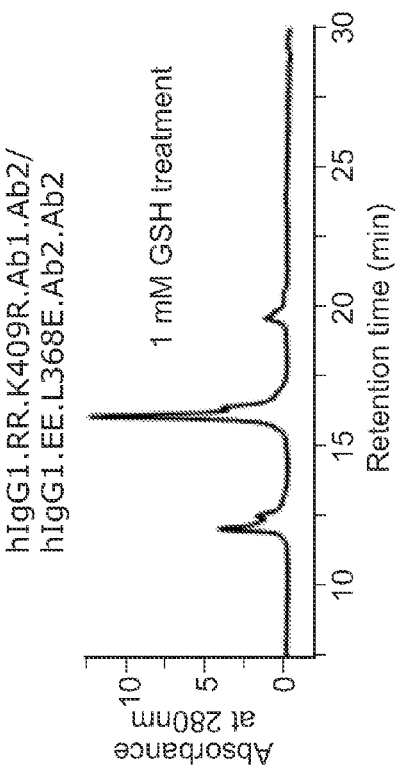
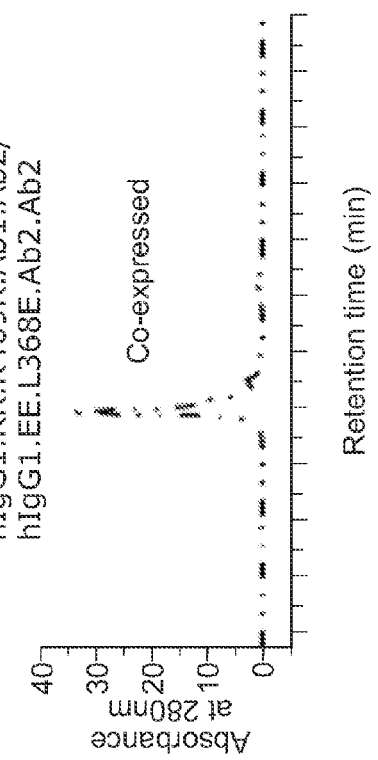
FIG. 20A
FIG. 20B
FIG. 20C
FIG. 20D

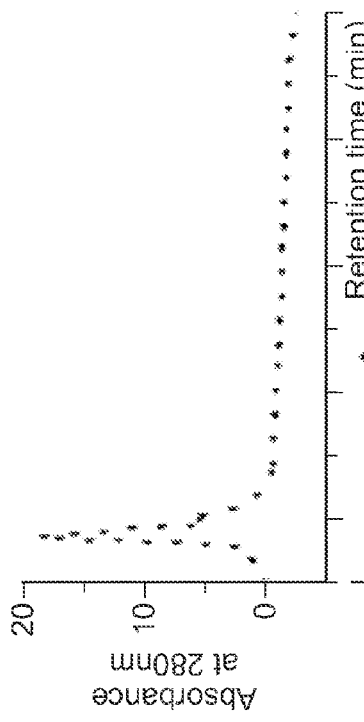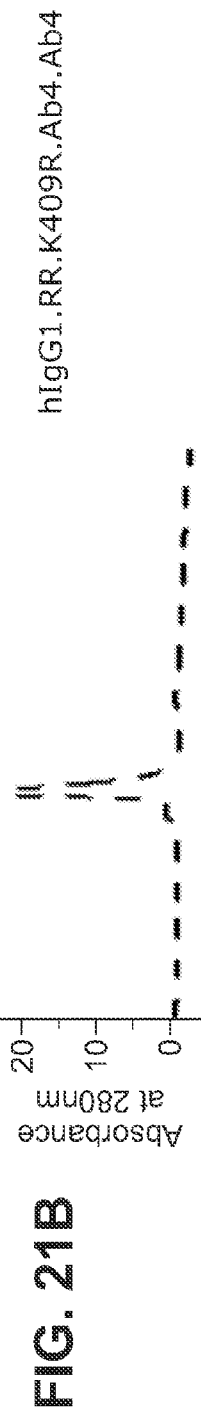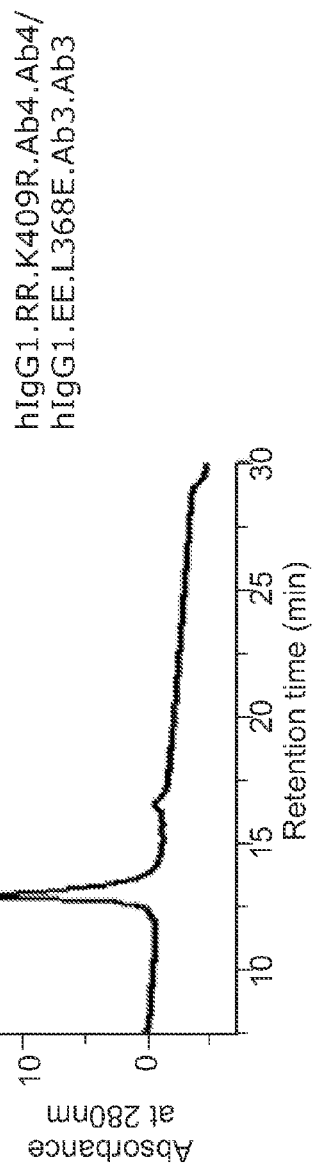
FIG. 21A
FIG. 21B
FIG. 21C

| | Group A | Group B |
|---|---|---|
| 1 | hIgG1.wt.K409R.Ab2.Ab2 | hIgG1.wt.K409R.Ab1.Ab1 |
| 2 | hIgG1.wt.L368E.Ab2.Ab2 | hIgG1.wt.L368E.Ab1.Ab1 |
| 3 | hIgG1.wt.L368E.Ab2.Ab2 | hIgG1.wt.K409R.Ab1.Ab1 |
| 4 | hIgG1.EE.L368E.Ab2.Ab2 | hIgG1.wt.K409R.Ab1.Ab1 |
| 5 | hIgG1.EE.L368D.Ab2.Ab2 | hIgG1.RR.K409R.Ab1.Ab1 |
| 6 | hIgG2.wt.K409R.Ab2.Ab2 | hIgG1.RR.K409R.Ab1.Ab1 |
| 7 | hIgG2.wt.L368E.Ab2.Ab2 | hIgG2.wt.KL368E.Ab1.Ab1 |
| 8 | hIgG2.wt.L368E.Ab2.Ab2 | hIgG2.wt.K409R.Ab1.Ab1 |
| 9 | hIgG2.EEE.L368E.Ab2.Ab2 | hIgG2.RRR.K409R.Ab1.Ab1 |
| 10 | hIgG2.EEE.L368D.Ab2.Ab2 | hIgG2.RRR.K409R.Ab1.Ab1 |
| 11 | hIgG2.EEE.L368E.Ab2.Ab2 | hIgG2.RRR.L368E.Ab1.Ab1 |

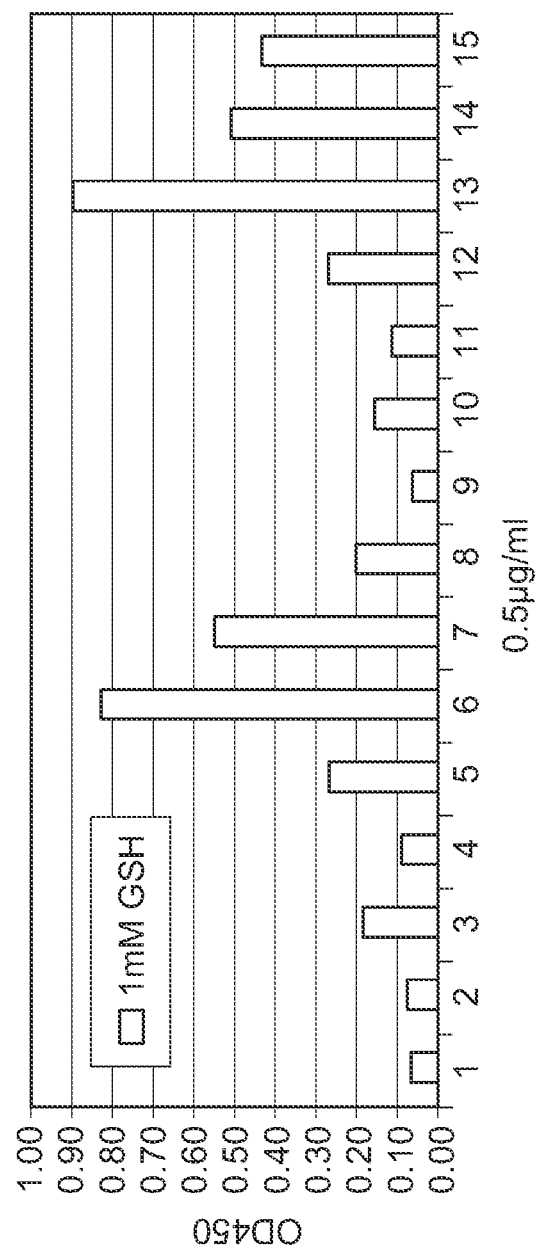

FIG. 25B

| | Group A | Group B |
|---|---|---|
| 1 | Ab2.wild type hIgG2 | Ab1.wild type hIgG1 |
| 2 | hIgG1.EE.wild.Ab2.Ab2 | hIgG1.RR.wild.Ab1.Ab1 |
| 3 | hIgG1.wild.K409R.Ab2.Ab2 | hIgG1.wild.K409R.Ab1.Ab1 |
| 4 | hIgG1.wild.L368E.Ab2.Ab2 | hIgG1.wild.L368E.Ab1.Ab1 |
| 5 | hIgG1.wild.L368E.Ab2.Ab2 | hIgG1.wild.K409R.Ab1.Ab1 |
| 6 | hIgG1.EE.L368E.Ab2.Ab2 | hIgG1.RR.K409R.Ab1.Ab1 |
| 7 | hIgG1.EE.K409R.Ab2.Ab2 | hIgG1.RR.K409R.Ab1.Ab1 |
| 8 | hIgG1.EE.L368E.Ab2.Ab2 | hIgG1.RR.L368E.Ab1.Ab1 |
| 9 | Ab2.wild type.hIgG2 | Ab1.wild type.hIgG2 |
| 10 | hIgG2.wild.K409R.Ab2.Ab2 | hIgG2.wild.K409R.Ab1.Ab1 |
| 11 | hIgG2.wild.L368E.Ab2.Ab2 | hIgG2.wild.L368E.Ab1.Ab1 |
| 12 | hIgG2.wild.L368E.Ab2.Ab2 | hIgG2.wild.K409R.Ab1.Ab1 |
| 13 | hIgG2.EEE.L368E.Ab2.Ab2 | hIgG2.RRR.K409R.Ab1.Ab1 |
| 14 | hIgG2.EEE.L368E.Ab2.Ab2 | hIgG2.RRR.L368E.Ab1.Ab1 |
| 15 | hIgG2.EEE.K409R.Ab2.Ab2 | hIgG2.RRR.K409R.Ab1.Ab1 |

FIG. 28B
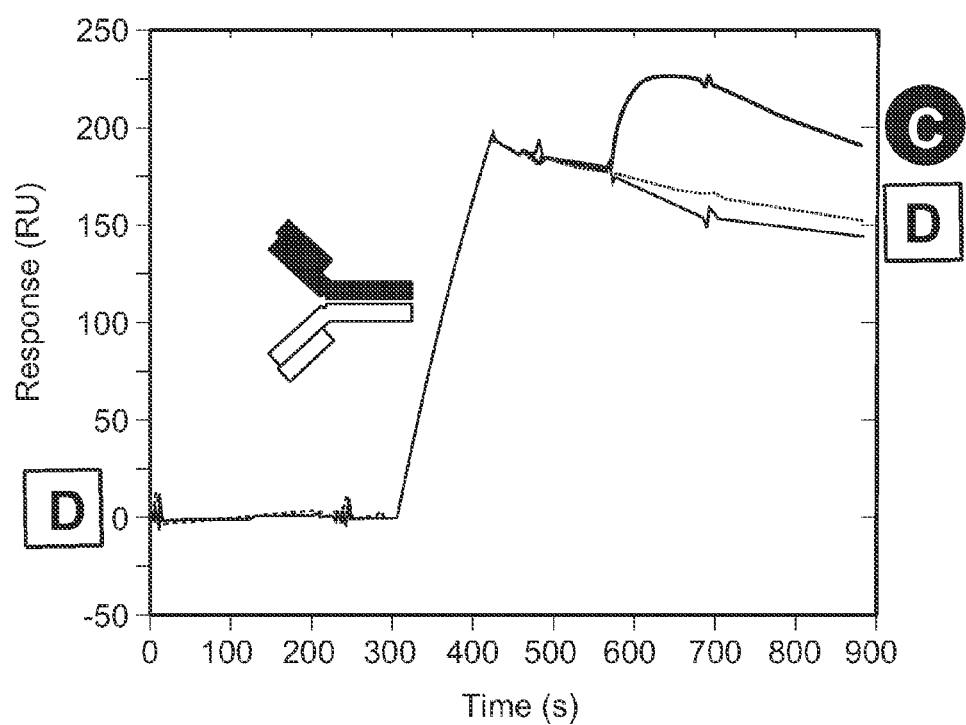
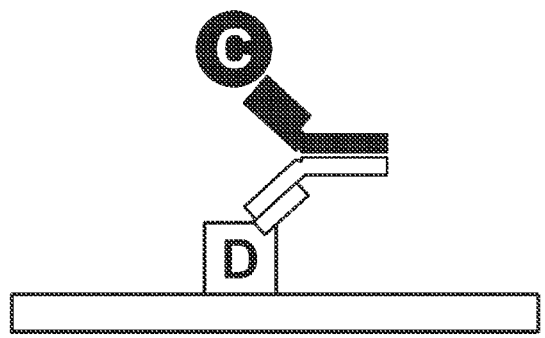

FIG. 29
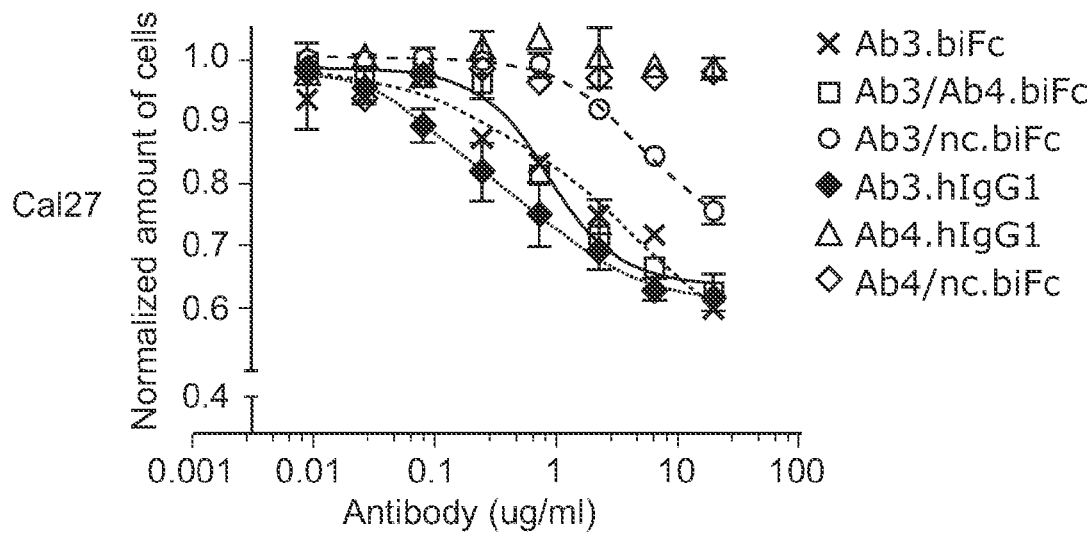
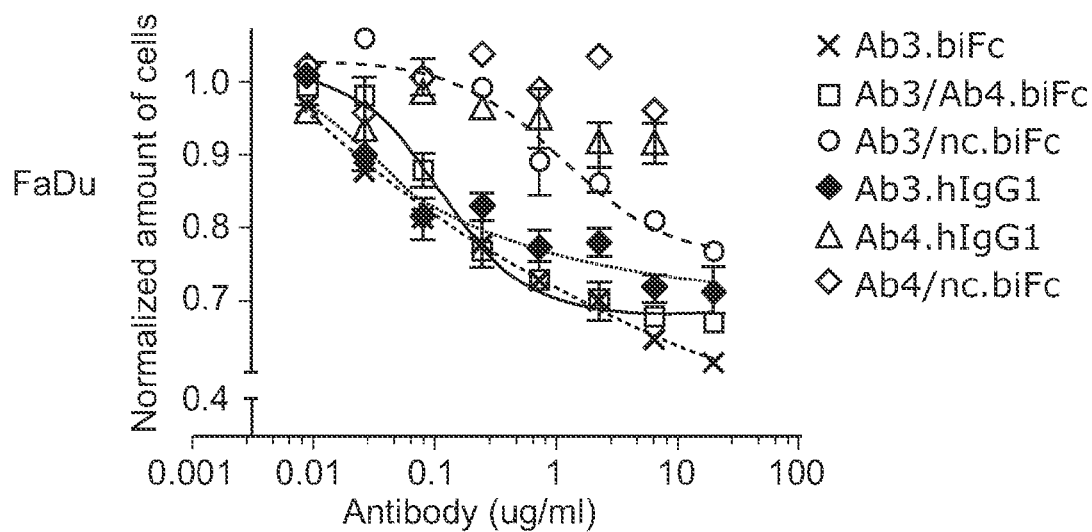

HETERODIMERIC PROTEINS AND METHODS FOR PRODUCING AND PURIFYING THEM

CROSS-REFERENCE TO RELATED APPLICATIONS

This application is a national stage of PCT International Application No. PCT/US2011/036419, filed on May 13, 2011, which claims the benefits of U.S. Provisional Application No. 61/345,047 filed May 14, 2010, and U.S. Provisional Application No. 61/485,097 filed May 11, 2011, which are both hereby incorporated by reference in their entireties.

REFERENCE TO SEQUENCE LISTING

This application is being filed electronically via EFS-Web and includes an electronically submitted sequence listing in .txt format. The .txt file contains a sequence listing entitled "PC71659ASequenceListing ST25.txt" created on Apr. 17, 2015, and having a size of 18 KB. The sequence listing contained in this .txt file is part of the specification and is incorporated herein by reference in its entirety.

FIELD

The present invention relates to engineered heteromultimeric proteins, and more specifically, to methods for producing and purifying heterodimeric proteins, such as bispecific antibodies and other heterodimeric proteins comprising immunoglobulin-like hinge sequences. Methods for producing and purifying such engineered heterodimeric proteins and their use in diagnostics and therapeutics are also provided.

BACKGROUND

Antibodies possess a variety of properties which make them useful as therapeutic molecules. In addition to their ability to bind with high affinity to a molecular target inside or outside of cells with high specificity and selectivity, antibodies render their targeted binding partners susceptible to Fc-receptor cell-mediated phagocytosis and killing through effector functions, such as complement induced pathways and ADCC (antibody-dependent cell-mediated cytotoxicity) related activities.

Further, antibodies may be engineered in a variety of ways to further increase their therapeutic utility. Antibodies having extended in vivo half-lives, for example, may be produced by engineering Fc fusion molecules, by treatment with biocompatible polymers such as polyethylene glycol (PEG), or "pegylation" and by other engineering methods well known in the art. Antibodies have binding specificities for at least two different antigens, called bispecific antibodies (BsAbs), have also been engineered. See Nolan, O. and R. O'Kennedy (1990) Biochim Biophys Acta 1040(1): 1-11.; de Leij, L. et al., Adv Drug Deliv Rev 31(1-2): 105-129 (1998); and Carter, P. J Immunol Methods 248(1-2): 7-15 (2001)). While classical antibodies have identical sequences in each of the two arms (containing the antigen binding sites of Fab region) of the Y-shaped molecule, bispecific antibodies have different sequences in each of the two Fab regions so that each arm of the Y-shaped molecule binds to a different antigen or epitope.

By being able to bind two different antigenic molecules or different epitopes, BsAbs offer a wide variety of clinical applications as targeting agents for in vitro and in vivo diagnostics and immunotherapies. In diagnostic areas, BsAbs have been used, e.g., to study functional properties of cell surface molecules, different Fc receptors and their ability to mediate cytotoxicity (Fanger et al., Crit. Rev. Immunol. 12:101-124 (1992); Nolan et al., Biochem. Biophys. Acta. 1040:1-11 (1990); and to immobilize enzymes and other agents to produce immunodiagnostic and immunoassay reagents and methods.

Bispecific antibodies can also be used for in vitro or in vivo diagnoses of various disease states, including cancer (Songsivilai et al., Clin. Exp. Immunol. 79:315 (1990)). For example, one arm of the BsAb can be engineered to bind a tumor-associated antigen and the other arm to bind a detectable marker. (See, e.g., Le Doussal et al., J. Nucl. Med. 34:1662-1671 (1993), in which a BsAb having one arm which bound a carcinoembryonic antigen (CEA) and another arm which bound DPTA was used for radioimmunodetection of colorectal and thyroid carcinomas. See also Stickney et al., Cancer Res. 51:6650-6655 (1991), describing a strategy for detecting colorectal cancers expressing CEA by radioimmunodetection.

The use of bispecific antibodies for immunotherapy of cancer has been reviewed (see e.g., Nolan and O'Kennedy 1990, supra; de Leij et al. (1998) supra; and Carter, P. (2001) supra.) BsAbs can be used to direct a patient's cellular immune defense mechanisms specifically to a tumor cell or an infectious agent (e.g., virally infected cells such as HIV or influenza virus; protozoa such as Toxoplasma gondii). In particular, one can redirect immune modulated cytotoxicity by engineering one arm of the BsAb to bind to a desired target (e.g. tumor cell or pathogen) and the other arm of the BsAb to bind to a cytotoxic trigger molecule, such as the T-cell receptor or a Fc gamma receptor (thereby activating downstream immune effector pathways). Using this strategy, BsAbs which bind to the Fc gamma RIII have been shown to mediate tumor cell killing by natural killer (NK) cell/large granular lymphocyte (LGL) cells in vitro and to prevent tumor growth in vivo. (See, e.g., Segal et al., Chem. Immunol. 47:179 (1989); Biologic Therapy of Cancer 2(4) DeVita et al. eds. J. B. Lippincott, Philadelphia (1992) p. 1.) In another example, a bispecific antibody having one arm that binds Fc gamma RIII and another that binds the HER2 receptor was developed for treatment of tumors that overexpress HER2 antigen (Hseih-Ma et al. Cancer Research 52:6832-6839 (1992); and Weiner et al. Cancer Research 53:94-100 (1993)). See also Shalaby et al., J. Exp. Med. 175(1):217 (1992) in which a fully humanized F(ab')2 BsAb comprising anti-CD3 linked to anti-p185(HER2) was used to target T cells to kill tumor cells that overexpress HER2 receptor.

Use of bispecific antibodies has been hindered by difficulties in obtaining BsAbs in sufficient quantity and purity. Traditionally, BsAbs were made using hybrid-hybridoma technology (Millstein and Cuello, Nature 305:537-539 (1983)). Methods for making BsAbs by chemical coupling have since been described (see, e.g., Shalaby et al., J. Exp. Med. 175:217-225 (1992); Rodrigues et al., Int. J. Cancers (Suppl.) 7:45-50 (1992); Kostelny et al., J. Immunol. 148 (5):1547-1553 (1992). Diabody technology described by Hollinger et al., Proc. Natl. Acad. Sci. USA 90:6444-6448 (1993) has provided alternative procedures for making BsAb fragments; as has the use of single chain Fv (sFv) dimers (see, e.g., Gruber et al., J. Immunol. 152: 5368 (1994).

To produce multispecific (e.g., bispecific) antibody heteromultimers (e.g., heterodimers), it is desirable to use methods that favor formation of the desired heteromultimer over homomultimer(s). One method for obtaining Fc-containing BsAbs remains the hybrid hybridoma technique, in which two antibodies are co-expressed (Milstein and Cuello, *Nature* 305:537-540 (1983); see Suresh, M. R., et al. *Methods Enzymol* 121:210-228 (1986)). However, it is often inefficient with respect to yield and purity, the desired heteromultimer often being difficult to further purify. Other techniques to favor heteromultimer formation have been described and involve engineering sterically complementary mutations in multimerization domains at the CH3 domain interface, referred to as a "knobs-into-holes" strategy (see e.g., Ridgway et al., *Protein Eng.* 9:617-621 (1996); Merchant et al., *Nat. Biotechnol.* 16(7): 677-81 (1998); see also U.S. Pat. Nos. 5,731,168 and 7,183,076). Techniques involving replacing one or more residues that make up the CH3-CH3 interface in both CH3 domains with a charged amino acid for promoting the heterodimer formation have also been described. WO2009/089004.

It would be desirable to find new methods for engineering bispecific antibody fragments and/or full length BsAbs, such as those which enable the BsAbs to be expressed and recovered directly or efficiently from recombinant cell culture and/or which may be produced with efficient yields and purities, or having increased stability compared to bispecific antibodies in the art.

SUMMARY

In one aspect, this invention provides a heteromultimeric (e.g., heterodimeric) protein comprising a hinge region, wherein the hinge region comprises a first immunoglobulin-like hinge polypeptide and a second immunoglobulin-like hinge polypeptide which interact together to form a dimeric hinge interface, wherein electrostatic interactions between one or more charged amino acids within the hinge interface favor interaction between the first and second hinge polypeptides over interaction between two first hinge polypeptides or two second hinge polypeptides, thereby promoting heterodimer formation over homodimer formation. In some embodiments, the hinge region is an IgG hinge region. In some embodiments, the hinge region is an IgG1, IgG2, IgG3, or IgG4 hinge region. In some embodiments, the IgG hinge region comprises a human IgG hinge region (e.g., human IgG1, IgG2, IgG3, or IgG4 hinge region).

In some embodiments, the first hinge polypeptide comprises at least one amino acid modification relative to a wild-type (WT) hinge region (e.g., IgG hinge region), wherein the wild-type amino acid is replaced with an amino acid having an opposite charge to the corresponding amino acid in the second hinge polypeptide.

In some embodiments, the first hinge polypeptide comprises at least one amino acid modification relative to a wild-type hinge region (e.g., IgG hinge region), and the second hinge polypeptide comprises at least one amino acid modification relative to a wild-type hinge region (e.g., IgG hinge region) in proximity to or at the same position as the amino acid modification in the first hinge polypeptide, wherein the wild-type amino acid in the second hinge polypeptide is replaced with an amino acid having an opposite charge to the corresponding amino acid in the first hinge polypeptide. In some embodiments, the amino acid modifications can be charged residues (e.g., Lys, Arg, His, Glu, and Asp) or polar residues (e.g., Ser and Thr). In some embodiments, the first hinge polypeptide comprises a human IgG1 and the amino acid modification in the first hinge polypeptide is at a position selected from the group consisting of 221 and 228. In some embodiments, the first hinge polypeptide comprises a human IgG2 and the amino acid modification in the first hinge polypeptide is at a position selected from the group consisting of 223, 225, and 228. In some embodiments, the first hinge polypeptide comprises a human IgG4, and the amino acid modification in the first hinge polypeptide is at position 228.

In other embodiments, the heterodimeric protein of the invention further comprises a CH3 region, wherein the CH3 region comprises a first CH3 polypeptide and a second CH3 polypeptide which interact together to form a CH3 interface, wherein one or more amino acids within the CH3 interface destabilize homodimer formation and are not electrostatically unfavorable to homodimer formation.

In some embodiments, the heteromultimeric (e.g. heterodimeric) protein of the invention can be, for example, an antibody, a maxibody, a monobody, a peptibody, and an Fc fusion protein. In some embodiments, the heterodimeric protein is a bispecific antibody. In some embodiments, the heterodimeric protein is monospecific monovalent, bispecific monovalent, or bispecific bivalent (e.g., monospecific monovalent antibody, bispecific monovalent, or bispecific bivalent antibody).

In another aspect, this invention provides a strategy for enhancing the formation of a desired heteromultimeric or heterodimeric protein (e.g., bispecific antibody) by altering or engineering an interface between a first and a second immunoglobulin-like Fc region (e.g., a hinge region and/or a CH3 region). In some embodiments, one or more residues that make up the hinge interface are replaced with charged residues such that the electrostatic interactions between these charged residues electrostatically favor heterodimer formation over homodimer formation. In further embodiments, one or more residues that make up the CH3 interface are further replaced with charged residues such that the interactions between the CH3 interface further promotes heterodimer formation over homodimer formation. In some embodiments, the engineered CH3 interface destabilizes homodimer formation. In some embodiments, the engineered CH3 interface is not electrostatically unfavorable to homodimer formation. In some embodiments, the engineered CH3 interface sterically favors heterodimer formation over homodimer formation. In some embodiments, the engineered CH3 interface electrostatically favor heterodimer formation over homodimer formation.

In another aspect, disclosed herein are heteromultimeric (e.g., a heterodimeric) proteins comprising an immunoglobulin-like CH3 region comprising a first CH3 polypeptide and a separate second CH3 polypeptide that interact together to form a CH3 interface, wherein one or more amino acids within the CH3 interface destabilize homodimer formation and are not electrostatically unfavorable to homodimer formation. In some embodiments, the first CH3 polypeptide comprises an amino acid modification relative to a wild-type CH3 region sequence. In some embodiments, the first CH3 polypeptide further comprises a second amino acid modification relative to a wild-type CH3 sequence. In some embodiments, the first CH3 polypeptide further comprises a third amino acid modification relative to a wild-type CH3 sequence. In some embodiments, the second CH3 polypeptide comprises an amino acid modification relative to a wild-type CH3 region sequence. In some embodiments, the second CH3 polypeptide further comprises a second amino acid modification relative to a wild-type CH3 region sequence. In some embodiments, the second CH3 polypeptide further comprises a third amino acid modification relative to a wild-type CH3 region sequence.

In some embodiments, the CH3 region is an IgG1, IgG2, IgG3, or IgG4 CH3 region. In some embodiments, the CH3 region comprises a human IgG CH3 region (e.g., human IgG1, IgG2, IgG3, or IgG4 CH3 region).

In some embodiments, the amino acid modification in the CH3 polypeptide is an amino acid substitution at a position selected from the group consisting of 349, 368, 405 and 409. In some embodiments, the amino acid modification is selected from the group consisting of K409R, L368E, and L368D.

In some embodiments, an amino acid modification in the first CH3 polypeptide is K409R and an amino acid modification in the second CH3 polypeptide is L368E or L368D.

In another aspect, this invention also provides a method of producing a heteromultimeric, (e.g., heterodimeric) protein of the invention comprising the steps of: a) culturing a host cell comprising a nucleic acid molecule encoding the first polypeptide and a nucleic acid molecule encoding the second polypeptide (the first and second polypeptides expressed from the same or from one or more different nucleic acid molecules), wherein the cultured host cell expresses the first and second polypeptides; and b) optionally, recovering the heterodimeric protein from the host cell culture.

In another aspect, this invention also provides a method of producing a heteromultimeric, (e.g., heterodimeric) protein of the invention comprising the steps of: a) expressing the first polypeptide in a first host cell; b) expressing the second polypeptide in a second host cell; c) optionally, isolating the first polypeptide and the second polypeptide; and d) incubating the two polypeptides under a condition suitable for dimerization (for example, using a reducing agent such as, e.g., glutathione) to produce the heterodimeric protein.

In another aspect, this invention provides a method of purifying a heterodimeric protein comprising one or more Fc regions (e.g., a hinge region and/or a CH3 region) which electrostatically favor heterodimer formation over homodimer formation.

In another aspect, this invention also provides methods of purifying a heterodimeric protein comprising an immunoglobulin-like Fc region and the purification comprises at least one step that is based on differences in electrostatic interaction in the Fc regions. The heterodimeric protein that can be purified by the methods of this invention may comprise an immunoglobulin-like hinge region and/or constant region (e.g., CH2 region or CH3 region).

In some embodiments, the method comprises at least one step that is based on differences in electrostatic interaction in the hinge region. In some embodiments, the method comprises at least one step that is based on differences in electrostatic interaction in the constant region. In some embodiments, the constant region can be a heavy chain constant region, a CH2 region, or a CH3 region. In some embodiments, the method comprises a chromatography step (e.g., ion exchange chromatography).

In another aspect, this invention provides polypeptides, nucleic acids, vectors and host cells that relate to the production of a heteromultimeric (e.g., heterodimeric) protein of the invention. This invention also provides pharmaceutical compositions/formulations that comprise a heteromultimeric, e.g., heterodimeric protein of the invention and methods of using such compositions.

In another aspect, a method of treating a condition, disorder or disease in a subject is provided, the method comprising administering to the subject an effective amount of a pharmaceutical composition comprising a heteromultimeric (e.g., heterodimeric) protein of the invention.

In another aspect, this invention also provides a polypeptide comprising an immunoglobulin-like hinge polypeptide, wherein the hinge polypeptide comprises at least one amino acid modification relative to a wild-type immunoglobulin-like hinge polypeptide, wherein the polypeptide has increased ability to form a heterodimeric protein with a second polypeptide, compared to a polypeptide comprising the wild-type immunoglobulin-like hinge polypeptide.

In another aspect, this invention also provides a polypeptide comprising an CH3 polypeptide, wherein the CH3 polypeptide comprises at least one amino acid modification relative to a wild-type CH3 polypeptide, wherein the polypeptide has increased ability to form a heterodimeric protein with a second polypeptide, compared to a polypeptide comprising the wild-type CH3 hinge polypeptide. In some embodiments, the amino acid modification is selected from the group consisting of K409R, L368E, and L368D.

In another aspect of the invention, the heterodimeric protein (e.g., bispecific antibody) as described herein comprises a full-length human antibody, wherein a first antibody variable domain of the heterodimeric protein is capable of recruiting the activity of a human immune effector cell by specifically binding to an effector antigen located on the human immune effector cell, wherein a second antibody variable domain of the heterodimeric protein is capable of specifically binding to a target antigen. In some embodiments, the human antibody has an IgG1, IgG2, IgG3, or IgG4 isotype.

BRIEF DESCRIPTION OF THE DRAWINGS

FIG. 2 depicts human IgG2ΔA Fc region sequence (SEQ ID NO depicts 1).

FIG. 4 depicts human IgG1 wild-type Fc region sequence (SEQ ID NO depicts 11).

FIG. 5 depicts human IgG4 wild-type Fc region sequence (SEQ ID NO depicts 12).

FIG. 6A depicts an alignment of human IgG1 (EPKSCD-KTHCPPCP (SEQ ID NO: 57)), IgG2 (ERKCCVECPPCP (SEQ ID NO: 56)), and IgG4 (ESKYGPPCPSCP (SEQ ID NO: 55)) hinge regions.

FIG. 6B depicts a table of human IgG 4 and IgG1 mutants.

FIG. 6C depicts a table of human IgG2 mutants.

FIGS. 8A-8B depict an analysis of bispecific antibody formation from IgG2 mutants.

FIGS. 9A-9B depict results from a screen for IgG2 hinge mutations in K409R background.

FIG. 10 depicts an alignment of human IgG4 (SEQ ID NO: 60), IgG2ΔA (SEQ ID NO: 59), and IgG1 (SEQ ID NO: 58) CH3 regions.

FIGS. 11A-11B depicts results for "Glu" scanning on various human IgG4 mutants.

FIGS. 13A-13B depict mutations in both hinge regions and CH3 regions are important for heterodimer/bispecific antibody formation of human IgG2 mutants.

FIGS. 16A-16C depict ion exchange elution profiles of hIgG1 mutants. Dashed line represents Ab1 antibody with 221R and 228R mutations in the hinge region and 409R mutation in the CH3 domain of the heavy chain. Dotted line represents Ab2 hIgG1 antibody with 221E and 228E mutations in the hinge and 368E in the CH3 domain. Solid line represents elution profile of the Ab1-Ab2 bispecific antibody reaction products formed after incubation of the Ab1 and Ab2 variants with 1 mM glutathione.

FIGS. 17A-17C depict ion exchange elution profiles of hIgG2 mutants. Dashed line represents Ab1 antibody with 223R, 225R, and 228R mutations in the hinge region and 409R mutation in the CH3 domain of the heavy chain. Dotted line represents Ab2 hIgG1 antibody with 223E, 225E, and 228E mutations in the hinge and 368E in the CH3 domain. Solid line represents elution profile of the Ab1-Ab2 bispecific antibody reaction products formed after incubation of the Ab1 and Ab2 variants with 2 mM glutathione.

FIGS. 19A-19D depict co-expression of modified hinge polypeptides with light chain sequences produces bispecific antibodies. Dash-dot-dot line represents ion exchange chromatography trace of bispecific antibodies formed by co-expressing hIgG2.RRR.K409R.Ab1 heavy chain with hIgG2.EEE.L368E.Ab2 heavy chain, and Ab2 light chain. Solid line represents elution profile of the Ab1-Ab2 bispecific antibody reaction products formed after incubation of the purified Ab1 (223R, 225R, 228R, and 409R) heavy chain with Ab2 light chain and Ab2 (223E, 225E, 228E, and 368E) with 2 mM glutathione. Dotted line represents control antibody Ab2 hIgG2 with 223E, 225E, 228E, and 368E mutations. Dashed line represents control Ab1 antibody with 223R, 225R, 228R, and 409R mutations in the heavy chain expressed together with Ab2 light chain.

FIGS. 20A-20D depict co-expression of modified hinge polypeptides with light chain sequences produces bispecific antibodies. Dash-dot-dot line represents ion exchange chromatography trace of bispecific antibodies formed by co-expressing hIgG1.RR.K409R.Ab1 heavy chain with hIgG1.EE.L368E.Ab2 heavy chain, and Ab2 light chain. Solid line represents elution profile of the Ab1-Ab2 bispecific antibody reaction products formed after incubation of the purified Ab1 (221R, 228R, and 409R) heavy chain with Ab2 light chain and Ab2 (221E, 228E, and 368E) with 1 mM glutathione. Dotted line represents control antibody Ab2 hIgG1 with 221E, 228E, and 368E mutations. Dashed line represents control Ab1 antibody with 221R, 228R, and 409R mutations in the heavy chain co-expressed together with Ab2 light chain.

FIGS. 21A-21C depict the method of the invention does not depend on the identity of the variable domains and is thus widely applicable. Dashed line represents Ab4 antibody with 221R and 228R mutations in the hinge region and 409R mutation in the CH3 domain of the heavy chain. Dotted line represents Ab3 hIgG1 antibody with 221E and 228E mutations in the hinge and 368E in the CH3 domain. Solid line represents elution profile of the Ab4-Ab3 bispecific antibody reaction products formed after incubation of the Ab4 and Ab3 variants with 1 mM glutathione.

FIGS. 25A-25B also depict (A) a comparison of bispecific antibody formation for the indicated mutants (B).

FIGS. 28A-28B depict sensorgrams showing the binding of a bispecific antibody to amine-coupled (antigen A)-hFc or (antigen D)-hFc and binding to a panel of "sandwiching" analytes (or antigens).

FIG. 29 shows that growth inhibition by monospecific and bispecific Ab3 and Ab4 was assayed in Cal27 (top panel) and FaDu (bottom panel) cells. Ab3.biFc (cross) is the parental mutant antibody (hIgG1.EE.L368E.Ab3.Ab3/hIgG1.EE.L368E.Ab3.Ab3). Ab3-Ab4 bispecific antibody (open square) is the bispecific mutant antibody (hIgG1.EE.L368E.Ab3.Ab3/hIgG1.RR.K409R.Ab4.Ab4). Ab3/nc.biFc (open circle) is the monovalent Ab3 with a negative control antibody (Ab6) on one arm (hIgG1.RR.K409R.Ab3.Ab3/hIgG1.EE.L368E.Ab6.Ab6). Ab3.hIgG1 (filled diamond) is the wild-type bivalent Ab3 in hIgG1 (Ab3.wild-type hIgG1). Ab4.hIgG1 (open triangle) is the wild-type bivalent Ab4 in hIgG1 (Ab4.wild-type hIgG1). Ab4nc.biFc (open diamond) is the monovalent Ab4 with a negative control antibody (Ab6) in one arm (hIgG1.RR.K409R.Ab4.Ab4/hIgG1.EE.L368E.Ab6.Ab6). "nc" denotes negative control antibody.

DETAILED DESCRIPTION

Figure 1:
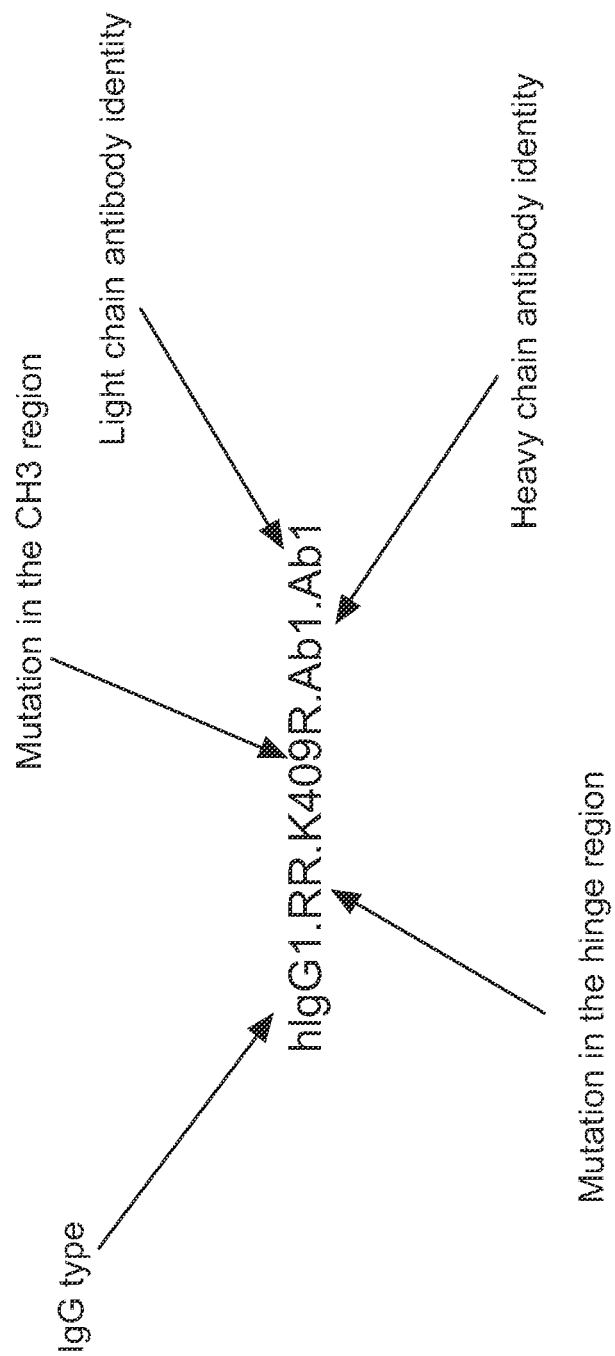
FIG. 1 depicts an exemplary antibody mutant to describe the nomenclature system used by this application to describe a heterodimeric protein.

The invention provides improved methods, compositions, kits and articles of manufacture for generating heteromultimeric complex molecules, and more particularly, heterodimeric proteins comprising at least one immunoglobulin-like hinge region, such as, e.g., a bispecific antibody. The invention provides methods to make and to purify heteromultimeric complex molecules in pragmatic yields and desirable purities. The invention makes possible the efficient production of complex molecules that in turn can be used for diagnosing and/or treating various disorders or pathological conditions in which use of a molecule that is multispecific in nature and highly stable is desirable and/or required. Details of methods, compositions, kits and articles of manufacture of the invention are provided herein.

General Techniques and Definitions

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. Generally, nomenclature used in connection with, and techniques of, cell and tissue culture, molecular biology, immunology, microbiology, genetics and protein and nucleic acid chemistry and hybridization described herein are those well known and commonly used in the art.

The methods and techniques of the present invention are generally performed according to conventional methods well known in the art and as described in various general and more specific references that are cited and discussed throughout the present specification unless otherwise indicated. See, e.g., Sambrook J. & Russell D. *Molecular Cloning: A Laboratory Manual*, 3rd ed., Cold Spring Harbor Laboratory Press, Cold Spring Harbor, N.Y. (2000); Ausubel et al., *Short Protocols in Molecular Biology: A Compendium of Methods from Current Protocols in Molecular Biology*, Wiley, John & Sons, Inc. (2002); Harlow and Lane *Using Antibodies: A Laboratory Manual*, Cold Spring Harbor Laboratory Press, Cold Spring Harbor, N.Y. (1998); and Coligan et al., *Short Protocols in Protein Science*, Wiley, John & Sons, Inc. (2003). Enzymatic reactions and purification techniques are performed according to manufacturer's specifications, as commonly accomplished in the art or as described herein. The nomenclature used in connection with, and the laboratory procedures and techniques of, molecular biology, biochemistry, immunology, analytical chemistry, synthetic organic chemistry, and medicinal and pharmaceutical chemistry described herein are those well known and commonly used in the art. Throughout this specification and claims, the word "comprise," or variations such as "comprises" or "comprising," will be understood to imply the inclusion of a stated integer or group of integers but not the exclusion of any other integer or group of integers.

An "antibody" is an immunoglobulin molecule capable of specific binding to a target, such as a carbohydrate, polynucleotide, lipid, polypeptide, etc., through at least one antigen recognition site, located in the variable region of the immunoglobulin molecule. As used herein, unless otherwise indicated by context, the term is intended to encompass not only intact polyclonal or monoclonal antibodies, but also fragments thereof (such as Fab, Fab', F(ab')$_2$, Fv), single chain (ScFv) and domain antibodies, including shark and camelid antibodies), and fusion proteins comprising an antibody portion, multivalent antibodies, multispecific antibodies (e.g., bispecific antibodies so long as they exhibit the desired biological activity) and antibody fragments as described herein, and any other modified configuration of the immunoglobulin molecule that comprises an antigen recognition site, for example without limitation, minibodies, maxibody, monobodies, peptibodies, intrabodies, diabodies, triabodies, tetrabodies, v-NAR and bis-scFv (see, e.g., Hollinger and Hudson, *Nature Biotech.* 23(9): 1126-1136 (2005)). An antibody includes an antibody of any class, such as IgG, IgA, or IgM (or sub-class thereof), and the antibody need not be of any particular class. Depending on the antibody amino acid sequence of the constant domain of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1 and IgA2. The heavy-chain constant domains that correspond to the different classes of immunoglobulins are called alpha, delta, epsilon, gamma, and mu, respectively. The subunit structures and three-dimensional configurations of different classes of immunoglobulins are well known.

"Antibody fragments" comprise only a portion of an intact antibody, wherein the portion preferably retains at least one, preferably most or all, of the functions normally associated with that portion when present in an intact antibody.

The residue designations in this application are based on the EU numbering scheme of Kabat (Kabat et al., 1991, *Sequences of Proteins of Immunological Interest*, National Institutes of Health, Bethesda, Md., ed. 5).

A "bivalent antibody" comprises two antigen binding sites per molecule (e.g., IgG). In some instances, the two binding sites have the same antigen specificities. However, bivalent antibodies may be bispecific (see below).

A "monovalent antibody" comprises one antigen binding site per molecule (e.g., IgG). In some instances, a monovalent antibody can have more than one antigen binding sites, but the binding sites are from different antigens.

A "multispecific antibody" is one that targets more than one antigen or epitope. A "bispecific," "dual-specific" or "bifunctional" antibody is a hybrid antibody having two different antigen binding sites. Bispecific antibodies are a species of multispecific antibody and may be produced by a variety of methods including, but not limited to, fusion of hybridomas or linking of Fab' fragments. See, e.g., Songsivilai & Lachmann (1990), *Clin. Exp. Immunol.* 79:315-321; and Kostelny et al. (1992), *J. Immunol.* 148:1547-1553. The two binding sites of a bispecific antibody will bind to two different epitopes, which may reside on the same or different protein targets.

The phrase "antigen binding arm," "target molecule binding arm," and variations thereof, as used herein, refers to a component part of an antibody of the invention that has an ability to specifically bind a target molecule of interest. Generally and preferably, the antigen binding arm is a complex of immunoglobulin polypeptide sequences, e.g., CDR and/or variable domain sequences of an immunoglobulin light and heavy chain.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigen. Further, in contrast to polyclonal antibody preparations that typically include different antibodies directed against different determinants (epitopes), each monoclonal antibody is directed against a single determinant on the antigen.

The monoclonal antibodies herein may, in certain embodiments, specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., *Proc. Natl. Acad. Sci. USA* 81:6851-6855 (1984)).

"Humanized" forms of non-human (e.g., murine) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, framework region (FR) residues of the human immunoglobulin are replaced by corresponding non-human residues. Humanized antibodies may, moreover, comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally will also comprise at least a portion of an immunoglobulin constant region (Fc), typically that of a human immunoglobulin. For further details, see Jones et al., *Nature* 321:522-525 (1986); Riechmann et al., *Nature* 332:323-329 (1988); and Presta, *Curr. Op. Struct. Biol.* 2:593-596 (1992). See also the following review articles and references cited therein: Vaswani and Hamilton, *Ann. Allergy, Asthma & Immunol.* 1:105-115 (1998); Harris, *Biochem. Soc. Transactions* 23:1035-1038 (1995); Hurle and Gross, *Curr. Op. Biotech.* 5:428-433 (1994).

A "human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen-binding residues.

As used herein, the term "immunoadhesin" designates antibody-like or immunoglobulin-like molecules which combine the "binding domain" of a heterologous protein (an "adhesin", e.g. a receptor, ligand or enzyme) with the effector component of immunoglobulin constant domains. Structurally, the immunoadhesins comprise a fusion of the adhesin amino acid sequence with the desired binding specificity which is other than the antigen recognition and binding site (antigen combining site) of an antibody (i.e. is "heterologous") and an immunoglobulin constant domain sequence. The immunoglobulin constant domain sequence in the immunoadhesin may be obtained from any immunoglobulin, such as IgG1, IgG2, IgG3, or IgG4 subtypes, IgA, IgE, IgD or IgM.

A "heteromultimer", "heteromultimeric complex", or "heteromultimeric polypeptide" is a molecule comprising at least a first polypeptide and a second polypeptide, wherein the second polypeptide differs in amino acid sequence from the first polypeptide by at least one amino acid residue. The heteromultimer can comprise a "heterodimer" formed by the first and second polypeptide or can form higher order tertiary structures where polypeptides in addition to the first and second polypeptide are present.

A "heterodimer," "heterodimeric protein," "heterodimeric complex," or "heteromultimeric polypeptide" is a molecule comprising a first polypeptide and a second polypeptide, wherein the second polypeptide differs in amino acid sequence from the first polypeptide by at least one amino acid residue.

The terms "polypeptide", "oligopeptide", "peptide" and "protein" are used interchangeably herein to refer to chains of amino acids of any length, preferably, relatively short (e.g., 10-100 amino acids). The chain may be linear or branched, it may comprise modified amino acids, and/or may be interrupted by non-amino acids. The terms also encompass an amino acid chain that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. It is understood that the polypeptides can occur as single chains or associated chains.

The term "Fc region" as used herein generally refers to a dimer complex comprising the C-terminal polypeptide sequences of an immunoglobulin heavy chain, wherein a C-terminal polypeptide sequence is that which is obtainable by papain digestion of an intact antibody. The Fc region may comprise native or variant Fc sequences. The Fc sequence of an immunoglobulin generally comprises two constant domains, a CH2 domain and a CH3 domain, and optionally comprises a CH4 domain. The term "Fc polypeptide" is used herein to refer to one of the polypeptides that makes up an Fc region. In some embodiments, an Fc polypeptide may be obtained or derived from any suitable immunoglobulin, such as from at least one of the various IgG1, IgG2, IgG3, or IgG4 subtypes, or from IgA, IgE, IgD or IgM. In some embodiments, an Fc polypeptide comprises part or all of a wild-type hinge sequence (generally at its N terminus). In some embodiments, an Fc polypeptide does not comprise a wild-type hinge sequence. An Fc polypeptide may comprise native or variant Fc sequences.

By "Fc fusion" as used herein is meant a protein wherein one or more polypeptides is operably linked to an Fc polypeptide. An Fc fusion combines the Fc region of an immunoglobulin with a fusion partner, which in general may be any protein, polypeptide or small molecule. Virtually any protein or small molecule may be linked to Fc to generate an Fc fusion. Protein fusion partners may include, but are not limited to, the target-binding region of a receptor, an adhesion molecule, a ligand, an enzyme, a cytokine, a chemokine, or some other protein or protein domain. Small molecule fusion partners may include any therapeutic agent that directs the Fc fusion to a therapeutic target. Such targets may be any molecule, for example without limitation, an extracellular receptor that is implicated in disease.

The "hinge region," "hinge sequence", and variations thereof, as used herein, includes the meaning known in the art, which is illustrated in, for example, Janeway et al., ImmunoBiology: the immune system in health and disease, (Elsevier Science Ltd., NY) (4th ed., 1999); Bloom et al., *Protein Science* (1997), 6:407-415; Humphreys et al., *J. Immunol. Methods* (1997), 209:193-202.

The "immunoglobulin-like hinge region," "immunoglobulin-like hinge sequence," and variations thereof, as used herein, refer to the hinge region and hinge sequence of an immunoglobulin-like or an antibody-like molecule (e.g., immunoadhesins). In some embodiments, the immunoglobulin-like hinge region can be from or derived from any IgG1, IgG2, IgG3, or IgG4 subtype, or from IgA, IgE, IgD or IgM, including chimeric forms thereof, e.g., a chimeric IgG1/2 hinge region.

The term "vector," as used herein, is intended to refer to a nucleic acid molecule capable of transporting another nucleic acid to which it has been linked. One type of vector is a "plasmid," which refers to a circular double stranded DNA loop into which additional DNA segments may be ligated. Another type of vector is a phage vector. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "recombinant vectors"). In general, expression vectors of utility in recombinant DNA techniques are often in the form of plasmids. In the present specification, "plasmid" and "vector" may be used interchangeably as the plasmid is the most commonly used form of vector.

"Polynucleotide," or "nucleic acid molecule," which may be used interchangeably herein, refers to a polymeric, possibly isolated, form of nucleosides or nucleotides of at least 10 bases in length. The term includes single and double stranded forms. The nucleotides can be deoxyribonucleotides, ribonucleotides, modified nucleotides or bases, and/or their analogs, or any substrate that can be incorporated into a polymer by DNA or RNA polymerase, or by a synthetic reaction.

A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may be further modified after synthesis, such as by conjugation with a label. Other types of modifications include, for example, "caps", substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, ply-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid or semi-solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl, T-fluoro- or T-azido-ribose, carbocyclic sugar analogs, alpha-anomeric sugars, epimeric sugars such as arabinose, xyloses or lyxoses, pyranose sugars, furanose sugars, sedoheptuloses, acyclic analogs and abasic nucleoside analogs such as methyl riboside. One or more phosphodiester linkages may be replaced by alternative linking groups. These alternative linking groups include, but are not limited to, embodiments wherein phosphate is replaced by P(O)S ("thioate"), P(S)S ("dithioate"), "(O)NR$_2$ ("amidate"), P(O)R, P(O)OR", CO or CH$_2$ ("formacetal"), in which each R or R' is independently H or substituted or unsubstituted alkyl (1-20 C.) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

"Oligonucleotide," as used herein, generally refers to short, generally single stranded, generally synthetic polynucleotides that are generally, but not necessarily, less than about 200 nucleotides in length. The terms "oligonucleotide" and "polynucleotide" are not mutually exclusive. The description above for polynucleotides is equally and fully applicable to oligonucleotides.

A reference to a nucleotide sequence as used herein encompasses its complement unless otherwise specified. Thus, a reference to a nucleic acid having a particular sequence should be understood to encompass its complementary strand, with its complementary sequence, unless otherwise defined by context.

"Cell" or "cell line," as used herein, includes various types of cells that can be used to express a heterodimeric protein, a polypeptide or a nucleic acid of the invention, e.g., prokaryotic cells, eukaryotic cells, mammalian cells, rat cells, human cells.

The term "purify," and grammatical variations thereof, is used to mean the removal, whether completely or partially, of at least one impurity from a mixture containing the polypeptide and one or more impurities, which thereby improves the level of purity of the polypeptide in the composition (i.e., by decreasing the amount (ppm) of impurity(ies) in the composition). According to the present invention, purification is performed using at least one purification step that separates on the basis of the electrostatic state of one or more of an immunoglobulin-like hinge polypeptide or region, and a CH3 region. In certain embodiments, at least one purification step comprises or consists essentially of ion-exchange chromatography.

The terms "ion-exchange" and "ion-exchange chromatography" refer to a chromatographic process in which an ionizable solute of interest (e.g., a protein of interest in a mixture) interacts with an oppositely charged ligand linked (e.g., by covalent attachment) to a solid phase ion exchange material under appropriate conditions of pH and conductivity, such that the solute of interest interacts non-specifically with the charged compound more or less than the solute impurities or contaminants in the mixture. The contaminating solutes in the mixture can be washed from a column of the ion exchange material or are bound to or excluded from the resin, faster or slower than the solute of interest. "Ion-exchange chromatography" specifically includes cation exchange, anion exchange, and mixed mode chromatographies.

A "blocking" antibody or an "antagonist" antibody is one which inhibits or reduces biological activity of the antigen it binds. An "agonist antibody", as used herein, is an antibody which mimics at least one of the functional activities of a polypeptide of interest.

The term "immune effector cell" or "effector cell as used herein refers to a cell within the natural repertoire of cells in the human immune system which can be activated to affect the viability of a target cell. The viability of a target cell can include cell survival, proliferation, and/or ability to interact with other cells.

Reference to "about" a value or parameter herein includes (and describes) embodiments that are directed to that value or parameter per se. For example, description referring to "about X" includes description of "X." Numeric ranges are inclusive of the numbers defining the range.

It is understood that wherever embodiments are described herein with the language "comprising," otherwise analogous embodiments described in terms of "consisting of" and/or "consisting essentially of" are also provided.

Where aspects or embodiments of the invention are described in terms of a Markush group or other grouping of alternatives, the present invention encompasses not only the entire group listed as a whole, but each member of the group individually and all possible subgroups of the main group, but also the main group absent one or more of the group members. The present invention also envisages the explicit exclusion of one or more of any of the group members in the claimed invention.

Unless otherwise defined, all technical and scientific terms used herein have the same meaning as commonly understood by one of ordinary skill in the art to which this invention belongs. Exemplary methods and materials are described herein, although methods and materials similar or equivalent to those described herein can also be used in the practice or testing of the present invention. All publications and other references mentioned herein are incorporated by reference in their entirety. In case of conflict, the present specification, including definitions, will control. Although a number of documents are cited herein, this citation does not constitute an admission that any of these documents forms part of the common general knowledge in the art. Throughout this specification and claims, the word "comprise," or variations such as "comprises" or "comprising" will be understood to imply the inclusion of a stated integer or group of integers but not the exclusion of any other integer or group of integers. Unless otherwise required by context, singular terms shall include pluralities and plural terms shall include the singular. The materials, methods, and examples are illustrative only and not intended to be limiting.

Heteromultimeric Proteins

Except where indicated otherwise by context, the terms "first" polypeptide and "second" polypeptide, and variations thereof, are merely generic identifiers, and are not to be taken as identifying a specific or a particular polypeptide or component of heteromultimeric, e.g. heterodimeric proteins of the invention.

In one aspect, this invention provides a heteromultimeric protein, e.g., a heterodimeric protein, comprising a hinge region, wherein the hinge region comprises a first immunoglobulin-like hinge polypeptide and a second immunoglobulin-like hinge polypeptide that interact together to form a hinge interface engineered to promote heterodimer formation, i.e., the first and second immunoglobulin-like hinge polypeptides tend to interact to form a heterodimeric hinge region faster and/or with greater affinity or stability than do first or second immunoglobulin-like hinge polypeptides interact with like hinge (i.e., first with first or second with second) polypeptides to form homodimeric hinge regions. In certain embodiments of the invention, one or more charged amino acids are present or are engineered within the hinge interface so that they interact with one or more other amino acids within the hinge interface to electrostatically favor heterodimer formation over homodimer formation.

In some embodiments, the hinge region is an IgG, IgA, IgE, IgD, or IgM hinge region. In some embodiments, the hinge region is a human or non-human mammal IgG region. In some embodiments, the hinge region is a human IgG1, IgG2, IgG3, or IgG4 hinge region, or chimeric versions thereof.

In some embodiments or the heterodimeric protein of the invention, the first hinge polypeptide comprises one or more amino acid modification relative to a wild-type IgG hinge region, wherein the wild-type amino acid is replaced with an amino acid having an opposite charge to the corresponding amino acid in the second hinge polypeptide. In some embodiments or the heterodimeric protein of the invention, the first hinge polypeptide comprises one or more amino acid modification relative to a wild-type IgG hinge region; and the second hinge polypeptide comprises at least one amino acid modification relative to a wild-type IgG hinge region in proximity to, juxtaposed or at the same position as the amino acid modification in the first hinge polypeptide, wherein the wild-type amino acid in the second hinge polypeptide is replaced with an amino acid having an opposite charge to the corresponding amino acid in the first hinge polypeptide. As one of skill in the art will readily appreciate, hinge polypeptides form three-dimensional structures and thus amino acids in the hinge region need not necessarily be identical or contiguous in linear sequence in order to be in proximity to or to juxtapose with one or more other amino acids in the hinge region in order to "interact" in a non-covalent fashion, such as by electrostatic charge.

In another aspect, this invention also provides a heterodimeric protein comprising a hinge region and a CH3 region. In some embodiments, the CH3 region is engineered to destabilize homodimer formation and promote heterodimer formation. In some embodiments, the engineered CH3 region is not electrostatically unfavorable to homodimer formation. In some embodiments, both the hinge region and the CH3 region are engineered to electrostatically favor heterodimer formation over homodimer.

In another aspect, this invention also provides a heteromultimeric, e.g., a heterodimeric Fc fusion protein comprising a hinge region, wherein the hinge region comprises a first immunoglobulin hinge polypeptide and a second immunoglobulin hinge polypeptide that meet interact together to form a hinge interface engineered to promote heterodimeric Fc fusion protein formation, wherein one or more charged amino acids within the hinge interface electrostatically promote heterodimeric Fc fusion protein formation. Examples of heterodimeric Fc fusion proteins include, without limitation, bispecific antibodies, monospecific antibodies, and multispecific antibodies. In some embodiments, the heterodimeric Fc fusion protein is an antibody. In other embodiments, the heterodimeric Fc fusion protein is not an antibody.

In another aspect, this invention also provides a bispecific antibody comprising a hinge region, wherein the hinge region comprises a first immunoglobulin hinge polypeptide and a second immunoglobulin hinge polypeptide that meet interact together to form a hinge interface engineered to promote bispecific antibody formation, wherein one or more charged amino acids within the hinge interface electrostatically promote bispecific antibody formation.

In another aspect, this invention also provides a bispecific antibody or Fc fusion heterodimeric protein comprising a hinge region and a CH3 region, wherein the hinge region and/or the CH3 region are engineered to favor heterodimer formation over homodimer. In some embodiments, the hinge region is engineered to electrostatically favor heterodimer formation over homodimer. In some embodiments, the engineered CH3 region is not electrostatically unfavorable to homodimer formation.

In another aspect, this invention also provides a bispecific antibody or Fc fusion heterodimeric protein comprising a hinge region and a CH3 region, wherein the CH3 region is engineered to favor heterodimer formation over homodimer. In some embodiments, the engineered CH3 region is not electrostatically unfavorable to homodimer formation.

In some embodiments, a heterodimeric protein of the invention may comprise two antibody fragments, such as, for example, an Fc or Fc fusion polypeptide. An Fc fusion polypeptide generally comprises an Fc sequence (or fragment thereof) fused to a heterologous polypeptide sequence, such as, for example without limitation, an antigen binding domain. One exemplary Fc fusion polypeptide is a receptor extracellular domain (ECD) fused to an immunoglobulin Fc sequence (e.g., Flt receptor ECD fused to an IgG2 Fc).

In certain embodiments, the amino acid modification(s) in a hinge region (for example without limitation, a human IgG4, IgG2 or IgG1 hinge region) occur(s) at any one or more residues of the hinge region. In some embodiments, the amino acid modification(s) occur(s) at one or more the following positions of a hinge region: 216, 217, 218, 219, 220, 221, 222, 223, 224, 225, 226, 227, 228, 229 and 230.

In certain embodiments, the amino acid modification(s) in a CH3 region (for example without limitation, a human IgG4, IgG2 or IgG1 CH3 region) occur(s) at any one or more residues of the CH3 region. In some embodiments, the amino acid modification(s) occur(s) at one or more the following positions of a CH3 region: 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446 and 447.

In some embodiments, the amino acid modification(s) in the hinge region (e.g., human IgG1 hinge region) occur(s) at a position selected from 219, 221, 227 and 228. In some embodiments, the amino acid modification(s) in the hinge region (e.g., human IgG1 hinge region) occur(s) at a position selected from 221 and 228. In some embodiments, the amino acid modification(s) in the CH3 region (e.g., human IgG1 CH3 region) occur(s) at a position selected from 349, 368, 405, and 409. In some embodiments, the amino acid modification(s) in the CH3 region includes K409R, L368D, and/or L368E. In some embodiments, the amino acid modifications occur at positions 221 and 228 (e.g., (D221R or D221E) and (P228R or P228E)) in the hinge region and at position 409 or 368 (e.g., K409R or L368E) in the CH3 region of human IgG1.

In some embodiments, the amino acid modification in the hinge region (e.g., human IgG2 hinge region) is located at a position selected from 222, 223, 225, 227 and 228. In some embodiments, the amino acid modification in the hinge region (e.g., human IgG2 hinge region) is located at a position selected from 223, 225 and 228. In some embodiments, the amino acid modification in the CH3 region (e.g., human IgG2 CH3 region) is located at a position selected from 349, 368, 405, and 409. In some embodiments, the amino acid modification in the CH3 region (e.g., human IgG2 CH3 region) is located at a position selected from 368 and 409. In some embodiments, the amino acid modification(s) in the CH3 region includes K409R, L368D, and/or L368E. In some embodiments, the amino acid modifications occur at positions 223, 225, and 228 (e.g., (C223E or C223R), (E225E or E225R), and (P228E or P228R)) in the hinge region and at position 409 or 368 (e.g., K409R or L368E) in the CH3 region of human IgG2.

In some embodiments, the amino acid modification in the hinge region (e.g., human IgG4 hinge region) is located at a position selected from 217 and 228. In some embodiments, the amino acid modification(s) in the hinge region includes a modification at position 228.

In another aspect, the invention also provides a polypeptide comprising a hinge region engineered to electrostatically favor heterodimer over homodimer formation. In some embodiments, a polypeptide of the invention comprises a heavy chain constant domain and a light chain constant domain. In some embodiments, a polypeptide of the invention comprises one or more modified amino acids in the Fc region (e.g., hinge region or hinge and CH3 region), which is capable of electrostatically promoting heterodimer formation. In one embodiment, a polypeptide of the invention does not comprise a modification in the CH3 region. In some embodiments, a portion (but not all) of the Fc sequence is missing in an antibody of the invention. In some of these embodiments, the missing Fc sequence is at least a portion of, in some case the entire, CH2 and/or CH3 domain.

In some embodiments, a heterodimeric hinge and/or CH3 region comprise(s) any of the substitution combinations shown in rows 1-67 Table 1. In some embodiments, a first hinge and/or CH3 polypeptide comprise(s) any of the substitution combinations shown in Table 1. In some embodiments, a second hinge and/or CH3 polypeptide comprise(s) any of the substitution combinations shown in Table 1. In Table 1, positions are shown in bold (i.e., hinge positions 221, 223, 225 and 228 and CH3 positions 368 and 409). Rows 1-15 correspond to substitutions made in an IgG1 hinge and/or IgG2 CH3. Rows 16-63 correspond to substitutions made in an IgG2 hinge and/or CH3. Rows 64-67 correspond to substitutions made in an IgG4 hinge. E/D indicates a substitution at position 368 in a CH3 polypeptide with either Glu or Asp.

TABLE 1

|  | Substitutions in first hinge-CH3 polypeptide | | | | | | Substitutions in second hinge-CH3 polypeptide | | | | | |
| --- | --- | --- | --- | --- | --- | --- | --- | --- | --- | --- | --- | --- |
|  | 221 | 223 | 225 | 228 | 368 | 409 | 221 | 223 | 225 | 228 | 368 | 409 |
| 1. | R |  |  | R |  |  | E |  |  | E |  |  |
| 2. | R |  |  | E |  |  | E |  |  | R |  |  |
| 3. | R |  |  | R |  | R | E |  |  | E |  | R |
| 4. | R |  |  | E |  | R | E |  |  | R |  | R |
| 5. | R |  |  | R | E/D |  | E |  |  | E | E/D |  |
| 6. | R |  |  | E | E/D |  | E |  |  | R | E/D |  |
| 7. | R |  |  | R | E/D |  | E |  |  | E |  | R |
| 8. | R |  |  | E | E/D |  | E |  |  | R |  | R |
| 9. | R |  |  | R |  | R | E |  |  | E | E |  |
| 10. | R |  |  | E |  | R | E |  |  | R | E |  |
| 11. | R |  |  | R |  | E | E |  |  | E | R |  |
| 12. | R |  |  | E |  | E | E |  |  | R | R |  |
| 13. |  |  |  |  |  | R |  |  |  |  |  | R |
| 14. |  |  |  |  | E/D |  |  |  |  |  | E/D |  |
| 15. |  |  |  |  | E/D |  |  |  |  |  |  | R |
| 16. |  | D | E | K |  |  |  | R | R | D |  |  |
| 17. |  | D | E | K |  | R |  | R | R | D |  | R |
| 18. |  | D | E | K |  | R |  | R | R | D | E/D |  |
| 19. |  | D | E | K | E/D |  |  | R | R | D |  | R |
| 20. |  | D | E | K |  |  |  | R | R | D |  |  |
| 21. |  | D | E | E |  |  |  | R | K | R |  |  |
| 22. |  | D | E | E |  | R |  | R | K | R |  | R |
| 23. |  | D | E | E |  | R |  | R | K | R | E/D |  |
| 24. |  | D | E | E | E/D |  |  | R | K | R |  | R |
| 25. |  | D | E | E | E/D |  |  | R | K | R | E/D |  |
| 26. |  | E | R | E |  |  |  | R | E | K |  |  |
| 27. |  | E | R | E |  | R |  | R | E | K |  | R |
| 28. |  | E | R | E |  | R |  | R | E | K | E/D |  |
| 29. |  | E | R | E | E/D |  |  | R | E | K |  | R |
| 30. |  | E | R | E | E/D |  |  | R | E | K | E/D |  |
| 31. |  | E | E | R |  |  |  | R | K | E |  |  |
| 32. |  | E | E | R |  | R |  | R | K | E |  | R |
| 33. |  | E | E | R |  | R |  | R | K | E | E/D |  |
| 34. |  | E | E | R | E/D |  |  | R | K | E |  | R |
| 35. |  | E | E | R | E/D |  |  | R | K | E | E/D |  |
| 36. |  | D | R | E |  |  |  | K | E | R |  |  |
| 37. |  | D | R | E |  | R |  | K | E | R |  | R |
| 38. |  | D | R | E |  | R |  | K | E | R | E/D |  |
| 39. |  | D | R | E | E/D |  |  | K | E | R |  | R |
| 40. |  | D | R | E | E/D |  |  | K | E | R | E/D |  |
| 41. |  | D | E | R |  |  |  | R | R | E |  |  |
| 42. |  | D | E | R |  | R |  | R | R | E |  | R |
| 43. |  | D | E | R |  | R |  | R | R | E | E/D |  |
| 44. |  | D | E | R | E/D |  |  | R | R | E |  | R |
| 45. |  | D | E | R | E/D |  |  | R | R | E | E/D |  |
| 46. |  | E | E | E |  |  |  | R | R | R |  |  |
| 47. |  | E | E | E |  | R |  | R | R | R |  | R |
| 48. |  | E | E | E |  | R |  | R | R | R | E/D |  |
| 49. |  | E | E | E | E/D |  |  | R | R | R |  | R |
| 50. |  | E | E | E | E/D |  |  | R | R | R | E/D |  |
| 51. |  | E | K | E |  |  |  | R | E | R |  |  |
| 52. |  | E | K | E |  | R |  | R | E | R |  | R |
| 53. |  | E | K | E |  | R |  | R | E | R | E/D |  |
| 54. |  | E | K | E | E/D |  |  | R | E | R |  | R |
| 55. |  | E | K | E | E/D |  |  | R | E | R | E/D |  |
| 56. |  | D | E | E |  |  |  | R | K | R |  |  |
| 57. |  | D | E | E |  | R |  | R | K | R |  | R |
| 58. |  | D | E | E |  | R |  | R | K | R | E/D |  |
| 59. |  | D | E | E | E/D |  |  | R | K | R |  | R |
| 60. |  | D | E | E | E/D |  |  | R | K | R | E/D |  |
| 61. |  |  |  |  |  | R |  |  |  |  |  | R |
| 62. |  |  |  |  | E/D |  |  |  |  |  | E/D |  |
| 63. |  |  |  |  | E/D |  |  |  |  |  |  | R |

TABLE 1-continued

| | Substitutions in first hinge-CH3 polypeptide | | | | | | Substitutions in second hinge-CH3 polypeptide | | | | | |
|---|---|---|---|---|---|---|---|---|---|---|---|---|
| | 221 | 223 | 225 | 228 | 368 | 409 | 221 | 223 | 225 | 228 | 368 | 409 |
| 64. | | | | R | | | | | | E | | |
| 65. | | | | K | | | | | | E | | |
| 66. | | | | R | | | | | | D | | |
| 67. | | | | K | | | | | | D | | |

In another aspect of the invention, the heterodimeric protein (e.g., bispecific antibody) as described herein comprises a full-length human antibody, wherein a first antibody variable domain of the heterodimeric protein is capable of recruiting the activity of a human immune effector cell by specifically binding to an effector antigen located on the human immune effector cell, and wherein a second antibody variable domain of the heterodimeric protein is capable of specifically binding to a target antigen. In some embodiments, the human antibody has an IgG1, IgG2, IgG3, or IgG4 isotype. In some embodiments, the heterodimeric protein comprises an immunologically inert Fc region.

The human immune effector cell can be any of a variety of immune effector cells known in the art. For example, the immune effector cell can be a member of the human lymphoid cell lineage, including, but not limited to, a T cell (e.g., a cytotoxic T cell), a B cell, and a natural killer (NK) cell. The immune effector cell can also be, for example without limitation, a member of the human myeloid lineage, including, but not limited to, a monocyte, a neutrophilic granulocyte, and a dendritic cell. Such immune effector cells may have either a cytotoxic or an apoptotic effect on a target cell or other desired effect upon activation by binding of an effector antigen.

The effector antigen is an antigen (e.g., a protein or a polypeptide) that is expressed on the human immune effector cell. Examples of effector antigens that can be bound by the heterodimeric protein (e.g., a heterodimeric protein or a bispecific antibody) include, but are not limited to, human CD3 (or CD3 (Cluster of Differentiation) complex), CD16, NKG2D, NKp46, CD2, CD28, CD25, CD64, and CD89.

The target cell can be a cell that is native or foreign to humans. In a native target cell, the cell may have been transformed to be a malignant cell or pathologically modified (e.g., a native target cell infected with a virus, a plasmodium, or a bacterium). In a foreign target cell, the cell is an invading pathogen, such as a bacterium, a plasmodium, or a virus.

The target antigen is expressed on a target cell in a diseased condition (e.g., an inflammatory disease, a proliferative disease (e.g., cancer), an immunological disorder, a neurological disease, a neurodegenerative disease, an autoimmune disease, an infectious disease (e.g., a viral infection or a parasitic infection), an allergic reaction, a graft-versus-host disease or a host-versus-graft disease). A target antigen is not effector antigen. Examples of the target antigens include, but are not limited to, EpCAM (Epithelial Cell Adhesion Molecule), CCR5 (Chemokine Receptor type 5), CD19, HER (Human Epidermal Growth Factor Receptor)-2/neu, HER-3, HER-4, EGFR (Epidermal Growth Factor Receptor), PSMA, CEA, MUC-1 (Mucin), MUC2, MUC3, MUC4, MUC5AC, MUC5B, MUC7, CIhCG, Lewis-Y, CD20, CD33, CD30, ganglioside GD3, 9-O-Acetyl-GD3, GM2, Globo H, fucosyl GM1, Poly SA, GD2, Carboanhydrase IX (MN/CA IX), CD44v6, Shh (Sonic Hedgehog), Wue-1, Plasma Cell Antigen, (membrane-bound) IgE, MCSP (Melanoma Chondroitin Sulfate Proteoglycan), CCR8, TNF-alpha precursor, STEAP, mesothelin, A33 Antigen, PSCA (Prostate Stem Cell Antigen), Ly-6; desmoglein 4, E-cadherin neoepitope, Fetal Acetylcholine Receptor, CD25, CA19-9 marker, CA-125 marker and MIS (Muellerian Inhibitory Substance) Receptor type II, sTn (sialylated Tn antigen; TAG-72), FAP (fibroblast activation antigen), endosialin, EGFRvIII, LG, SAS and CD63.

In some embodiments, the heterodimeric protein (e.g., bispecific antibody) as described herein comprises a full-length human antibody, wherein a first antibody variable domain of the heterodimeric protein is capable of recruiting the activity of a human immune effector cell by specifically binding to an effector antigen (e.g., CD3 antigen) located on the human immune effector cell, wherein a second antibody variable domain of the heterodimeric protein is capable of specifically binding to a target antigen (e.g., CD20 antigen or EpCAM), wherein both the first and the second antibody variable domains of the heterodimeric protein comprise amino acid modifications at positions 221 and 228 (e.g., (D221R or D221E) and (P228R or P228E)) in the hinge region and at position 409 or 368 (e.g., K409R or L368E) in the CH3 region.

In some embodiments, the heterodimeric protein (e.g., bispecific antibody) as described herein comprises a full-length human antibody, wherein a first antibody variable domain of the heterodimeric protein is capable of recruiting the activity of a human immune effector cell by specifically binding to an effector antigen (e.g., CD3 antigen) located on the human immune effector cell, wherein a second antibody variable domain of the heterodimeric protein is capable of specifically binding to a target antigen (e.g., CD20 antigen or EpCAM), wherein both the first and the second antibody variable domains of the heterodimeric protein comprise amino acid modifications at positions 223, 225, and 228 (e.g., (C223E or C223R), (E225E or E225R) and (P228E or P228R)) in the hinge region and at position 409 or 368 (e.g., K409R or L368E) in the CH3 region.

In another aspect of the invention, a heterodimeric protein disclosed herein may be deimmunized to reduce immunogenicity upon administration to a subject using known techniques such as those described, e.g., in PCT Publication WO98/52976 and WO00/34317.

In other embodiments, a heterodimeric Fc fusion protein may be modified or derivatized, such as by making a fusion antibody or immunoadhesin that comprises all or a portion of the heterodimeric polypeptide, e.g., bispecific antibody disclosed herein, linked to another polypeptide or molecular agent. Heteromultimeric, e.g. heterodimeric polypeptides disclosed herein (e.g., bispecific antibodies) may be modified or derivatized, for example, to extend in vivo half-lives, by producing more stable fusion molecules and/or by treatment with biocompatible polymers such as polyethylene glycol (PEG), commonly referred to as "pegylation," or by any of a number of other engineering methods well known in the art.

A heterodimeric Fc fusion protein may be derivatized with a chemical group, including but not limited to polyethylene glycol (PEG), a methyl or ethyl group, an ester, a carbohydrate group and the like, using well known techniques. These chemical groups (and others like them which have been used to stability therapeutic compounds in vivo) are useful to improve the biological characteristics of the heterodimeric polypeptide, e.g., to increase serum half-life and bioactivity.

A heterodimeric Fc fusion protein may also be labeled using any of a multitude of methods known in the art. As used herein, the terms "label" or "labeled" refers to incorporation of another molecule in the antibody. In one embodiment, the label is a detectable marker, e.g., incorporation of a radiolabeled amino acid or attachment to a polypeptide of biotinyl moieties that can be detected by marked avidin (e.g., streptavidin containing a fluorescent marker or enzymatic activity that can be detected by optical or colorimetric methods). In another embodiment, the label or marker can be therapeutic, e.g., a drug conjugate or toxin. Various methods of labeling polypeptides and glycoproteins are known in the art and may be used. Examples of labels for polypeptides include, but are not limited to: radioisotopes or radionuclides (e.g., 3H, 14C, 15N, 35S, 90Y, 99Tc, 111In, 125I, 131I), fluorescent labels (e.g., FITC, rhodamine, lanthanide phosphors), enzymatic labels (e.g., horseradish peroxidase, β-galactosidase, luciferase, alkaline phosphatase), chemiluminescent markers, biotinyl groups, predetermined polypeptide epitopes recognized by a secondary reporter (e.g., leucine zipper pair sequences, binding sites for secondary antibodies, metal binding domains, epitope tags), magnetic agents, such as gadolinium chelates, toxins such as pertussis toxin, taxol, cytochalasin B, gramicidin D, ethidium bromide, emetine, mitomycin, etoposide, tenoposide, vincristine, vinblastine, colchicine, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. In some embodiments, labels are attached by spacer arms of various lengths to reduce potential steric hindrance.

Nucleic Acids, Vectors and Cells

The present invention also encompasses nucleic acid molecules and sequences encoding polypeptides disclosed herein that comprise modified immunoglobulin-like hinge or Fc related sequences. In some embodiments, different nucleic acid molecules encode one or more chains or portions of the heterodimeric protein, e.g., bispecific antibody disclosed herein. In other embodiments, the same nucleic acid molecule encodes a heterodimeric protein disclosed herein.

In one aspect, the present invention provides a nucleic acid sequence encoding one of the chains of a heterodimeric protein disclosed herein, or portion thereof as described above. Nucleic acid molecules of the invention include nucleic acids that hybridize under highly stringent conditions, such as those at least about 70%, 75%, 80%, 85%, 90%, 95%, 97%, 98% or 99% or more identical to a nucleic acid sequence of the invention.

The term "percent sequence identity" in the context of nucleic acid sequences means the residues in two sequences that are the same when aligned for maximum correspondence. The length of sequence identity comparison may be over a stretch of at least about nine nucleotides, usually at least about 18 nucleotides, more usually at least about 24 nucleotides, typically at least about 28 nucleotides, more typically at least about 32 nucleotides, and preferably at least about 36, 48 or more nucleotides. There are a number of different algorithms known in the art which can be used to measure nucleotide sequence identity. For instance, polynucleotide sequences can be compared using FASTA, Gap or Bestfit, which are programs in Wisconsin Package Version 10.0, Genetics Computer Group (GCG), Madison, Wis. FASTA, which includes, e.g., the programs FASTA2 and FASTA3, provides alignments and percent sequence identity of the regions of the best overlap between the query and search sequences (Pearson, *Methods Enzymol.* 183:63-98 (1990); Pearson, *Methods Mol. Biol.* 132:185-219 (2000); Pearson, *Methods Enzymol.* 266:227-258 (1996); Pearson, *J. Mol. Biol.* 276:71-84 (1998); incorporated herein by reference). Unless otherwise specified, default parameters for a particular program or algorithm are used. For instance, percent sequence identity between nucleic acid sequences can be determined using FASTA with its default parameters (a word size of 6 and the NOPAM factor for the scoring matrix) or using Gap with its default parameters as provided in GCG Version 6.1, incorporated herein by reference.

In a further aspect, the present invention provides a vector comprising a nucleic acid sequence encoding one or more of the chains or portions of the heteromultimeric or heterodimeric protein disclosed herein, or portion thereof as described herein.

In a further aspect, the present invention provides a vector suitable for expressing one or more of the chains or portions of the heterodimeric protein disclosed herein, or portion thereof as described herein.

In another embodiment, a nucleic acid molecule of the invention is used as a probe or PCR primer for a specific amino acid sequence, e.g., a specific antibody sequence such as in hinge and constant heavy domain sequences. For instance, the nucleic acid can be used as a probe in diagnostic methods or as a PCR primer to amplify regions of DNA that could be used, inter alia, to isolate additional nucleic acid molecules encoding useful sequences. In some embodiments, the nucleic acid molecules are oligonucleotides. In some embodiments, the oligonucleotides are from hinge and constant domain regions of the heavy and light chains of an antibody of interest. In some embodiments, the oligonucleotides encode all or a part of one or more of the modified hinge regions of the heterodimeric polypeptide, e.g., bispecific antibodies or fragments thereof of the invention as described herein.

Recombinant expression vectors of the invention may, in some embodiments, carry regulatory sequences that control the expression of antibody chain genes in a host cell. It will be appreciated by those skilled in the art that the design of the expression vector, including the selection of regulatory sequences may depend on such factors as the choice of the host cell to be transformed, the level of expression of protein desired, etc. Preferred regulatory sequences for mammalian host cell expression include viral elements that direct high levels of protein expression in mammalian cells, such as promoters and/or enhancers derived from retroviral LTRs, cytomegalovirus (CMV) (such as the CMV promoter/enhancer), Simian Virus 40 (SV40) (such as the SV40 promoter/enhancer), adenovirus, (e.g., the adenovirus major late promoter (AdMLP)), polyoma and strong mammalian promoters such as native immunoglobulin and actin promoters. For further description of viral regulatory elements, and sequences thereof, see e.g., U.S. Pat. Nos. 5,168,062, 4,510,245 and 4,968,615. Methods for expressing antibodies in plants, including a description of promoters and vectors, as well as transformation of plants is known in the art. See, e.g. U.S. Pat. No. 6,517,529. Methods of expressing polypeptides in bacterial cells or fungal cells, e.g., yeast cells, are also well known in the art.

In addition to the antibody chain genes and regulatory sequences, the recombinant expression vectors of the invention may carry additional sequences, such as sequences that regulate replication of the vector in host cells (e.g., origins of replication) and selectable marker genes. The selectable marker gene facilitates selection of host cells into which the vector has been introduced (see e.g., U.S. Pat. Nos. 4,399, 216, 4,634,665 and 5,179,017). For example, typically the selectable marker gene confers resistance to drugs, such as G418, hygromycin or methotrexate, on a host cell into which the vector has been introduced. For example, selectable marker genes include the dihydrofolate reductase (DHFR) gene (for use in dhfr⁻ host cells with methotrexate selection/amplification), the neo gene (for G418 selection), and the glutamate synthetase gene.

The term "expression control sequence" as used herein means polynucleotide sequences that are necessary to effect the expression and processing of coding sequences to which they are ligated. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (i.e., Kozak consensus sequence); sequences that enhance protein stability; and when desired, sequences that enhance protein secretion. The nature of such control sequences differs depending upon the host organism; in prokaryotes, such control sequences generally include promoter, ribosomal binding site, and transcription termination sequence; in eukaryotes, generally, such control sequences include promoters and transcription termination sequence. The term "control sequences" is intended to include, at a minimum, all components whose presence is essential for expression and processing, and can also include additional components whose presence is advantageous, for example, leader sequences and fusion partner sequences.

Methods of Producing Heteromultimeric Proteins

In one aspect, this invention provides a strategy for enhancing the formation of a desired heteromultimeric or heterodimeric protein, e.g., an Fc fusion protein, by altering or engineering an interface between a first and a second immunoglobulin-like Fc region (e.g., a hinge region, a CH3 region, or a hinge region and a CH3 region). In some embodiments, one or more residues that make up the hinge interface are replaced with charged residues such that the electrostatic interactions between these charged residues electrostatically favor heterodimer formation over homodimer formation. In further embodiments, one or more residues that make up the CH3 interface are further replaced with charged residues such that the interactions between the CH3 interface further promotes heterodimer formation over homodimer formation. In some embodiments, the engineered CH3 interface electrostatically favor heterodimer formation over homodimer formation. In some embodiments, the engineered CH3 interface sterically favor heterodimer formation over homodimer formation. In other embodiments, the engineered CH3 interface destabilizes homodimer formation but is not electrostatically unfavorable to homodimer formation.

In some embodiments, the formation of the heterodimeric protein comprising one or more amino acid modification in the first hinge region and the first CH3 region disclosed herein is substantially increased in comparison to the wild-type heterodimeric protein without such modifications. In some embodiments, the formation of the heterodimeric protein comprising one or more amino acid modification in the first hinge region and the first CH3 region is at least about any of 51%, 55%, 60%, 65%, 70%, 75%, 80%, 85%, 90%, 95%, 97%, 99%, or 100% in comparison to the wild-type heterodimeric protein without such modifications. In some embodiments, the amino acid modification(s) in the hinge region occur(s) at a position selected from 217, 218, 219, 221, 222, 223, 224, 225, 226, 227, and 228. In some embodiments, the amino acid modification(s) in the CH3 region occur(s) at a position selected from 349, 368, 405, and 409.

In some embodiments, the formation of the heterodimeric protein comprising one or more amino acid modification in both the first and second hinge regions and both the first and second CH3 regions disclosed herein is substantially increased in comparison to the wild-type heterodimeric protein without such modifications. In some embodiments, the formation of the heterodimeric protein comprising one or more amino acid modification in both the first and second hinge regions and both the first and second CH3 regions is at least about any of 51%, 55%, 60%, 65%, 70%, 75%, 80%, 85%, 90%, 95%, 97%, 99%, or 100% in comparison to the wild-type heterodimeric protein without such modifications. In some embodiments, the amino acid modification(s) in the hinge region occur(s) at a position selected from 217, 218, 219, 221, 222, 223, 224, 225, 226, 227, and 228. In some embodiments, the amino acid modification(s) in the CH3 region occur(s) at a position selected from 349, 368, 405, and 409.

In another aspect, this invention also provides methods of producing a heteromultimeric protein, e.g., a heterodimeric protein of the invention.

In some embodiments, the method comprising the steps of: a) culturing a host cell comprising a nucleic acid molecule encoding a first polypeptide comprising a modified Fc region (e.g., hinge region and/or CH3 region) and the same or a different nucleic acid molecule encoding a second polypeptide comprising a modified Fc region (e.g., hinge region and/or CH3 region), wherein the cultured host cell expresses the first and second polypeptides; and b) recovering the heteromultimeric, e.g., heterodimeric protein from the host cell culture. In some embodiments, the first polypeptide and second polypeptides are two different Fc fusion polypeptides. In some embodiments, the first polypeptide and second polypeptides are two different antibody heavy chains. In some embodiments, the host cell further expresses another polypeptide, e.g., a light chain. In some embodiments, the light chain can associate with both heavy chains. Methods of coexpressing two different heavy chains with a single light chain are described in detail in, e.g., Example 3 below.

In some embodiments, the method comprising the steps of: a) expressing the first polypeptide in a first host cell; b) expressing the second polypeptide in a second host cell; c) isolating the first polypeptide of step a) and the second polypeptide of step b); and d) incubating the two polypeptides of step c) and the isolated polypeptide of step c) under a condition suitable for multimer formation, e.g., dimerization, to produce the heteromultimeric, e.g., heterodimeric protein. In some embodiments, the molecules or antibodies may be mixed in a saline solution containing a suitable reducing agent (e.g., glutathione). Any suitable saline solution and appropriate pH may be used, e.g., one that comprises Dulbecco's phosphate buffered saline (D-PBS). In some embodiments, the first and/or second host cell further expresses another polypeptide, e.g., a light chain.

The skilled artisan can readily determine, using well-known techniques, the relative amounts of molecules or antibodies to use according to the methods disclosed herein.

In the methods disclosed herein, incubations may be performed across a range of temperatures. Such temperatures will be recognized by those skilled in the art and will include, for example, incubation temperatures at which deleterious physical changes such as denaturation or decomposition do not occur in the mixed molecules or antibodies. In certain embodiments, the incubations are performed at 37° C.

Any of a number of host cells may be used in methods of the invention. Such cells are known in the art (some of which are described herein) or can be determined empirically with respect to suitability for use in methods of the invention using routine techniques known in the art. In certain embodiments, the host cell is prokaryotic. In some embodiments, a host cell is a gram-negative bacterial cell. In other embodiments, a host cell is *E. coli*. In some embodiments, the *E. coli* is of a strain deficient in endogenous protease activities. In some embodiments, the genotype of an *E. coli* host cell lacks degP and prc genes and harbors a mutant spr gene. In other embodiments of the invention, the host cell is mammalian, for example, a Chinese Hamster Ovary (CHO) cell.

In some embodiments, methods of the invention further comprise expressing in a host cell a polynucleotide or recombinant vector encoding a molecule the expression of which in the host cell enhances yield of a bispecific antibody or a heterodimeric protein of the invention. For example, such molecule can be a chaperone protein. In one embodiment, said molecule is a prokaryotic polypeptide selected from the group consisting of DsbA, DsbC, DsbG and FkpA. In some embodiments of these methods, the polynucleotide encodes both DsbA and DsbC.

Non-Hybridoma Host Cells and Methods of Recombinantly Producing Protein

In one aspect, the present invention provides recombinant host cells allowing the recombinant expression of the antibodies of the invention or portions thereof. Antibodies produced by such recombinant expression in such recombinant host cells are referred to herein as "recombinant antibodies". The present invention also provides progeny cells of such host cells, and antibodies produced by same. The term "recombinant host cell" (or simply "host cell"), as used herein, means a cell into which a recombinant expression vector has been introduced. It should be understood that "recombinant host cell" and "host cell" mean not only the particular subject cell but also the progeny of such a cell. Because certain modifications may occur in succeeding generations due to either mutation or environmental influences, such progeny may not, in fact, be identical to the parent cell, but are still included within the scope of the term "host cell" as used herein. Such cell may comprise a vector according to the invention as described above.

In another aspect, the present invention provides a method for making an antibody or portion thereof as described above. According to one embodiment, said method comprises culturing a cell transfected or transformed with a vector as described above, and retrieving said antibody or portion thereof. Nucleic acid molecules encoding antibodies and vectors comprising these nucleic acid molecules can be used for transfection of a suitable mammalian, plant, bacterial or yeast host cell. Transformation can be by any known method for introducing polynucleotides into a host cell. Methods for introduction of heterologous polynucleotides into mammalian cells are well known in the art and include dextran-mediated transfection, calcium phosphate precipitation, polybrene-mediated transfection, protoplast fusion, electroporation, encapsulation of the polynucleotide(s) in liposomes, and direct microinjection of the DNA into nuclei. In addition, nucleic acid molecules may be introduced into mammalian cells by viral vectors. Methods of transforming cells are well known in the art. See, e.g., U.S. Pat. Nos. 4,399,216, 4,912,040, 4,740,461, and 4,959,455. Methods of transforming plant cells are well known in the art, including, e.g., *Agrobacterium*-mediated transformation, biolistic transformation, direct injection, electroporation and viral transformation. Methods of transforming bacterial and yeast cells are also well known in the art.

Mammalian cell lines available as hosts for expression are well known in the art and include many immortalized cell lines available from the American Type Culture Collection (ATCC). These include, inter alia, Chinese hamster ovary (CHO) cells, NS0 cells, SP2 cells, HEK-293T cells, 293 Freestyle cells (Invitrogen), NIH-3T3 cells, HeLa cells, baby hamster kidney (BHK) cells, African green monkey kidney cells (COS), human hepatocellular carcinoma cells (e.g., Hep G2), A549 cells, and a number of other cell lines. Cell lines of particular preference are selected through determining which cell lines have high expression levels. Other cell lines that may be used are insect cell lines, such as Sf9 or Sf21 cells. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods. Suitable plant host cells may include, e.g., *Nicotiana, Arabidopsis*, duckweed, corn, wheat, potato, etc. Suitable bacterial host cells may include, e.g., *E. coli* and *Streptomyces* species. Suitable yeast host cells may include, e.g., *Schizosaccharomyces pombe, Saccharomyces cerevisiae* and *Pichia pastoris*.

Expression of polypeptides of the invention or portions thereof from production cell lines can be enhanced using a number of known techniques. For example, the glutamine synthetase gene expression system (the GS system) is a common approach for enhancing expression under certain conditions. The GS system is discussed in whole or part in connection with EP patents 0 216 846, 0 256 055, 0 323 997 and 0 338 841.

It is likely that polypeptides comprising Fc polypeptides or Fc regions and immunoglobulin-like hinge polypeptides, such as, e.g., antibodies, as expressed by different cell lines or in transgenic animals, will differ from each other in their glycosylation patterns. All such "glycoforms" of polypeptides of the invention, including all heterodimers of polypeptides comprising immunoglobulin-like hinge sequences, bispecific polypeptides, antibodies and the like, are considered to be part of the instant invention, regardless of their glycosylation state, and more generally, regardless of the presence or absence of any post-translational modification(s).

Methods of Purifying Heteromultimeric Proteins

In another aspect, the invention provides a method of purifying heterodimeric proteins on the basis of the electrostatic state (e.g., electric charge difference) of one or more of an immunoglobulin-like hinge polypeptide or region, and/or a CH3 region by chromatography. Disclosed herein are chromatographic methods of isolating heterodimeric proteins from a mixture comprising heterodimeric proteins and homodimeric proteins on the basis of the electrostatic state (e.g., electric charge difference) of one or more of an immunoglobulin-like hinge polypeptide or region, and/or a CH3 region. The electrostatic state or electric charge differences can be influenced by ionic strength and/or pH level.

Chromatographies can include, for example, affinity chromatography, ion exchange chromatography, hydrophobic interaction chromatography, hydroxyapatite chromatography, gel filtration chromatography, reverse-phase chromatography, and adsorption chromatography. Liquid phase chromatography (e.g., HPLC (High-Performance (or Pressure) Liquid Chromatography) and FPLC (Fast Protein Liquid Chromatography)) can be used for carrying out the chromatographies disclosed above. Examples of columns for affinity chromatography include protein A (synthetic, recombinant, or native) columns and protein G (synthetic, recombinant, or native) columns.

In some embodiments, the purified heterodimeric protein preparation resulting from chromatography is highly pure, i.e., having less than about any of 10, 9, 8, 7, 6, 5, 4, 3, 2, 1, 0.1, 0.1, 0.01 percent to no homodimer present. In some embodiments, the chromatography is ion exchange chromatography.

In some embodiments, the heterodimeric protein to be purified comprises an immunoglobulin-like Fc region, wherein the Fc region comprises a first Fc polypeptide and a second Fc polypeptide which interact together to form an Fc interface, wherein electrostatic interactions between one or more charged amino acids within the Fc interface favor heterodimer formation over homodimer formation, wherein the purification is performed using at least one purification step that separates on the basis of the electrostatic state of one or more of an immunoglobulin-like hinge polypeptide or region, and a CH3 region. In certain embodiments, at least one purification step comprises or consists essentially of a step of ion exchange chromatography method. In some embodiments, purification step consists of a step of ion exchange chromatography method. Any other suitable methods for purifying a heterodimeric protein comprising an immunoglobulin-like Fc region, wherein the Fc region comprises a first Fc polypeptide and a second Fc polypeptide which interact together to form a Fc interface, wherein electrostatic interactions between one or more charged amino acids within the Fc interface favor heterodimer formation over homodimer formation may be used to purify heteromultimeric proteins, e.g., heterodimers disclosed herein and are encompassed by the present invention.

In some embodiments, the heterodimeric protein to be purified comprises an immunoglobulin-like hinge region, wherein the hinge region comprises a first hinge polypeptide and a second hinge polypeptide which interact together to form a hinge interface, wherein electrostatic interactions between one or more charged amino acids within the hinge interface favor heterodimer formation over homodimer formation, wherein the purification comprises or consists essentially of a step of ion exchange chromatography method of purifying a heterodimeric protein comprising an immunoglobulin-like hinge region, wherein the hinge region comprises a first hinge polypeptide and a second hinge polypeptide which interact together to form a hinge interface, wherein electrostatic interactions between one or more charged amino acids within the hinge interface favor heterodimer formation over homodimer formation. In some embodiments, purification step consists of a step of ion exchange chromatography method.

In some embodiments, the heterodimeric protein to be purified comprises an immunoglobulin-like CH3 region, wherein the CH3 region comprises a first CH3 polypeptide and a second CH3 polypeptide which interact together to form a CH3 interface, wherein electrostatic interactions between one or more charged amino acids within the CH3 interface favor heterodimer formation over homodimer formation, wherein the purification comprises or consists essentially of a step of ion exchange chromatography method of purifying a heterodimeric protein comprising an immunoglobulin-like CH3 region, wherein the CH3 region comprises a first CH3 polypeptide and a second CH3 polypeptide which interact together to form a CH3 interface, wherein electrostatic interactions between one or more charged amino acids within the CH3 interface favor heterodimer formation over homodimer formation. In some embodiments, purification step consists of a step of ion exchange chromatography method.

Methods of Using Heteromultimeric Proteins

The present invention also provides various therapeutic applications for the heteromultimeric proteins (e.g., heterodimeric polypeptide or bispecific antibody) as described herein. In one aspect, the heteromultimeric proteins can be used for treating various diseases (e.g., cancer, autoimmune diseases, or viral infections) by binding the first protein (e.g., first human antibody variable domain) to an effector antigen and by binding the second protein (e.g., second human antibody variable domain) to a target antigen. For example, the heteromultimeric proteins (e.g., heterodimeric polypeptide or bispecific antibody) can be used for redirecting cytotoxicity, delivering thrombolytic agents to clots, for delivering immunotoxins to tumor cells, or for converting enzyme activated prodrugs at a target site (e.g., a tumor).

In another aspect, the heteromultimeric proteins (e.g., heterodimeric polypeptide or bispecific antibody) can be used for increasing specificity of a therapeutic agent and/or modulating synergistic or additive pathways (e.g., metabolic or biochemical pathways). For example, the heteromultimeric proteins (e.g., heterodimeric polypeptide or bispecific antibody) can engage receptor/receptor, receptor/ligand, ligand/ligand, cell/cell, ligand/payload, receptor/payload, or single receptor.

Pharmaceutical Compositions

In one aspect, the present invention provides a pharmaceutical composition comprising a heteromultimeric, e.g., heterodimeric polypeptide, e.g., bispecific antibody, of the invention or portion thereof as described above in a pharmaceutically acceptable carrier. In certain embodiments, the polypeptides of the invention may be present in a neutral form (including zwitter ionic forms) or as a positively or negatively-charged species. In some embodiments, the polypeptides may be complexed with a counterion to form a "pharmaceutically acceptable salt," which refers to a complex comprising one or more polypeptides and one or more counterions, where the counterions are derived from pharmaceutically acceptable inorganic and organic acids and bases.

The heterodimeric proteins, or portions thereof, may be administered alone or in combination with one or more other polypeptides of the invention or in combination with one or more other drugs (or as any combination thereof). The pharmaceutical compositions, methods and uses of the invention thus also encompass embodiments of combinations (co-administration) with other active agents, as detailed below.

As used herein, the terms "co-administration," "co-administered" and "in combination with," referring to the antibodies of the invention and one or more other therapeutic agents, is intended to mean, and does refer to and include the following: (i) simultaneous administration of such combination of a heterodimer disclosed herein and therapeutic agent(s) to a patient in need of treatment, when such components are formulated together into a single dosage form which releases said components at substantially the same time to said patient; (ii) substantially simultaneous administration of such combination of a heterodimer disclosed herein and therapeutic agent(s) to a patient in need of treatment, when such components are formulated apart from each other into separate dosage forms which are taken at substantially the same time by said patient, whereupon said components are released at substantially the same time to said patient; (iii) sequential administration of such combination of a heterodimer disclosed herein and therapeutic agent(s) to a patient in need of treatment, when such components are formulated apart from each other into separate dosage forms which are taken at consecutive times by said patient with a significant time interval between each administration, whereupon said components are released at substantially different times to said patient; and (iv) sequential administration of such combination of a heterodimer disclosed herein and therapeutic agent(s) to a patient in need of treatment, when such components are formulated together into a single dosage form which releases said components in a controlled manner whereupon they are concurrently, consecutively, and/or overlappingly released at the same and/or different times to said patient, where each part may be administered by either the same or a different route.

Generally, the heterodimeric proteins disclosed herein or portions thereof are suitable to be administered as a formulation in association with one or more pharmaceutically acceptable excipient(s). The term 'excipient' is used herein to describe any ingredient other than the compound(s) of the invention. The choice of excipient(s) will to a large extent depend on factors such as the particular mode of administration, the effect of the excipient on solubility and stability, and the nature of the dosage form. As used herein, "pharmaceutically acceptable excipient" includes any and all solvents, dispersion media, coatings, antibacterial and antifungal agents, isotonic and absorption delaying agents, and the like that are physiologically compatible. Some examples of pharmaceutically acceptable excipients are water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Additional examples of pharmaceutically acceptable substances are wetting agents or minor amounts of auxiliary substances such as wetting or emulsifying agents, preservatives or buffers, which enhance the shelf life or effectiveness of the antibody.

Pharmaceutical compositions of the present invention and methods for their preparation will be readily apparent to those skilled in the art. Such compositions and methods for their preparation may be found, for example, in Remington's Pharmaceutical Sciences, 19th Edition (Mack Publishing Company, 1995). Pharmaceutical compositions are preferably manufactured under GMP conditions.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage. Any method for administering peptides, proteins or antibodies accepted in the art may suitably be employed for the heterodimeric proteins and portions thereof disclosed herein.

The pharmaceutical compositions of the invention are typically suitable for parenteral administration. As used herein, "parenteral administration" of a pharmaceutical composition includes any route of administration characterized by physical breaching of a tissue of a subject and administration of the pharmaceutical composition through the breach in the tissue, thus generally resulting in the direct administration into the blood stream, into muscle, or into an internal organ. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal, intravenous, intraarterial, intrathecal, intraventricular, intraurethral, intracranial, intrasynovial injection or infusions; and kidney dialytic infusion techniques. Preferred embodiments include the intravenous and the subcutaneous routes.

Formulations of a pharmaceutical composition suitable for parenteral administration typically generally comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampoules or in multi dose containers containing a preservative. Formulations for parenteral administration include, but are not limited to, suspensions, solutions, emulsions in oily or aqueous vehicles, pastes, and the like. Such formulations may further comprise one or more additional ingredients including, but not limited to, suspending, stabilizing, or dispersing agents. In one embodiment of a formulation for parenteral administration, the active ingredient is provided in dry (i.e. powder or granular) form for reconstitution with a suitable vehicle (e.g. sterile pyrogen free water) prior to parenteral administration of the reconstituted composition. Parenteral formulations also include aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water. Exemplary parenteral administration forms include solutions or suspensions in sterile aqueous solutions, for example, aqueous propylene glycol or dextrose solutions. Such dosage forms can be suitably buffered, if desired. Other parentally-administrable formulations which are useful include those which comprise the active ingredient in microcrystalline form, or in a liposomal preparation. Formulations for parenteral administration may be formulated to be immediate and/or modified release. Modified release formulations include controlled, delayed, sustained, pulsed, targeted and programmed release formulations. For example, in one aspect, sterile injectable solutions can be prepared by incorporating the heterodimeric protein, e.g., bispecific antibody, in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze drying that yields a powder of the active ingredient plus any additional desired ingredient from a previously sterile filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

An exemplary, non-limiting pharmaceutical composition of the invention is a formulation as a sterile aqueous solution having a pH that ranges from about 5.0 to about 6.5 and comprising from about 1 mg/mL to about 200 mg/mL of a heterodimeric protein disclosed herein, from about 1 millimolar to about 100 millimolar of histidine buffer, from about 0.01 mg/mL to about 10 mg/mL of polysorbate 80, from about 100 millimolar to about 400 millimolar of trehalose, and from about 0.01 millimolar to about 1.0 millimolar of disodium EDTA dihydrate.

Dosage regimens may be adjusted to provide the optimum desired response. For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form, as used herein, refers to physically discrete units suited as unitary dosages for the patients/subjects to be treated; each unit containing a predetermined quantity of active compound calculated to produce the desired therapeutic effect in association with the required pharmaceutical carrier. The specification for the dosage unit forms of the invention are generally dictated by and directly dependent on (a) the unique characteristics of the chemotherapeutic agent and the particular therapeutic or prophylactic effect to be achieved, and (b) the limitations inherent in the art of compounding such an active compound for the treatment of sensitivity in individuals.

Thus, the skilled artisan would appreciate, based upon the disclosure provided herein, that the dose and dosing regimen is adjusted in accordance with methods well-known in the therapeutic arts. That is, the maximum tolerable dose can be readily established, and the effective amount providing a detectable therapeutic benefit to a patient may also be determined, as can the temporal requirements for administering each agent to provide a detectable therapeutic benefit to the patient. Accordingly, while certain dose and administration regimens are exemplified herein, these examples in no way limit the dose and administration regimen that may be provided to a patient in practicing the present invention.

It is to be noted that dosage values may vary with the type and severity of the condition to be alleviated, and may include single or multiple doses. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition. Further, the dosage regimen with the compositions of this invention may be based on a variety of factors, including the type of disease, the age, weight, sex, medical condition of the patient, the severity of the condition, the route of administration, and the particular antibody employed. Thus, the dosage regimen can vary widely, but can be determined routinely using standard methods. For example, doses may be adjusted based on pharmacokinetic or pharmacodynamic parameters, which may include clinical effects such as toxic effects and/or laboratory values. Thus, the present invention encompasses intra-patient dose-escalation as determined by the skilled artisan. Determining appropriate dosages and regimens are well-known in the relevant art and would be understood to be encompassed by the skilled artisan once provided the teachings disclosed herein.

For administration to human subjects, the total monthly dose of a heterodimeric protein disclosed herein is typically in the range of about 0.5 to about 1200 mg per patient, depending, of course, on the mode of administration. For example, an intravenous monthly dose may require about 1 to about 1000 mg/patient. The total monthly dose may be administered in single or divided doses and may, at the physician's discretion, fall outside of the typical range given herein.

An exemplary, non-limiting range for a therapeutically or prophylactically effective amount of a heterodimeric protein, e.g., a bispecific antibody or portion thereof, disclosed herein is about 1 to about 1000 mg/patient/month. In certain embodiments, the heterodimeric protein may be administered at about 1 to about 200 or about 1 to about 150 mg/patient/month.

EXAMPLES

The following examples describe construction, generation, and purification of heterodimeric proteins comprising mutations in the hinge region only, in both the hinge region and CH3 regions, or in the CH3 region only. The following examples are meant to illustrate the methods and materials of the present invention. Suitable modifications and adaptations of the described conditions and parameters normally encountered in the art that are obvious to those skilled in the art are within the spirit and scope of the present invention.

Antibodies Used in the Examples

| Antibody Identifier | Antibody Description* |
| --- | --- |
| Ab1 | anti-antigen A antibody |
| Ab2 | anti-antigen B antibody comprising a lambda light chain |
| Ab3 | anti-antigen C antibody |
| Ab4 | anti-antigen D antibody |
| Ab5 | Non-antigen binding antibody |
| Ab6 | Non-antigen binding antibody |

*Antigen A is a hormone protein; antigens B and C are two different growth factor receptor proteins; and antigen D is a calcium signal transducer protein.

Example 1

Generation of Human IgG1, IgG2, and IgG4 Antibody Mutant Clones

PCR Mutagenesis

In this and other Examples below, the mutant clones of human IgG1, IgG2, and IgG4 antibodies were generated by PCR mutagenesis. For human IgG2 antibody mutant clones, an anti-antigen A antibody (also referred as Ab1) having IgG2ΔA Fc region (SEQ ID NO: 1 in FIG. 2) was used as the template (about 0.05 µg per reaction) for two steps of PCR reactions (FIG. 4). Compared to a wild-type IgG2 Fc region, this IgG2ΔA has A330S and P331S substitutions. For all the PCR reaction described in this example, the Pfu-Turbo® DNA Polymerase Kit (catalog number 600250) was used and the final dNTP concentration was 0.5 mM.

In the first step, there were two separate PCR reactions—A and B. In reaction A, a first pair of primers, hFc2.f (forward primer; SEQ ID NO: 2 in Table 2) and hFc2.hinge.r (reverse primer; SEQ ID NO: 3 in Table 2), was used at 40 pmol each. In reaction B, a second pair of primers, hFc2.hinge.mutA1.f (forward primer which contains mutations; SEQ ID NO: 4 in Table 2) and Not.hFc2.r (reverse primer; SEQ ID NO: 5 in Table 2) was used at 40 pmol each. The forward primer—hFc2. hinge.mutA1.f comprised mutated nucleic acids compared to a wild-type IgG2 hinge region and introduced the desired mutations into the hinge region. The anneal temperature for PCR reactions described here is 54° C. The primers used in the PCR reactions comprise degenerate nucleotides, i.e., "S" in the sequence stands for C or G in the primer and "R" stands for A or G in the primer.

The PCR products obtained from reaction A and reaction B were gel purified by QIAquick Gel Exaction Kit (catalog number 28706) and further eluted in 30 µl EB buffer.

In the second step of PCR reactions, 2.5 µl of the purified PCR products from reaction A and reaction B, respectively, were amplified for 8 cycles first without the addition of any primers and then were subjected to 20 cycles with the following primers (40 pmol each)—forward primer: hFc2.f (SEQ ID NO: 2) and reverse primer: Not.hFc2.r (SEQ ID NO: 5). The anneal temperature for PCR reactions described here is 54° C.

Figure 3:
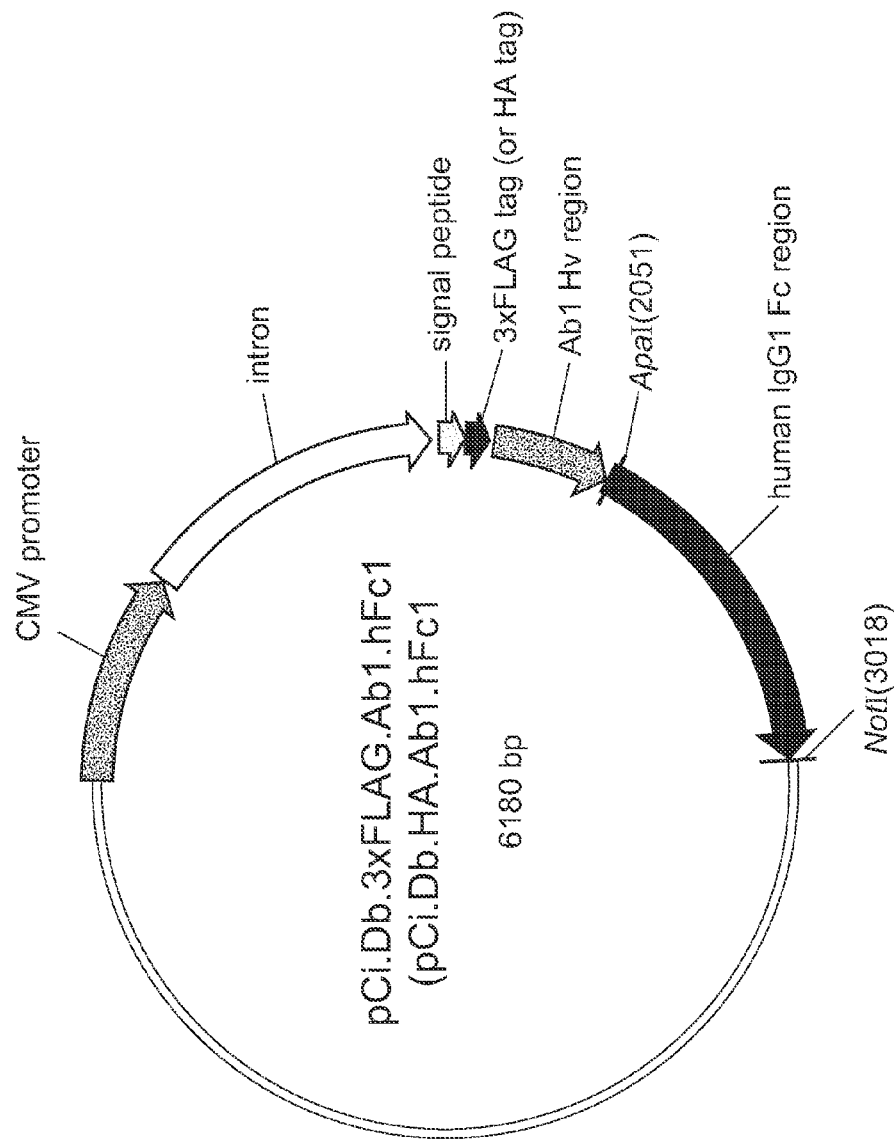
FIG. 3 depicts a vector map for pCi.Db.3xFLAG (or HA).Ab1.hFc1 vector.

The PCR products obtained from the second step were gel purified by QIAquick Gel Exaction Kit (catalog number 28706) and further eluted in 30 µl EB buffer. The purified PCR products were digested by ApaI and NotI and further cloned into either a pCi.Db.3XFLAG.Ab1.hFc1 vector or a pCi.Db.HA.Ab1.hFc1 vector (FIG. 3).

A number of different mutation-containing primers (SEQ ID NOS: 6-10) were used to replace hFc2.hinge.mutA1.f in the 1st step PCR reaction to introduce different mutations into the hinge region. A human IgG2ΔA antibody mutant—IgG2ΔA (K409) having a K409R substitution in the CH3 region was also used as a template to replace the human IgG2ΔA antibody template to generate different mutations in the hinge region.

The IgG1 and IgG4 antibody mutants were generated by a PCR mutagenesis process, using essentially the same as procedures as previously described. For human IgG1 antibody mutant clones, DNA encoding antibody Ab1 IgG1 (SEQ ID NO: 11 in FIG. 4) having a K409R substitution in the CH3 region was used as the PCR template. For human IgG4 antibody mutant clones, a wild-type antibody Ab1 IgG4 Fc region (SEQ ID NO: 12 in FIG. 5) was used as the PCR template. The primers used for generation of IgG1 and IgG4 mutant clones are listed in Table 2.

Mutant Clones

Multiple mutant clones were generated for human IgG1, IgG2 and IgG4 antibodies with mutated residues in the hinge regions. For human IgG4 antibody mutant clones, the residue Ser228 in a wild-type Fc hinge region (see the underlined residue in FIG. 6A) was mutated to either a positively charged residue (Lys or Arg; group A) or to a negatively charged residue (Asp or Glu; group B) in the mutant clones listed in the table of FIG. 6B. For human IgG2 antibody mutant clones in groups AI and BI, the human IgG2ΔA antibody having A330S and P331S substitutions compared to IgG2 was used as the template. For mutant clones in groups AI and BI, the human IgG2ΔA antibody mutant—IgG2ΔA (K409) having a K409R substitution in the CH3 region, was used as the template. The three residues Cys223, Glu225, and Pro228 in the hinge region of the antibody template, as underlined in FIG. 6A, were mutated, respectively, to either a positively charged residue (Arg or Lys) or a negatively charged residue (Glu or Asp) to produce the mutant clones listed in the table of FIG. 6B. For human IgG1 antibody mutant clones, as described above, the human IgG1 (K409R) mutant was used as the template and the residues Ser221 and Pro228 in the hinge region, as underlined in FIG. 6A, were respectively mutated to either a positive charged residue (Arg or Lys) or a negative charged residue (Glu or Asp) to generate the mutant clones as listed in the table of FIG. 6B.

To distinguish mutants having different Fc regions, the group A mutants of IgG4 and the groups AI and AII mutants of IgG2 were engineered to further comprise an N-terminus 3xFLAG tag (DYKDHDGDYKDHDIDYKDDDDKGLE, SEQ ID NO: 53), while group B mutants of IgG4 and groups BI and BII mutants of IgG2 were engineered to further comprise an N-terminus HA tag (YPYDVPDYALE, SEQ ID NO: 54).

TABLE 2

PCR Primer Sequences for Generating Hinge Region Mutations

| Primer Name | Primer Sequence | SEQ ID NO |
|---|---|---|
| hFc2.f | GCCTCCACCAAGGGCCCATC | SEQ ID NO: 2 |
| Not.hFc2.r | ATACAAGCGGCCGCCTATTTACCCGG AGACAGGGA | SEQ ID NO: 5 |
| hFc2.hinge.mutA1.f | ACAAGACCGTGGAGAGAAAGTGTGA SGTGGAGTGTCCAARGTGTCCAGCCC CTCCAGTGG | SEQ ID NO: 4 |
| hFc2.hinge.mutA2.f | ACAAGACCGTGGAGAGAAAGTGTGA SGTGGAGTGTCCAGASTGTCCAGCCC CTCCAGTGG | SEQ ID NO: 6 |
| hFc2.hinge.mutA3.f | ACAAGACCGTGGAGAGAAAGTGTGA SGTGARGTGTCCAGASTGTCCAGCCC CTCCAGTGG | SEQ ID NO: 7 |

TABLE 2-continued

PCR Primer Sequences for Generating Hinge Region Mutations

| Primer Name | Primer Sequence | SEQ ID NO |
|---|---|---|
| hFc2.hinge.mutB1.f | ACAAGACCGTGGAGAGAAAGTGTAR GGTGARGTGTCCAGASTGTCCAGCCC CTCCAGTGG | SEQ ID NO: 8 |
| hFc2.hinge.mutB2.f | ACAAGACCGTGGAGAGAAAGTGTAR GGTGARGTGTCCAARGTGTCCAGCCC CTCCAGTGG | SEQ ID NO: 9 |
| hFc2.hinge.mutB3.f | ACAAGACCGTGGAGAGAAAGTGTAR GGTGGAGTGTCCAARGTGTCCAGCC CCTCCAGTGG | SEQ ID NO: 10 |
| hFc2.hinge.r | CTTTCTCTCCACGGTCTTG | SEQ ID NO: 3 |
| hFc4.f | GCCTCCACCAAGGGCCCATC | SEQ ID NO: 13 |
| Not.hFc4.r | ATACAAGCGGCCGCCTATTTACCCAG AGACAGGGAGA | SEQ ID NO: 14 |
| hFc4.hinge.mutA.f | GAGTCCAAATATGGTCCCCCATGCCC AARGTGCCCAGCACCTGAGTTCCT | SEQ ID NO: 15 |
| hFc4.hinge.mutB.f | GAGTCCAAATATGGTCCCCCATGCCC AGASTGCCCAGCACCTGAGTTCCT | SEQ ID NO: 16 |
| hFc4.hinge.mut.r | TGGGGGACCATATTTGGACT | SEQ ID NO: 17 |
| hFc1.f | GCCTCCACCAAGGGCCCATC | SEQ ID NO: 18 |
| Not.hFc1.r | ATACAAGCGGCCGCCTATTTACCCGG AGACAGGGA | SEQ ID NO: 19 |
| hFc1.hinge.EE.f | GAAAGTTGAGCCCAAATCTTGTGAG AAAACTCACACATGCCCAGAGTGCC CAGCACCTGAACTCC | SEQ ID NO: 20 |
| hFc1.hinge.RR.f | GAAAGTTGAGCCCAAATCTTGTAGG AAAACTCACACATGCCCAAGGTGCC CAGCACCTGAACTCC | SEQ ID NO: 21 |
| hFc1.hinge.r | ACAAGATTTGGGCTCAACTTTC | SEQ ID NO: 22 |

Example 2

IgG4 Hinge-Containing Heterodimers

This Example illustrates heterodimeric proteins containing mutant IgG4 hinge.

Figures 7A, 7B:
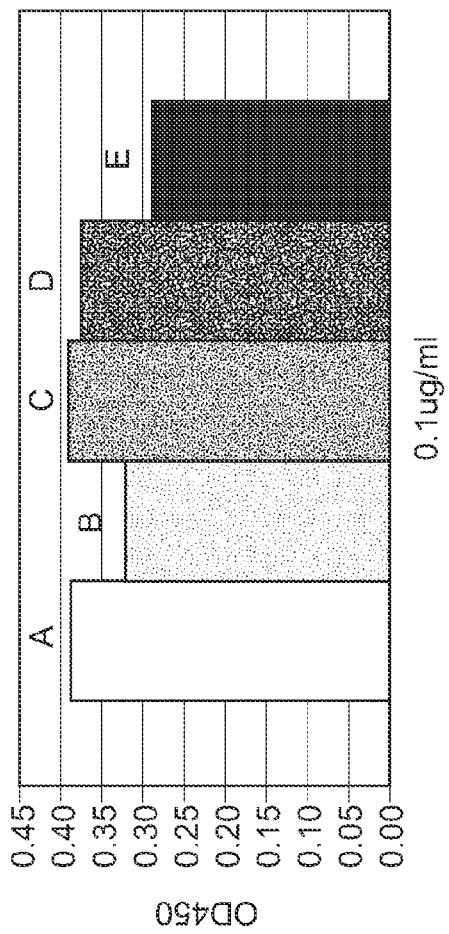
FIGS. 7A-7B depict an analysis of bispecific antibody formation from IgG4 mutants.

The human IgG4 antibody group A and group B mutants were mixed together in four different combination pairs (as shown in FIG. 7B). Each pair was co-transfected with antibody Ab1 light chain into 293F cells grown in suspension culture. Briefly, 293F cells were seeded at 1×10⁶ cells/ml in 293 Freestyle media in Erlenmeyer flasks (8% CO2, 120 rpm). For the transfection (amounts based on a 50 ml transfection, can be scaled up as needed), 2.5 ml of OptiMEM was first added to 2×15 ml tubes. 50 μg of DNA (heavy chain A:heavy chain B:light chain=1.5:1.5:2) was then added to tube A. 100 ul of a 1 mg/ml solution of transfection reagent was added to tube B. The materials in tubes A and B were mixed together and incubated at RT for 15 minutes. A DNA-transfection reagent complex solution was added to cells and then the cells were returned to incubator. After 24 hours, 1.25 ml of a 20% w/v stock of Tryptone N1 was added and the cells were returned to incubator. Supernatants were harvested after 5 days. The transfection reagent was prepared by dissolving it to 1 mg/ml in water, adjusting pH to below 2.5 with HCl. After dissolving, the pH was further adjusted to 7.0 followed by 0.22 μm filtration (aliquot and store at −20° C.). The Tryptone N1 was made a 20% w/v stock in 293Freestyle media, and followed by 0.22 μm filtration (store at 4° C.).

Total proteins in each preparation were separated using immunoaffinity purification on a protein G column (Protein G agarose, Pierce cat #20399; IgG elution buffer, Pierce cat #21004; See, e.g., Bjorck and Kronvall, *J. Immunol.* (133): 969-974 (1984)). The percentage of bispecific antibodies in each preparation were measured by a standard sandwich ELISA assay. Briefly, plates were coated with anti-HA and the detection antibody was anti-FLAG. The antibody Ab1 having a wild-type IgG4 region was expressed and purified in the same manner and used as a standard control for the ELISA assays because wild-type IgG4 naturally forms about 50% bispecific antibody (van der Neut Kolfschoten M et al., *Science* (317): 1554-1557 (2007); Aalberse R C et al., *Immunology* (105):9-19 (2002)).

To detect the bispecific antibodies, 0.1 μg/ml purified total protein from each preparation was added into each ELISA plate with 1 μg/ml of anti-HA tag antibody. The bispecific antibodies in each preparation were detected by reacting with an HRP-conjugated anti-FLAG antibody.

The ELISA assay results (FIG. 7A) demonstrate that introducing one or more mutations to drive heterodimer formation based on favorable electrostatic interactions between hinge regions of heterodimers compared to homodimers in a human IgG4 hinge region helped stabilize heterodimeric antibody formation and thus produced more bispecific antibodies than the same procedure using only a wild-type IgG4 antibody.

Example 3

IgG2 Hinge-Containing Heterodimers

The human IgG2 antibody group AI mutants and group BI mutants were mixed together in three different combination pairs, 1A, 1B, and 1C (as shown in FIG. 8B). Each pair was co-transfected with antibody Ab1 light chain into 293 cells. The human IgG2 antibody group AII mutants and group BII mutants were also mixed together in three different combination pairs, 2A, 2B, and 2C (as shown in FIG. 8B). Each pair was co-transfected with antibody Ab1 light chain into suspension 293 cells. Supernatants were harvested after 5 days. Total proteins in each preparation were purified by protein G column. The percentage of bispecific antibodies in each preparation were measured by sandwich ELISA. The antibody Ab1 with wild-type IgG2 Fc region was expressed and purified in the same manner and used as a standard control for the ELISA assay. As described in Example 1, all the mutants in 1A, 1B, and 1C have a wild-type IgG2ΔA CH3 region, and all the mutants in 2A, 2B, and 2C have K409R mutation in the CH3 region of IgG2ΔA.

To detect the bispecific antibodies, 0.1 μg/ml purified total protein from each preparation was added into ELISA plate with 1 μg/ml anti-HA tag antibody. The bispecific antibodies in each preparation were detected by HRP-conjugated anti-FLAG antibody.

The ELISA assay results (FIG. 8A) demonstrate that introducing the K409 mutation in the CH3 region of human IgG2ΔA antibody helped promote heterodimeric antibody formation.

Example 4

Screening for the IgG2 Hinge Mutation that Promotes Heterodimer Formation in K409R Background The human IgG2 antibody group AII mutants and group BII mutants were combined in six different combination pairs, A-F (as shown in FIG. 9B). Each pair of clones was co-transfected with antibody Ab1 light chain into 293 cells. Supernatants were harvested after 5 days. Total proteins in each preparation were purified by protein G column. The percentage of bispecific antibodies in each preparation were measured by sandwich ELISA. The antibody Ab1 with wild-type IgG2 Fc region and with wild-type IgG4 Fc region were individually expressed and purified in the same manner and used both controls for the ELISA assay. All the mutant clones used in this Example have K409R mutation in the CH3 region of IgG2ΔA.

To detect the bispecific antibodies, 0.17 μg/ml purified total protein from each preparation was added into ELISA plate coated with 1 μg/ml anti-HA tag antibody. The bispecific antibodies in each preparation were detected by HRP-conjugated anti-FLAG antibody.

The ELISA assay results (FIG. 9A) demonstrate that in the K409R background, when three hinge mutations—C223E, E225E, and P228E, combined with three hinge mutations C223R, E225R, and P228R, i.e., column D in FIG. 9A, we observed more bispecific antibodies than the other mutation combinations tested.

Example 5

"Glu" Scanning of Human IgG4 CH3 Regions

Fourteen positions from the CH3 regions of the human IgG4 antibody were chosen to carry out a series of "Glu" scanning experiment. Criteria for choosing these fourteen positions were essentially as described in W. Dall'Acqua et al. *Biochemistry* (37):9266-9273 (1998). The positions chosen for the "Glu" scanning were numbered 1-14 as shown in FIG. 10. All the mutants were generated using a site-directed mutagenesis kit from Stratagene (QuikChange® II XL Site-Directed Mutagenesis Kit, Catalog #200522). The primers used for generating specific mutation in the CH3 region are listed in Table 3.

The template clone used to generate the IgG4 mutants was Ab1.3.11A, which has an N-terminal 3xFLAG tag and a S228R mutation in its hinge region.

All the mutant clones and the template clones, as listed in FIG. 11B, were expressed and purified individually. Equal amounts of Ab1.3.2A protein, which has a S228E mutation in the hinge region and a N-terminal HA tag, and various Ab1.3.11A CH3 mutants were mixed together in various combinations (FIG. 11B) and further incubated with 0.5 mM glutathione (GSH) at 37° C. for 24 hour. The Ab1.3.11A template without any CH3 region mutation was also mixed with equal amounts of Ab1.3.2A protein and further incubated with 0.5 mM glutathione (GSH) at 37° C. for 24 hour (column 15 in FIG. 11A). The protocol for the GSH reaction was essentially as described in Labrijn et al., *Nature Biotechnology*, (27), 767-771 (2009).

TABLE 3

PCR Primer Sequences for Generating CH3 Region Mutations

| Primer Name | hFc1 Primer Sequence | SEQ ID NO |
|---|---|---|
| Fc1.Q347E.f | CCCCGAGAACCAGAGGTGTACACCCTG | SEQ ID NO: 23 |
| Fc1.Q347E.r | CAGGGTGTACACCTCTGGTTCTCGGGG | SEQ ID NO: 24 |
| Fc1.Y349E.f | GAGAACCACAGGTGGAGACCCTGCCCCCAT | SEQ ID NO: 25 |
| Fc1.Y349E.r | ATGGGGGCAGGGTCTCCACCTGTGGTTCTC | SEQ ID NO: 26 |
| Fc1.T350E.f | AACCACAGGTGTACGAGCTGCCCCCATCCC | SEQ ID NO: 27 |
| Fc1.T350E.r | GGGATGGGGGCAGCTCGTACACCTGTGGTT | SEQ ID NO: 28 |
| Fc1.L351E.f | CACAGGTGTACACCGAGCCCCCATCCCGGG | SEQ ID NO: 29 |

TABLE 3-continued

PCR Primer Sequences for Generating CH3 Region Mutations

| Primer Name | hFc1 Primer Sequence | SEQ ID NO |
|---|---|---|
| Fc1.L351E.r | CCCGGGATGGGGCTCGGTGTACACCTGTG | SEQ ID NO: 30 |
| Fc1.T366E.f | CCAGGTCAGCCTGGAGTGCCTGGTCAAAGG | SEQ ID NO: 31 |
| Fc1.T366E.r | CCTTTGACCAGGCACTCCAGGCTGACCTGG | SEQ ID NO: 32 |
| Fc1.L368E.f | CAGCCTGACCTGCGAGGTCAAAGGCTTCTA | SEQ ID NO: 33 |
| Fc1.L368E.r | TAGAAGCCTTTGACCTCGCAGGTCAGGCTG | SEQ ID NO: 34 |
| Fc1.K370E.f | TGACCTGCCTGGTCGAGGGCTTCTATCCCA | SEQ ID NO: 35 |
| Fc1.K370E.r | TGGGATAGAAGCCCTCGACCAGGCAGGTCA | SEQ ID NO: 36 |
| Fc1.K392E.f | GGAGAACAACTACGAGACCACGCCTCCCGT | SEQ ID NO: 37 |
| Fc1.K392E.r | ACGGGAGGCGTGGTCTCGTAGTTGTTCTCC | SEQ ID NO: 38 |
| Fc1.T394E.f | CAACTACAAGACCGAGCCTCCCGTGCTGGA | SEQ ID NO: 39 |
| Fc1.T394E.r | TCCAGCACGGGAGGCTCGGTCTTGTAGTTG | SEQ ID NO: 40 |
| Fc1.V397E.f | GACCACGCCTCCCGAGCTGGACTCCGACGG | SEQ ID NO: 41 |
| Fc1.V397E.r | CCGTCGGAGTCCAGCTCGGGAGGCGTGGTC | SEQ ID NO: 42 |
| Fc1.L398E.f | ACGCCTCCCGTGGAGGACTCCGACGGCTCC | SEQ ID NO: 43 |
| Fc1.L398E.r | GGAGCCGTCGGAGTCCTCCACGGGAGGCGT | SEQ ID NO: 44 |
| Fc1.F405E.f | GACGGCTCCTTCGAGCTGTACAGCAAGCTC | SEQ ID NO: 45 |
| Fc1.F405E.r | GAGCTTGCTGTACAGCTCGAAGGAGCCGTC | SEQ ID NO: 46 |
| Fc1.Y407E.f | CTCCTTCTTCCTCGAGAGCAAGCTCACCG | SEQ ID NO: 47 |
| Fc1.Y407E.r | CGGTGAGCTTGCTCTCGAGGAAGAAGGAG | SEQ ID NO: 48 |
| Fc1.K409E.f | TTCCTCTACAGCGAGCTGACCGTGGACAAGA | SEQ ID NO: 49 |
| Fc1.K409E.r | TCTTGTCCACGGTCAGCTCGCTGTAGAGGAA | SEQ ID NO: 50 |
| Fc1.K409R.f | TTCCTCTACAGCAGGCTGACCGTGGACAAGA | SEQ ID NO: 51 |
| Fc1.K409R.r | TCTTGTCCACGGTCAGCCTGCTGTAGAGGAA | SEQ ID NO: 52 |

The aliquot from each GSH reaction was diluted in ice-cold PBS-TB (PBS with 0.2% BSA, 0.05% Tween-20) and the amount of bispecific antibodies was measured by sandwich ELISA as described in Example 2. The antibody Ab1 with a wild-type IgG4 Fc region was also expressed and treated in the same manner and used as a standard control (column 16 in FIG. 11A) in the ELISA assay.

As shown in FIG. 11A, none of the fourteen mutations in IgG4 CH3 region made a significant increase in bispecific antibody formation compared to the template clone without any CH3 region mutation.

Example 6

"Glu" Scanning of Human IgG2 CH3 Regions

Fourteen (14) positions from the CH3 regions of the human IgG2 antibody were chosen to carry out a series of "Glu" scanning experiment. Criteria for choosing these fourteen positions were essentially as described in Example 5. The positions chosen for the "Glu" scanning were numbered 1-14 as shown in FIG. 10. All the mutants were generated by site-direct mutagenesis kit from Stratagene.

The template used to generate the IgG2 mutants was Ab1.1.3D, which has an N-terminal HA tag, a wild-type IgG2ΔA CH3 region, and three mutations, i.e., C223R, E225R, and P228R, in the IgG2ΔA hinge region.

Figures 12A, 12B:
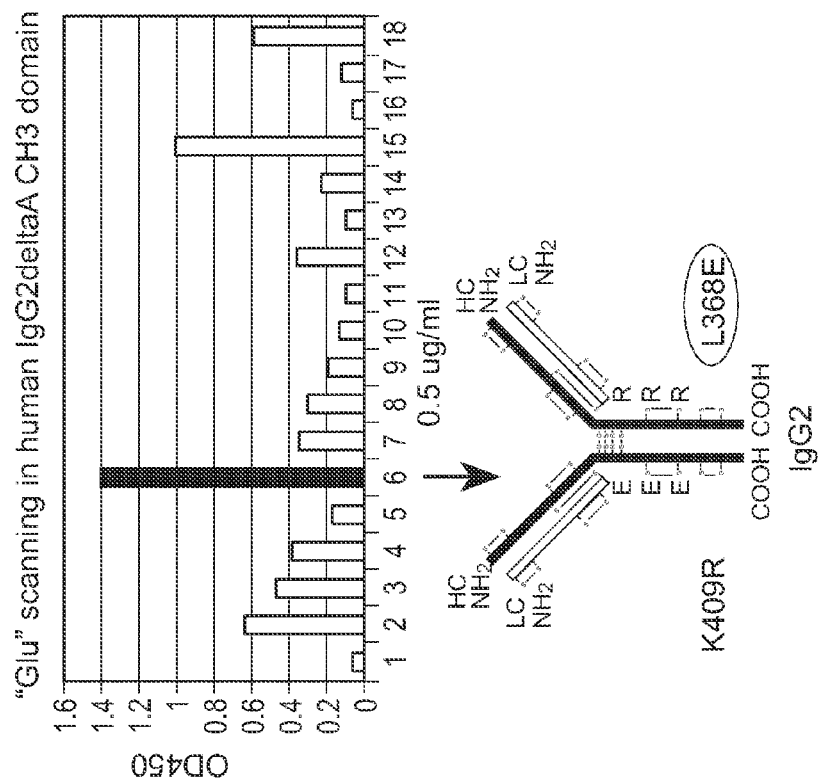
FIGS. 12A-12B depict results for "Glu" scanning on various human IgG2 mutants.

All the mutants and the wild-type controls, as listed in FIG. 12B, were expressed and purified individually. Equal amounts of the Ab1.2.2H protein, which has three mutations in the hinge region, C223E, E225E, and P228E and an N-terminal HA tag, and various Ab1.1.3D CH3 mutants (FLAG tag) were mixed together in various combination (FIG. 12B) and further incubated with 0.5 mM GSH at 37° C. for 24 hours. The aliquot from each GSH reaction was diluted in ice-cold PBS-TB (PBS with 0.2% BSA, 0.05% Tween-20) and the amount of bispecific antibodies formed was measured by sandwich ELISA as described in Example 2. The antibody Ab1 with a wild-type IgG4 Fc region, the antibody Ab1 with a wild-type IgG2ΔA Fc region and the antibody Ab1 with a mutant IgG2ΔA(K409R) Fc region were expressed and treated in the same manner and used as controls in the ELISA assays.

As shown in FIG. 12A, when mixing the Ab1.2.2H protein (three mutations—C223E, E225E, and P228E) with the Ab1.1.3D.L368E protein (three mutations—C223R, E225R, and P228R), the production of bispecific antibodies (column 6 in FIG. 12A) was significantly increased compared to the other combinations and the controls.

Example 7

Hinge Mutations and CH3 Mutations can Contribute to Heterodimer Formation

The Ab1 heavy chain variable region of some mutants was replaced with the heavy chain variable region from a different antibody, Ab2, which is an anti-antigen B antibody comprising a lambda light chain.

All the mutants and the wild-type controls listed in FIG. 13B were expressed and purified individually. Equal amounts of antibody 1 as listed in FIG. 13B and antibody 2 as listed in FIG. 13B were mixed together and incubated with or without 0.5 mM GSH at 37° C. for 24 hour. Aliquots from each GSH reaction were diluted in ice-cold PBS-TB (PBS with 0.2% BSA, 0.05% Tween-20) and the amount of bispecific antibodies was measured by sandwich ELISA, essentially as described in Example 2.

To detect bispecific antibodies, 0.25 µg/ml purified total proteins from each GSH reaction were added onto an ELISA plate coated with 1 µg/ml antigen B. The amount of bispecific antibodies in each preparation was detected by HRP conjugated anti-kappa antibody. Antibody Ab1 is an anti-antigen A antibody comprising a kappa light chain.

As shown in FIG. 13A, when two different wild-type human IgG2ΔA antibodies were mixed together under mild reducing condition (A) (1 mM GSH), no bispecific antibodies were detected compared to the controls. Similar to the results from Example 4, in the K409R background, when three hinge mutations: C223E, E225E, and P228E, combined with three hinge mutations C223R, E225R, and P228R, i.e., (B) in FIG. 13A, increased formation of bispecific antibodies was observed. Similar to the results from Example 7, replacement of the K409R mutation with L368E on one of the heavy chain CH3 regions resulted in further increased formation of bispecific antibodies (C). The combination of clones with only mutations in the CH3 region (D), less bispecific antibody was detected. Wild-type human IgG4 was used as a standard control for ELISA (column E).

Example 8

"Glu" Scanning of Human IgG1 CH3 Regions

Fourteen positions from the CH3 regions of the human IgG1 antibody were chosen to carry out a series of "Glu" scanning experiments. Criteria for choosing these fourteen positions were essentially as described in Example 5. The positions chosen for the "Glu" scanning were numbered 1-14 as shown in FIG. 10. All the mutants were generated by site-direct mutagenesis kit from Stratagene.

The template used to generate the IgG1 mutants was Ab2.hFc1.EE, which has a wild-type IgG1 CH3 region, two mutations in the IgG1 hinge region, i.e., D221E and P228E.

Figures 14A, 14B:
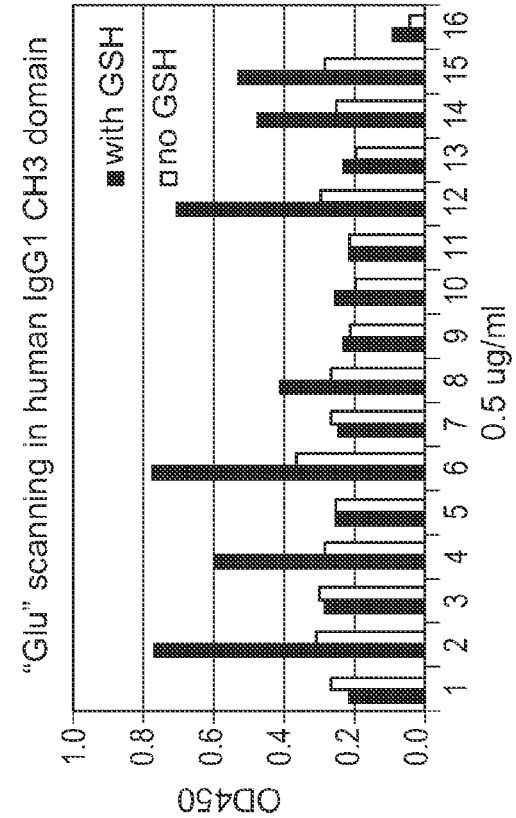
FIGS. 14A-14B depicts results for "Glu" scanning on various human IgG1 mutants.

All the mutants and the wild-type controls listed, as listed in FIG. 14B were expressed and purified individually. Equal amounts of Ab1.hFc1.RR.K409R IgG1 protein, which has a K409R mutation in the CH3 region, two mutations in the hinge region, D221R and P228R, and various Ab2.hFc1.EE IgG1 CH3 mutants were mixed together and incubated with or without 0.5 mM GSH at 37° C. for 24 hour. Aliquots from each GSH reaction were diluted in ice-cold PBS-TB (PBS with 0.2% BSA, 0.05% Tween-20) and the amount of bispecific antibodies was measured by sandwich ELISA as described in Example 2. Ab1 and Ab2 with wild-type IgG4 Fc region was expressed and treated in the same manner and used as controls in ELISA. The antibody Ab1 with a wild-type IgG4 Fc region and the antibody 11A with a wild-type IgG4 Fc region were expressed and treated in the same manner and used as controls in the ELISA assays.

As shown in FIG. 14B, very few positions in the CH3 domain of IgG1, i.e., Y349, L368, and F405, when substituted by Glu and combined with EE(K409R) mutant further increase bispecific antibody formation (columns 2, 6, and 12).

Example 9

Comparison of Bispecific Antibody Formation

This Example illustrates the preparation of IgG1 hinge-containing heterodimers and compares bispecific antibody formation with other isotypes.

Figures 15A, 15B:
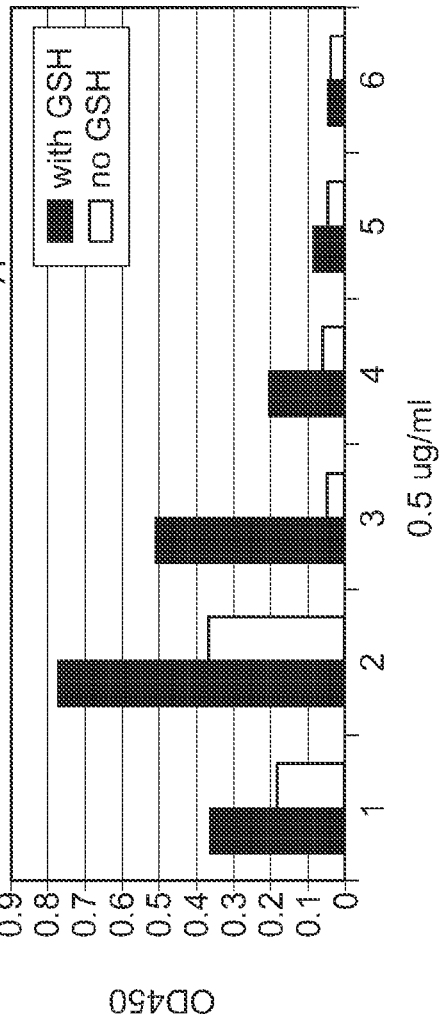
FIGS. 15A-15B depict a comparison of bispecific antibody formation between different IgG isotypes.
Figure 18A:
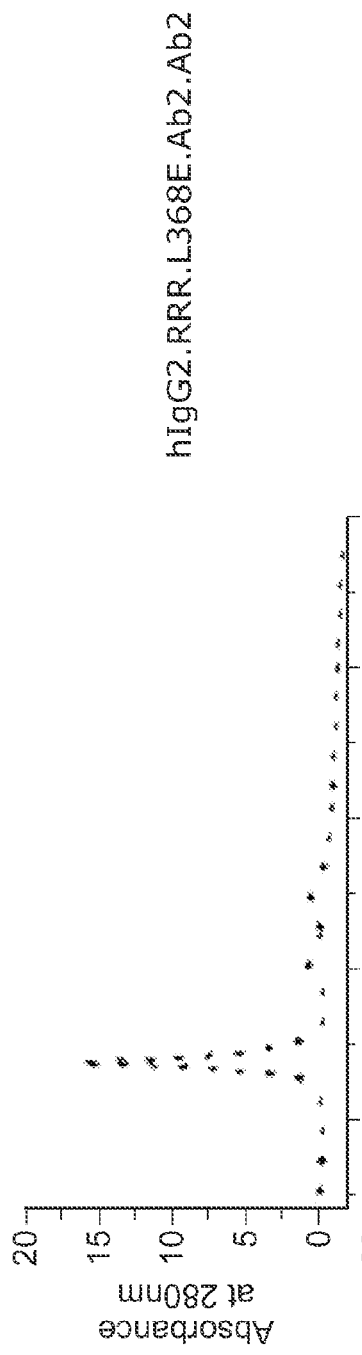
FIGS. 18A-18C depict ion exchange elution profiles of hIgG2 mutants. The hinge mutations were exchanged relative to constructs shown in FIG. 17A-17C resulting in two antibodies with less total charge difference. The pairing of the hinge mutations with different variable domains has no effect on bispecific antibody formation. Dashed line represents Ab1 antibody with 223E, 225E, and 228E mutations in the hinge region and 409R mutation in the CH3 domain of the heavy chain. Dotted line represents Ab2 hIgG1 antibody with 223R, 225R, and 228R mutations in the hinge and 368E in the CH3 domain. Solid line represents elution profile of the Ab1-Ab2 bispecific antibody reaction products formed after incubation of the Ab1 and Ab2 variants with 2 mM glutathione.
Figure 18B:
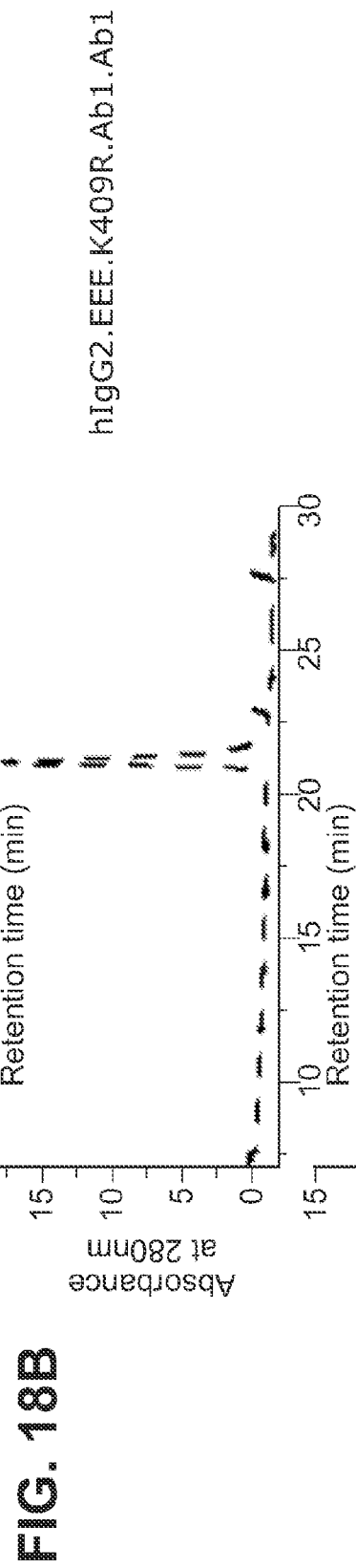
Figure 18C:
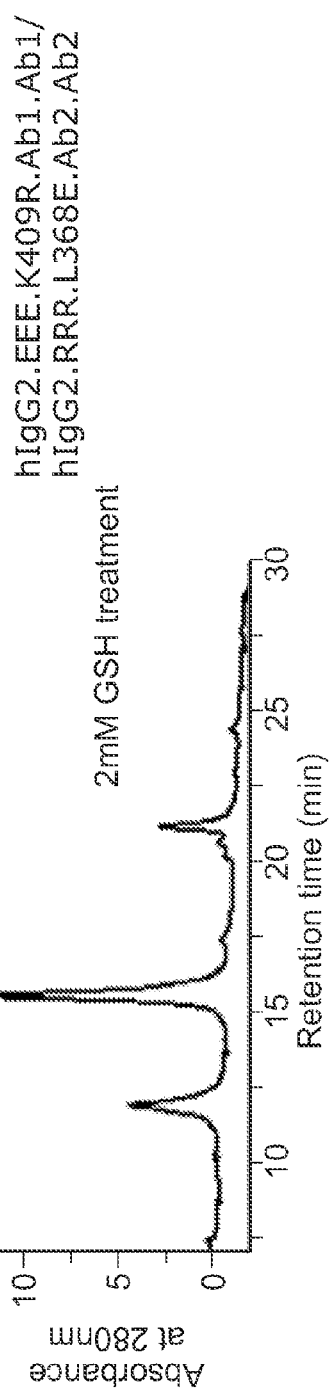
Figure 22A:
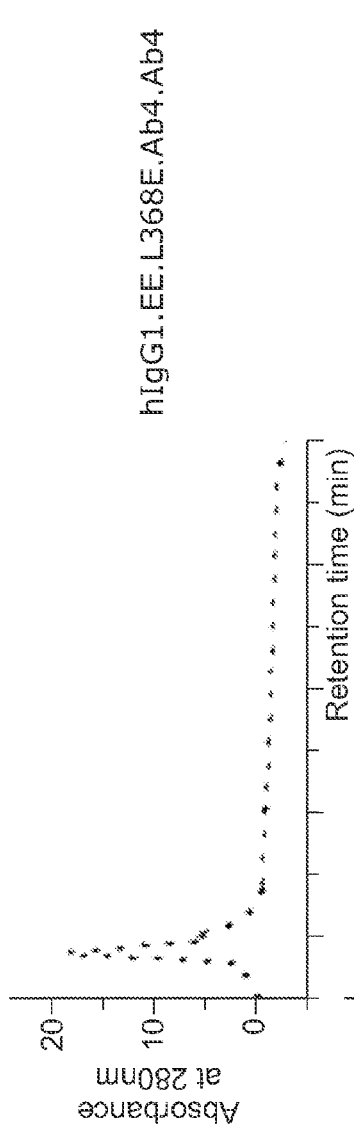
FIGS. 22A-22C depict ion exchange chromatography can be used to separate IgG1 mutant (221R, 228R, and 409R) from IgG1 (221E, 228E, and 368E) mutant even if the variable domains are the same. The heterodimer of these two variants can also be separated from the homodimers using ion exchange chromatography. Dashed line represents Ab4 antibody with 221R and 228R mutations in the hinge region and 409R mutation in the CH3 domain of the heavy chain. Dotted line represents Ab4 hIgG1 antibody with 221E and 228E mutations in the hinge and 368E in the CH3 domain. Solid line represents elution profile of the heterodimer-hIgG1.RR.K409R.Ab4.Ab4/hIgG1.EE.L368E.Ab4.Ab4.
Figure 22B:
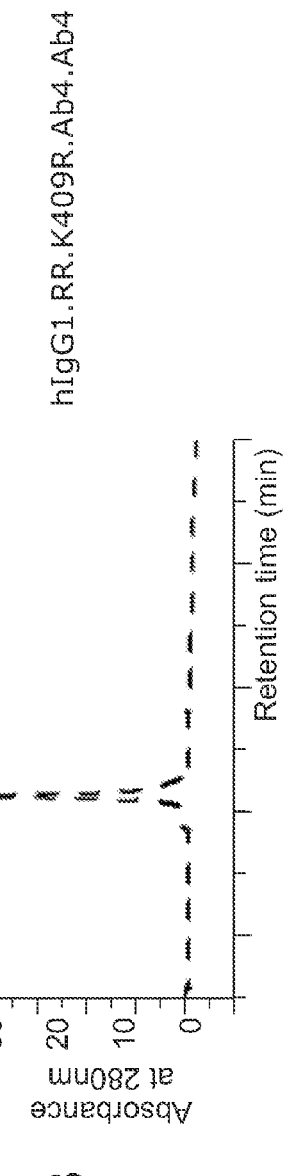
Figure 22C:
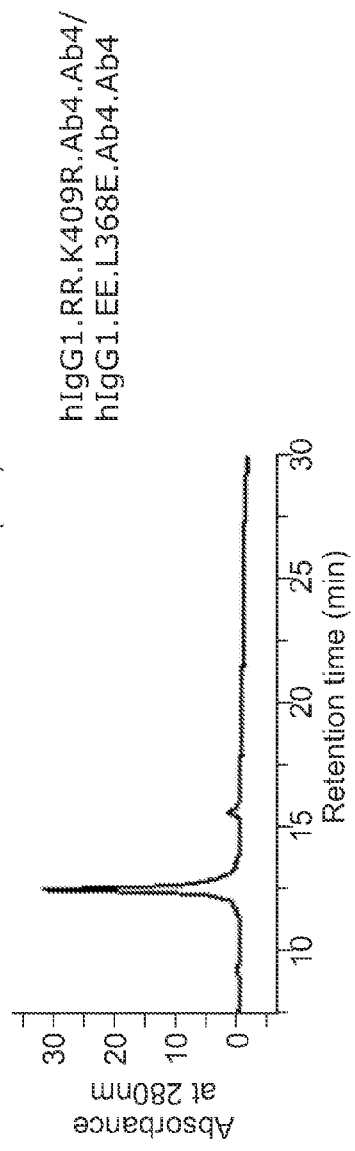
Figure 23A:
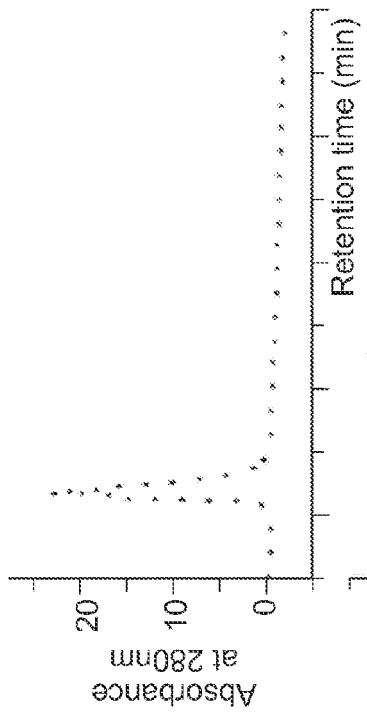
FIGS. 23A-23C depict another example that ion exchange chromatography can be used to separate IgG1 mutant (221R, 228R, and 409R) from IgG1 (221E, 228E, and 368E) mutant even if the variable domains are the same. The heterodimer of these two variants can also be separated from the homodimers using ion exchange chromatography. Dashed line represents Ab3 antibody with 221R and 228R mutations in the hinge region and 409R mutation in the CH3 domain of the heavy chain. Dotted line represents Ab3 hIgG1 antibody with 221E and 228E mutations in the hinge and 368E in the CH3 domain. Solid line represents elution profile of the heterodimer—hIgG1.RR.K409R.Ab3.Ab3/hIgG1.EE.L368E.Ab3.Ab3.
Figure 23B:
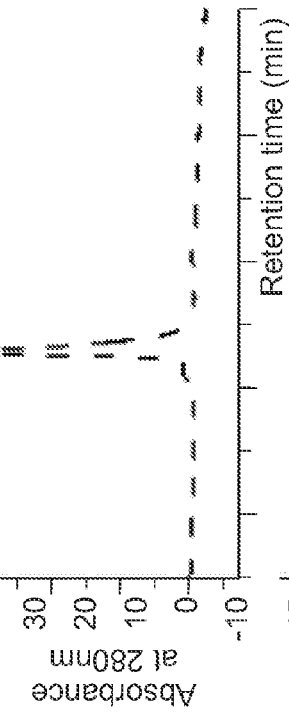
Figure 23C:
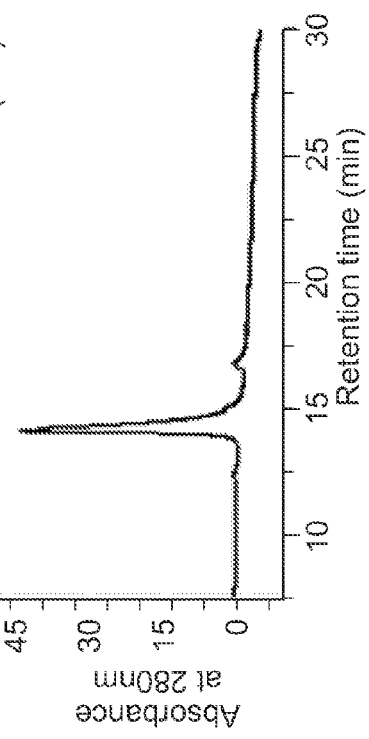

All the mutants and the wild-type controls as shown in FIG. 15B were expressed and purified individually. Equal amount of antibody 1 and antibody 2 were mixed together and incubated with or without 0.5 mM GSH at 37° C. for 24 hour. Aliquots from each GSH reactions was diluted in ice-cold PBS-TB (PBS with 0.2% BSA, 0.05% Tween-20) and the amount of bispecific antibodies was measured by sandwich ELISA as described before.

As shown in FIG. 15A, introducing mutations at two positions of the IgG1 hinge region, D221 and P228, significantly affected levels of IgG1 bispecific antibody formation. Removing the mutation in position D221 dramatically decreased bispecific antibody formation, even when combined with a CH3 mutation (column 1). Within all three isotypes, IgG1 mutants generate the greatest level of bispecific antibodies (compare columns 2, 3 and 4). Standard controls were the same as in previous examples.

Example 10

Generation and Purification of Heterodimeric Antibodies

IgG1 heterodimers were prepared by incubation of Antibody 1 having 221R, 228R, and 409R mutations with Antibody 2 having 221E, 228E, and 368E mutations in PBS with 1 mM GSH for 24 hrs at 37° C. Different antibody variable regions were used for preparation of the heterodimers, i.e., Ab1, Ab2, Ab3, and Ab4. IgG2 heterodimers were prepared by incubation of Antibody 1 having 223R, 225R, 228R, and 409R mutations with Antibody 2 having 223E, 225E, 228E, and 368E mutations in PBS with 2 mM GSH for 24 hrs at 37° C. The heterodimer was purified by ion exchange chromatography, as described below. IgG4 heterodimers were prepared by incubation of Antibody 1 with 228R mutation with Antibody 2 with 228E mutation in PBS with 1 mM GSH for 24 hrs at 37° C.

All the heterodimers were purified by ion exchange chromatography. Briefly, analytical ion exchange separation of the Fc-hetero and Fc-homodimers was carried out on Agilent 1100 quaternary pump LC system (Agilent Inc, Santa Clara, Calif., USA) equipped with weak cation exchange DIONEX Propac WCX-10G (4×50 mm) column. Proteins were injected in 5% buffer A (20 mM MES pH 5.4) and eluted in a gradient from 25% to 75% buffer B (20 mM MES pH 5.4 and 500 mM NaCl) over a 20 minute period with 1 ml/min flow rate. Larger scale Fc-heterodimer purification was performed on an Akta Explorer (GE) equipped with weak cation exchange DIONEX Propac WCX-10G (4×250 mm) column. Proteins were injected in 5% buffer A (20 mM MES pH 5.4) and eluted in a gradient from 15% to 75% buffer B (20 mM MES pH 5.4 and 500 mM NaCl) over a 60 minute period with 1 ml/min flow rate. See FIGS. 16A-23C.

Example 11

Effect of CH3 Mutations on Heterodimer Formation

Figures 24A, 24B:
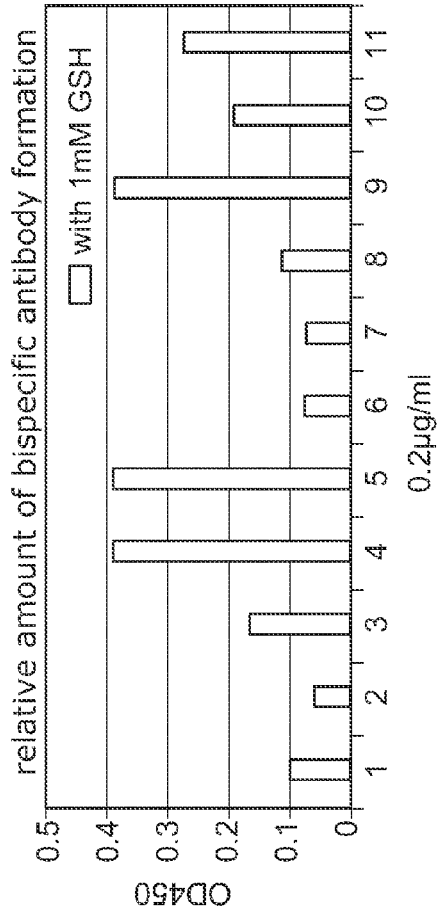
FIGS. 24A-24B depict (A) a comparison of bispecific antibody formation for the indicated mutants (B).
Figure 26A:
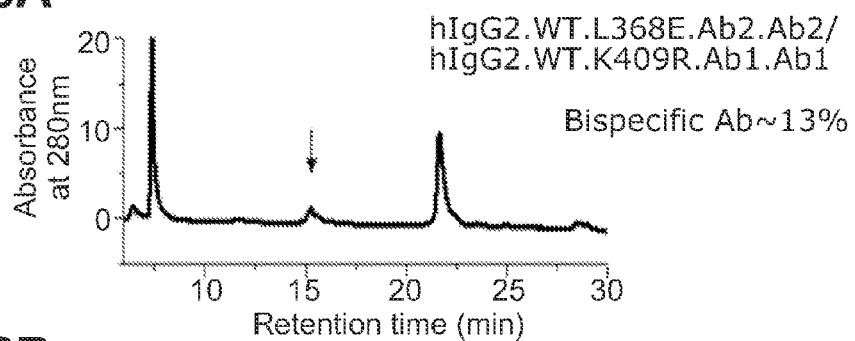
FIGS. 26A-26D depict ion exchange elution profiles of hIgG1 and hIgG2 mutants. Solid line represents elution profiles of the Ab2-Ab1 bispecific antibody reaction products formed after incubation of the Ab2 and Ab1 variants with gluthione (1 mM for hIgG1 and 2 mM for hIgG2). CH3 only mutation provides about 12% IgG1 or 13% IgG2 heterodimeric protein formation (mutations at K409R and L368E) in comparison to the wild-type hIgG1 and the combination of both the hinge (mutations at D221R, P228R, D221E, and P228E) and the CH3 mutations (mutations at K409R and L368E) provides about 90% IgG1 heterodimeric protein formation in comparison to the wild-type hIgG1.
Figure 26B:
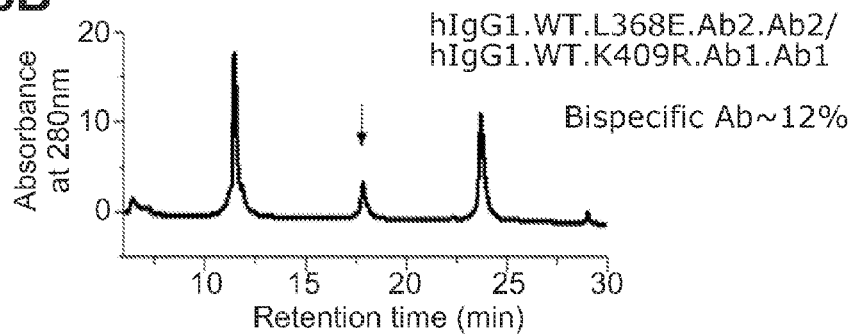
Figure 26C:
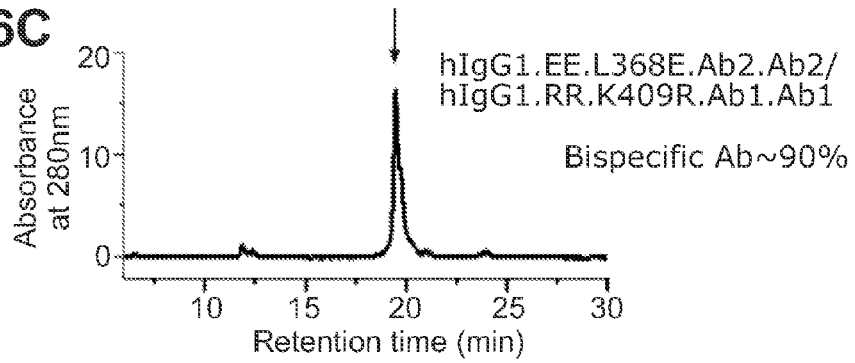
Figure 26D:
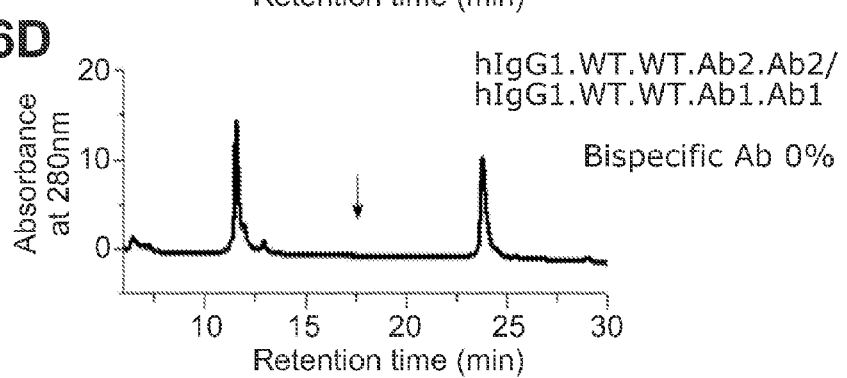

The example illustrates the effect of various CH3 and/or hinge mutations on heterodimeric protein formation.
a) CH3 Mutations at L368D, L368E, and K409R, and Wild-Type or Mutant Hinge
Plasmid vectors encoding the antibody mutants depicted in FIG. 24B were prepared using the methods described above. Antibody Ab2 is an anti-antigen B antibody comprising a lambda light chain, and Antibody Ab1 is an anti-antigen A antibody comprising a kappa light chain. In this example, where mutations were made in the IgG1 hinge, the mutations were at positions D221 and P228. Where mutations were made in the IgG2 hinge, the mutations were at C223, E225 and P228. In this example, some of the mutants contained a CH3 mutation and a wild-type (wt) hinge. Other mutants contained mutations in both the hinge and the CH3 regions. In this example, the CH3 mutations were selected from K409R, L368D, and L368E.

The Group A and Group B mutants shown in FIG. 24B were expressed and purified individually. Combination pairs 1-11 were tested for bispecific antibody formation. For each of the combinations 1-11, equal amounts of the specified Group A antibody and corresponding Group B antibody were mixed together and incubated with or without 0.5 mM GSH at 37° C. for 24 hours. Aliquots from each GSH reactions was diluted in ice-cold PBS-TB (PBS with 0.2% BSA, 0.05% Tween-20) and the amount of bispecific antibodies was measured by sandwich ELISA. To detect bispecific antibodies, 0.25 µg/ml purified total proteins from each GSH reaction were added onto an ELISA plate coated with 1 µg/ml antigen B. The amount of bispecific antibodies in each preparation was detected by HRP conjugated anti-kappa antibody.

As shown in FIG. 24A, introducing the K409R CH3 mutation in IgG1 was sufficient to promote some bispecific antibody formation (column 1). In contrast, the L368E CH3 mutation alone did not result in a significant amount of bispecific antibody formation (column 2).
b) CH3 Mutations at L368E and/or K409R, and Wild-Type or Mutant Hinge
Plasmid vectors encoding the antibody mutants depicted in FIG. 25B were prepared using the methods described above. In this example, where mutations were made in the IgG1 hinge, the mutations were at positions D221 and P228. Where mutations were made in the IgG2 hinge, the mutations were at C223, E225, and P228. In this example, some of the mutants contained a CH3 mutation and a wild-type (wt) hinge. Other mutants contained mutations in both the hinge and the CH3 regions. In this example, the CH3 mutations were selected from K409R and L368E.

The Group A and Group B mutants shown in FIG. 25B were expressed and purified individually. Combination pairs 1-15 were tested for bispecific antibody formation using the methods described above in section (a).

hIgG1 and hIgG2 heterodimers were purified by ion exchange chromatography using the method described in Example 10. FIGS. 26A-26D illustrate that the CH3 only mutation provides about 12% IgG1 or 13% IgG2 heterodimeric protein formation (mutations at K409R and L368E) in comparison to the wild type hIgG1 and that the combination of both the hinge (mutations at D221R, P228R, D221E, and P228E) and the CH3 mutations (mutations at K409R and L368E) provides about 90% IgG1 heterodimeric protein formation in comparison to the wild-type hIgG1 heterodimeric protein.

Example 12

Differential Scanning Calorimetry Measuring the Stability of the Bispecific Antibody and its Parental Mutant Monospecific Antibodies Differential Scanning calorimetry (DSC) measuring the stability of the bispecific antibodies was carried out for all antibody samples: 1) wild-type hIgG1 antibodies 5 and 6 (Ab5. wild-type hIgG1 and Ab6.wild-type hIgG1); 2) parental hIgG1 antibody 5 with hinge mutations (D221E and P228E) and CH3 mutation (L368E) and parental hIgG1 antibody 6 with hinge mutations (D228R and P228R) and CH3 mutation (K409R) (hIgG1.EE.L368E.Ab5.Ab5 or hIgG1.RR.K409R.Ab6.Ab6); and 3) bispecific hIgG1 antibody 5+6 with mutations at D221R, P228R, D221E, P228E, L368E, and K409R (hIgG1.EE.L368E.Ab5.Ab5/hIgG1.RR.K409R.Ab6.Ab6). The measurements were made at a concentration of 1.0 mg/mL at pH 7.2 in PBS buffer on a MICROCAL™ VP capillary DSC system (GE Healthcare, Piscataway, N.J., USA). Samples were scanned at a rate of 90° C./hr from 30 to 110° C. Data analysis was performed using OriginLab software (OriginLab Corporation, Northampton, Mass., USA).

Figure 27:
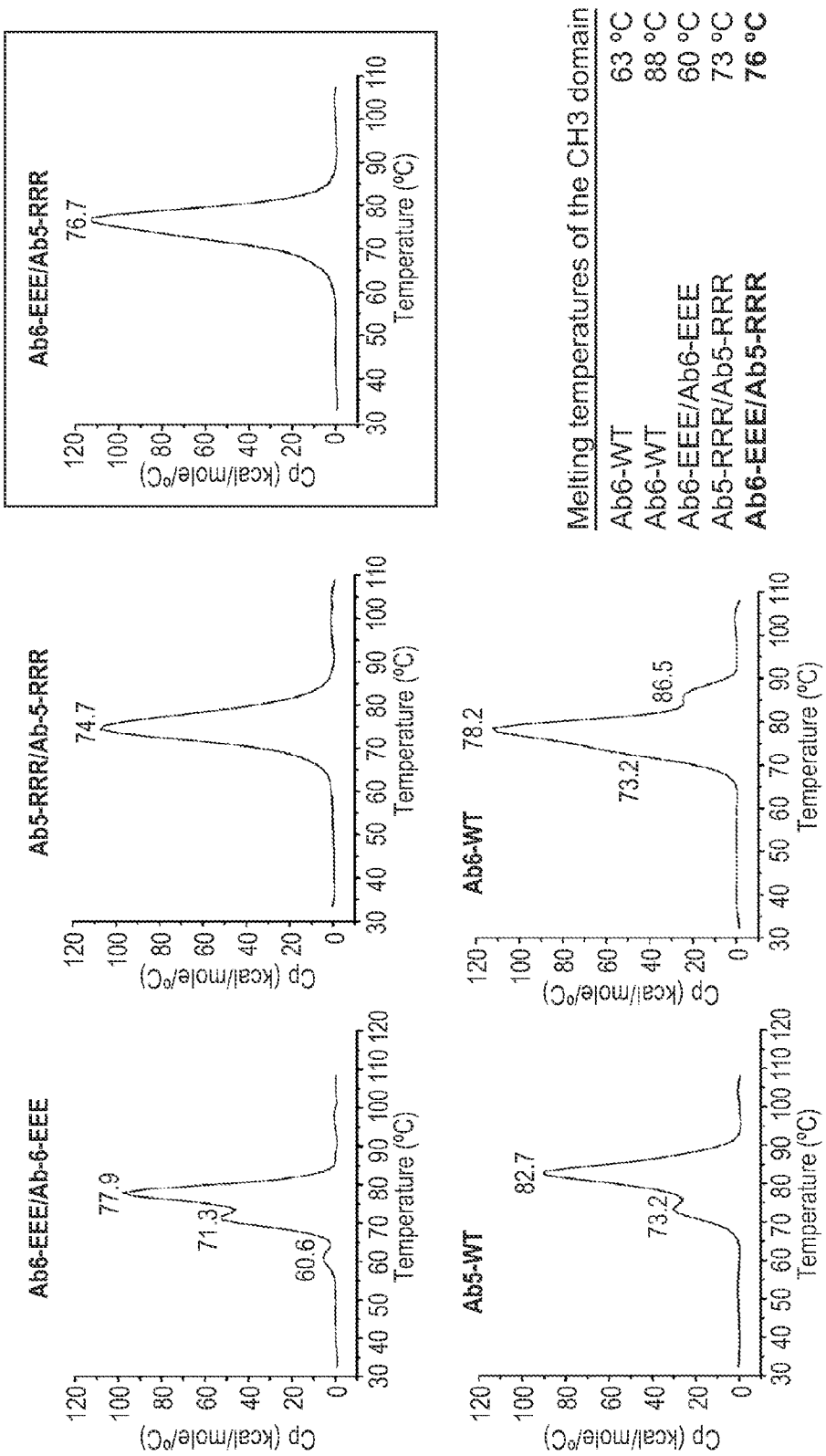
FIG. 27 depicts differential scanning calorimetry profiles for wild-type hIgG1 antibodies (Ab5 and Ab6), for parental mutant monospecific antibodies (hIgG1.RR.K409R.Ab6.Ab6/hIgG1.RR.K409R.Ab6.Ab6), and for the bispecific antibody ((hIgG1.EE.L368E.Ab5.Ab5/hIgG1.RR.K409R.Ab6.Ab6).

The wild-type hIgG1 antibodies show melting temperature (Tm) of the CH3 domain at about 86° C., while the parental hIgG1 mutant antibody 5 or 6 has reduced Tm of 60° C. The Tm of the Ab6 mutant (hIgG1.RR.K409R.Ab6.Ab6/hIgG1.RR.K409R.Ab6.Ab6) appears similar to the Fab domain with CH3 Tm at about 75° C. Upon formation of the bispecific antibody, the Tm of the CH3 domain is about 75° C. FIG. 27.

Example 13

Simultaneous Binding of Two Different Antigens by the Bispecific Antibody

This example illustrates the ability of the heterodimeric proteins disclosed herein to simultaneously bind two different antigens.
Antigens A and B
A Biacore 3000 SPR biosensor instrument (GE Healthcare, Piscataway, N.J., USA) was used for this analysis. The (antigen A)-hFc antigen was coupled to a Biacore CM5 sensor chip surface using an amine-coupling procedure. The running buffer for the immobilization procedure was HBS-T+ (10 mM HEPES, 150 mM NaCl, 0.05% Tween-20, pH 7.4). The CM5 sensor surface was activated by injecting a 1:1 (v/v) mixture of 400 mM EDC (1-ethyl-3-(3-dimethylaminopropyl)carbodiimide) and 100 mM NHS (N-Hydroxysuccinimide) for 7 minutes at 10 ul/min. Then, (antigen A)-hFc was diluted to 50 µg/mL in 10 mM acetate buffer at pH 5.0 and injected at 20 ul/min for 7 minutes. The surface was blocked by injecting 1 M ethanolamine, pH 8.5 over the sensor surface at 10 ul/min.

After immobilization, first, 2 µg/mL bispecific antibody (hIgG1.EE.L368E.Ab1.Ab1/hIgG1.RR.K409R.Ab2.Ab2; mutation at hinge region of D221R, P228R, D221E, and P228E and the CH3 region of K409R and L368E) was injected for 1 minute at 10 ul/min. Second, a "sandwiching analyte" was injected for 2 minutes at 10 ul/min. The "sandwiching analytes" tested were 972 nM antigen B, 1000 nM (antigen A)-ECD-his, and running buffer. The surfaces were regenerated with two 6-second injections of a 2:1 (v/v) mixture of Pierce Elution Buffer:4M NaCl (Thermo Fisher Scientific, Rockford, Ill., USA).

Figure 28A:
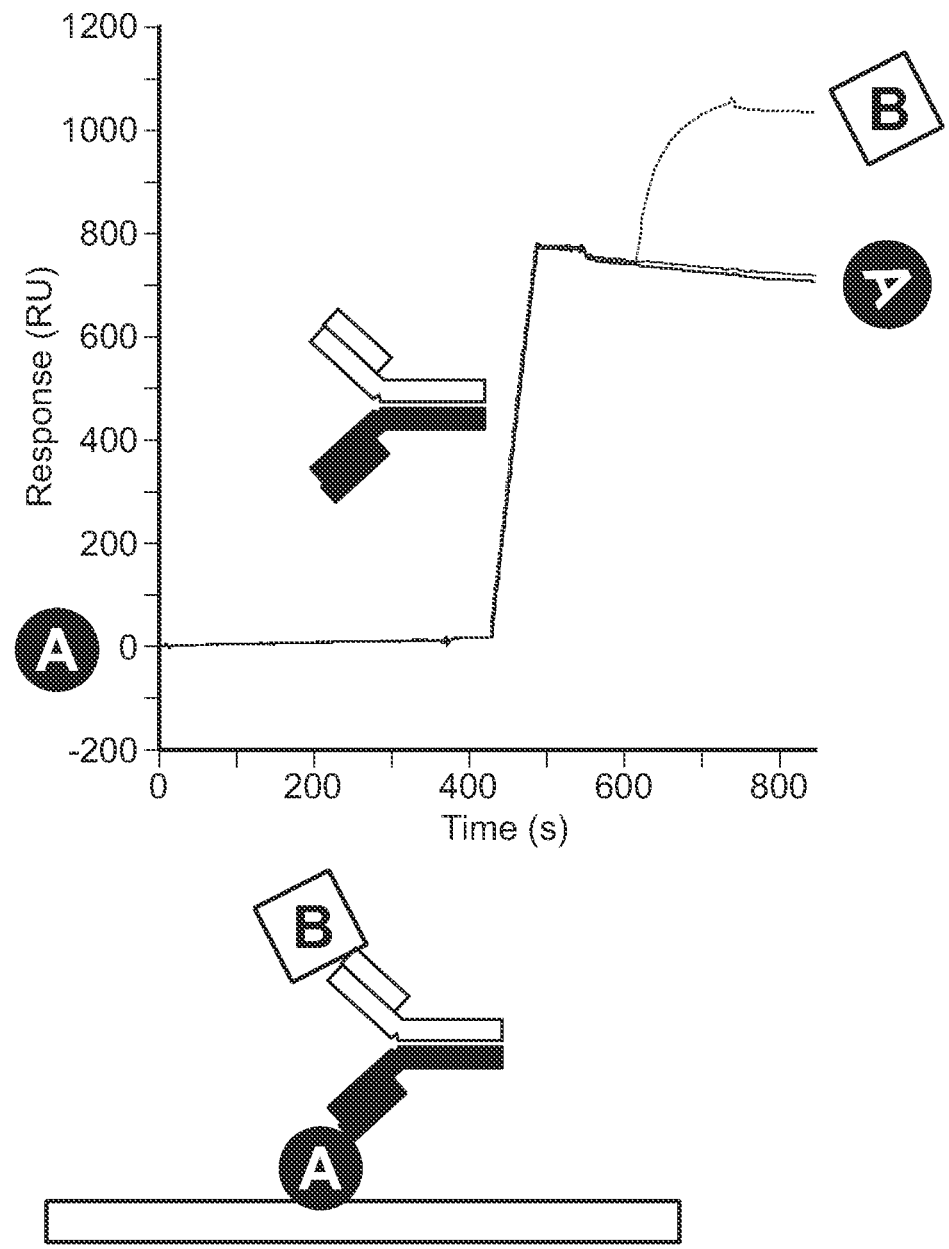

FIG. 28A shows that the bispecific antibody hIgG1EE.L368E.Ab1.Ab1/h1gG1RR.K409R.Ab2.Ab2 can simultaneously bind antigens A and B and that non-bispecific antibodies were not detected.

A similar experiment using antigen B coupling to a Biacore CM5 sensor chip surface was also conducted. All experimental conditions were the same as the (antigen A)-hFc as described above, with the exception that 2 ug/mL bispecific antibody was injected for 4 minutes, rather than 1 minute, at 10 ul/min. The bispecific antibody was also able to simultaneously bind antigens A and B.

Antigens C and D

A Biacore 3000 SPR biosensor instrument was also used for this analysis. The (antigen D)-hFc was coupled to a Biacore CM5 sensor chip surface using an amine-coupling procedure. The running buffer for the immobilization procedure was also HBS-T+. The CM5 sensor surface was activated by injecting a 1:1 (v/v) mixture of 400 mM EDC and 100 mM NHS for 7 minutes at 10 ul/min. Then, (antigen D)-hFc was diluted to 30 µg/mL in 10 mM sodium phosphate buffer at pH 6.5 and injected at 20 ul/min for 7 minutes. The surface was blocked by injecting 1 M ethanolamine at pH 8.5 over the sensor surface at 10 uL/min.

After immobilization, the running buffer was changed to HBS-T+ with 1 mg/mL BSA (10 mM HEPES, 150 mM NaCl, 0.05% Tween 20, 1 mg/mL BSA, pH 7.4). First, 1 µg/mL bispecific antibody (hIgG1EE.L368E.Ab4.Ab4/h1gG1RR.K409R.Ab3.Ab3; mutation at hinge region of D221R, P228R, D221E, and P228E and the CH3 region of K409R and L368E) was injected for 2 minutes at 10 ul/min Second, a "sandwiching analyte" was injected for 2 minutes at 10 ul/min. The "sandwiching analytes" tested were 20 nM antigen C, 200 nM (antigen-D)-ECD-his, and running buffer. The surfaces were regenerated with two 15-second injections of a 2:1 (v/v) mixture of Pierce Elution Buffer:4M NaCl.

FIG. 28B shows that the bispecific antibody hIgG1EE.L368E.Ab4.Ab4/h1gG1RR.K409R.Ab3.Ab3 can simultaneously bind antigens D and C and that non-bispecific antibodies were not detected.

A similar experiment using (antigen C)-hFc coupling to a Biacore CM5 sensor chip surface was also conducted. All experimental conditions were the same as the (antigen D)-hFc as described above, with the exception that (antigen C)-hFc was diluted to 10 µg/mL in 10 mM acetate buffer at pH 5.0, rather than 30 ug/mL in 10 mM sodium phosphate buffer pH 6, and injected at 20 ul/min for 7 minutes. The bispecific antibody was also able to simultaneously bind antigens C and D.

Example 14

Binding of the Bispecific Antibody to Fc-Gamma and FcRn Receptors

This example illustrates the ability of the heterodimeric proteins disclosed herein to bind Fc receptors.

Interaction analysis was conducted at 25° C. using a PROTEON™ XPR36 surface plasmon resonance-based biosensor equipped with GLC sensor chips and amine-coupling reagents (BioRad, Hercules, Calif.). The running buffer for the immobilizations and the analysis of the Fc-gamma-receptors was PBS pH7.4+0.05% Tween-20. Buffer was flowed at 30 uL/min. A panel of IgGs were amine-coupled onto separate "ligand" channels to levels of about 300-700 RU using a standard EDC/sulfo-NHS-mediated chemistry. The IgGs include bispecific hIgG1 antibody 1+2 with mutations at D221R, P228R, D221E, P228E, L368E, and K409R (hIgG1.EE.L368E.Ab1.Ab1/hIgG1.RR.K409R.Ab2.Ab2); hIgG2 antibody 1+2 with mutations at C223E, E225E, P228E, C223R, E225R, P228R, L368E, and K409R (hIgG2.EEE.L368E.Ab1.Ab1/hIgG2.RRR.K409R.Ab2.Ab2); and hIgG1 and hIgG2 antibodies comprising a kappa light chain (Sigma-Aldrich, St. Louis, Mo., USA). Briefly, this involved activating for two minutes with a mixture of the stock solutions (supplied at 0.4M EDC and 0.1M sulfo-NHS) each diluted 1/600 in water, coupling the IgGs for three minutes at 20 ug/mL in 10 mM sodium acetate at pH4.5, and finally deactivating any excess reactive groups for three minutes with 1M ethanolamine.HCl at pH8.5. The Fc-gamma-receptors were each prepared as a five-fold serial dilution with a variable top concentration, which was optimized per receptor (typically 200 nM for human Fc-gamma1 and 10 uM for the other receptors). A five-membered serial dilution of each receptor including a buffer blank was injected in the "analyte" direction for three minutes in a "one-shot" mode, allowing up to 30 minutes dissociation time. For receptors that did not dissociate fully within the allowed dissociation time, surfaces were regenerated at 100 uL/min with two 18-sec injections of a 2:1 (v/v) mixture of Pierce Gentle Elution Buffer/4M NaCl (Thermo Scientific, Rockford, Ill., USA). Some receptors were injected in duplicate binding cycles to verify that the assay was reproducible.

The interactions of the immobilized IgGs with human-FcRn (neonatal Fc receptor) were conducted in a different manner. The IgGs used are the same bispecific hIgG1 and hIgG2 antibodies 1+2 as described above. The control antibody used is a human IgG2ΔA. The IgGs were coupled onto separate reaction spots rather than channels (Abdiche et al, *Anal. Biochem.* 411(1):139-151 (2011)), the analysis running buffer was PBS+0.05% Tween-20 pH6.0, and the human-FcRn was injected in a kinetic titration mode as both a five-fold and three-fold dilution series, each with a top concentration at 900 nM. Association and dissociation times were three and five minutes respectively and no regeneration was required. Data processing and analysis were performed within the PROTEON™ Manager software v 2.1. Response data for each interaction were double referenced by subtracting the responses from the interspots (unmodified chip) and the responses from the buffer blanks, and then fit globally to a simple Langmuir kinetic model. The equilibrium dissociation constant ($K_D$) was deduced from the ratio of the kinetic rate constants ($K_D=k_d/k_a$). For interactions that rapidly reached equilibrium binding responses within the association phase, the $K_D$ was deduced via an equilibrium binding model.

Table 4 shows that binding of IgG1 and IgG2 bispecific antibodies to Fc-gamma (Fcγ) receptors is similar to the control hIgG1 and hIgG2 antibodies. Table 5 shows that FcRn binding of IgG1 and IgG2 bispecific antibodies is also similar to the control hIgG2ΔA antibody.

TABLE 4

| | Fcγ receptors (in solution) | | | | | | | |
|---|---|---|---|---|---|---|---|---|
| IgG coupled | hFcγ1 | hFcγ2A | hFcγ2B | hFcγ3A | hFcγ3B | mFcγ1 | mFcγ2B | mFcγ3 |
| hIgG1 kappa (control) | 0.2 nM | weak | 3 uM | 272 nM | weak | 120 nM | weak | weak |
| hIgG1.EE.L368E.Ab1.Ab1/hIgG1.RR.K409R.Ab2.Ab2 | 0.4 nM | weak | 6 uM | 671 nM | weak | 260 nM | weak | weak |
| hIgG2 kappa (control) | none | very weak | >10 uM | 1930 nM | very weak | none | very weak | very weak |
| hIgG2.EEE.L368E.Ab1.Ab1/hIgG2.RRR.K409R.Ab2.Ab2 | none | very weak | >10 uM | none | none | none | none | none |

TABLE 5

| IgG coupled | Kd (uM) |
|---|---|
| hIgG1.EE.L368E.Ab1.Ab1/hIgG1.RR.K409R.Ab2.Ab2 | 0.826 |
| hIgG2.EEE.L368E.Ab1.Ab1/hIgG2.RRR.K409R.Ab2.Ab2 | 0.60 |
| hIgG2ΔA (control) | 0.983 |

Example 15

In Vitro Growth Inhibition Assay and Off-Rate Measurement of the Bispecific Antibody This example illustrates the ability of a heterodimeric protein to inhibit cell growth in vitro.

In vitro activity of the Ab3+Ab4 IgG1 bispecific antibody on cell growth in comparison to its parental bivalent monospecific antibodies as well as their monovalent counterparts was determined Growth Inhibition Assay Cal27 tongue carcinoma cells or FaDu head and neck carcinoma cells were seeded at 3000 cells/well in RPMI 1640 medium+2% FBS (fetal bovine serum) and grown in the 96-well plate overnight. A serial dilution of antibodies in RPMI 1640 medium+2% FBS was then added to each well and cells were allowed to grow for 5 days at 37° C. At the end of the assay, the amount of cells was measured by the Cell Titer Glo kit (Promega, Madison, Wis., USA) as per manufacturer's protocol. The amount of cells for each antibody concentration was normalized to that of control human IgG1 treatment and used to generate the dose-response curve. All samples were performed in triplicate.

Cell-Based Antibody Dissociation Rate Constant Measurement

Cal27 tongue carcinoma cells were grown on poly-D-lysine coated 96-well plate in DMEM+10% FBS until near confluent. Wells were washed with PBS and followed by 2% paraformaldehyde fixation for 15 minutes at room temperature. All subsequent incubation was done at room temperature. For immunofluorescent staining, wells were blocked with DMEM/B (DMEM+5% BSA) for 1 hour. Dylight800-labeled (labeling kit from Thermo Scientific, Rockford, Ill., USA) target-specific antibodies diluted in DMEM/B were added to wells and incubated for 1 hour. Wells were then washed three times with 250 ul DMEM/B. To measure antibody-antigen dissociation, 150 ul of 50 ug/ml unlabeled target-specific antibodies was added to each well (except those for timepoint "0") and incubated at room temperature for various time for up to 21 hours. At the end of incubation, antibody solution was discarded and replaced with 100 ul of 10 uM DRAQ5™ (Biostatus Limited, United Kingdom) and further incubated for 8 minutes. Subsequently, DRAQ5™ solution was discarded, and wells were air-dried while protected from light. For timepoint "0", wells were directly stained with DRAQ5™ without incubation with unlabeled antibodies. All samples were done in triplicate.

Plate was then read by Li-Cor ODYSSEY® infrared imaging system (LI-COR Biotechnology, Lincoln, Nebr.) to measure the fluorescent intensity at 800 nm, which corresponded to the amount of Dylight800-labeled antibody remained bound on cell surface, and 700 nm (DRAQ5), which stained DNA and hence correlated with the number of cells in each well. For each well, the fluorescent intensity at 800 nm was normalized by the value at 700 nm to account for the well-to-well variation of total cell number. Subsequently, the normalized fluorescent intensity for each well was normalized again by the corresponding value at time point "0" and then plotted against dissociation time to generate an exponential decay curve. The curve was then fitted to a single exponential decay equation using GraphPad Prism to generate the apparent dissociation rate constant.

Ab3/Ab4 Bispecific Antibody Effectively Inhibits Growth of Cal27 and FaDu Cells

To investigate the in vitro activity of Ab3/Ab4 bispecific antibody on cell growth, the bispecific antibody was compared to their parental bivalent, monospecific antibodies as well as their monovalent counterparts. As shown in FIG. 29, monovalent Ab4/nc.biFc (hIgG1.RR.K409R.Ab4.Ab4/hIgG1.EE.L368E.Ab6.Ab6; mutations at D221R, P228R, D221E, P228E, L368E, and K409R) as well as bivalent Ab4.hIgG1 (Ab4.wild-type hIgG1) had no significant effect on cell growth across all concentrations tested while monovalent Ab3/nc.Fc (hIgG1.RR.K409R.Ab3.Ab3/hIgG1.EE.L368E.Ab6.Ab6; mutations at D221R, P228R, D221E, P228E, L368E, and K409R) inhibited (>10%) growth of Cal27 and FaDu cells at concentration >1 ug/ml. Yet, when the negative control (nc) arm of the monovalent Ab3/nc.biFc antibody was replaced by Ab4 to generate the bispecific antibody (hIgG1.EE.L368E.Ab3.Ab3/hIgG1.RR.K409R.Ab4.Ab4), it significantly augmented the growth inhibitory activity of the Ab3 arm to a level that was comparable to the bivalent monospecific Ab3 antibodies (Ab3.hIgG1 and Ab3.biFc). This effect is hypothesized due to gain in avidity as a result of binding of the Ab4 arm to its cell surface target and thus increases the local concentration of Ab3 on cell surface and hence the occupancy of Ab3 target. FIG. 29.

Figure 30:
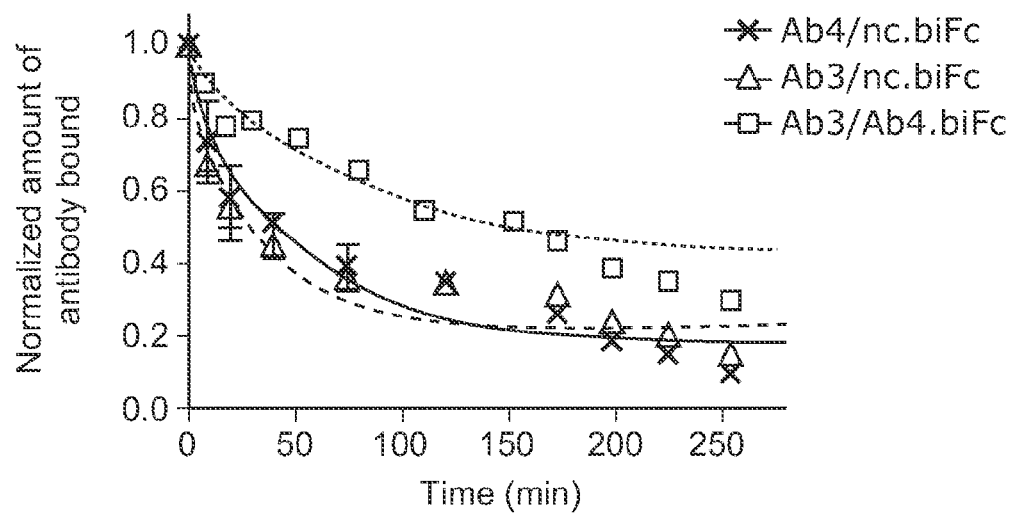
FIG. 30 shows the dissociation rate constants of monovalent and bispecific Ab3 and Ab4 antibody measured in Cal27 cells. Bispecific Ab3/Ab4 antibody (black square) is the bispecific mutant antibody (hIgG1.EE.L368E.Ab3.Ab3/hIgG1.RR.K409R.Ab4.Ab4). Ab4/nc.biFc (cross) is the monovalent Ab4 with a negative control (non-specific) antibody (Ab6) in one arm (hIgG1.RR.K409R.Ab4.Ab4/hIgG1.EE.L368E.Ab6.Ab6). Ab3/nc.biFc (open triangle) is the monovalent Ab3 with a negative control antibody (Ab6) on one arm (hIgG1.RR.K409R.Ab3.Ab3/hIgG1.EE.L368E.Ab6.Ab6). Solid and dotted lines are fit to a single exponential equation.

Ab3/Ab4 Bispecific Antibody has a Slower Apparent Dissociation Rate Constant than its Monovalent Counterparts To obtain evidence of avidity gain in the bispecific antibody, the apparent dissociation rate constants of the bispecific antibody and its monovalent counterparts were measured on Cal27 cells. As shown in FIG. 30, the apparent dissociation rate constant of Ab3/Ab4.biFc (hIgG1.EE.L368E.Ab3.Ab3/hIgG1.RR.K409R.Ab4.Ab4) was about 2-fold slower than that of the monovalent antibodies, Ab3/nc.biFc (hIgG1.RR.K409R.Ab3.Ab3/ hIgG1.EE.L368E.Ab6.Ab6) and Ab4/nc.biFc (hIgG1.RR.K409R.Ab4.Ab4/hIgG1.EE.L368E.Ab6.Ab6). Taken together, the data suggest that the bispecific antibody gained avidity through binding of both Ab3 and Ab4 arms to cell surface.

Example 16

In Vivo Efficacy Studies of the Bispecific Antibody on Target-Expressing Cell Xenograft Models This example illustrates the in vivo efficacy of heterodimeric proteins prepared using the methods described herein.

In vivo efficacy studies of bispecific antibodies are performed on target-expressing cell xenograft models compared to wild-type bivalent monospecific antibodies. More specifically, subcutaneous tumor growth curves (representing tumor types including, but not limited to, pancreatic, head and neck, colon, gastric, breast, prostate or lung cancer) in immunodeficient nu/nu or SCID (Severely Combined Immunodeficient) mice are established prior to efficacy studies to obtain optimal cell numbers for tumor implantation. A typical efficacy is carried out in the following steps: 1) Tumor cells are implanted subcutaneously into 5-8 weeks old immunodeficient mice until the tumor sizes reach 50-100 mm$^3$, 2) Dosing is done through bolus tail vein injection. Depending on the tumor response to treatment, animals are injected with 1-100 mg/kg of bispecific (e.g., hIgG1.EE.L368E.Ab4.Ab4/h1gG1.RR.K409R.Ab3.Ab3; mutations at D221R, P228R, D221E, P228E, L368E, and K409R) or wild-type antibodies (hIgG1 Ab3 or hIgG1 Ab4) up to three times a week. 3) Dosing continues until the tumor sizes in the control group reach 2000 mm$^3$. All experimental animals are monitored for body weight changes daily. Tumor volume is measured twice a week by a Caliper device and calculated with the following formula: Tumor volume=(length×width)/2. Efficacy is expressed as the percentage tumor growth inhibition (% TGI); calculated using the equation 100−(T/C×100), where T is the MTV (median tumor volume) of the treatment group and C is the MTV of the control group. The bispecific antibodies are as efficacious as the wild-type bivalent monospecific antibodies in tumor growth inhibition. Further, with reduced affinity to normal tissues, the MTD (maximum tolerated doses) for bispecific antibodies is higher, thereby resulting in greater Therapeutic Indices defined as maximum tolerated dose/minimum curative dose.

Example 17

In Vivo Study of the Bispecific Antibody on T-Cell Mediated Killing of CD20 Positive B Cells This example illustrates the in vivo efficacy of the bispecific antibody as described herein on T-cell mediated killing of CD20 positive B cells.

The full-length bispecific antibodies (IgG2ΔA) that are specific to mouse CD20 and CD3 (e.g., hIgG2.EEE.L368E.CD3.CD3/hIgG2.RRR.K409R.CD20.CD20 (mutations at C223E, E225E, P228E, C223R, E225R, P228R, L368E, and K409R)) were generated using the methods described herein. A dose response experiment was done in wild-type C57/B16 mice, and CD19 positive lymphocytes were measured in peripheral blood 5 days after a single intravenous dose of the bispecific CD3/CD20 antibody. Doses of 200 μg/kg or greater effectively depleted the population of CD19 positive lymophocytes. See Table 6.

TABLE 6

| | CD19 (+) lymphocytes (%) | |
|---|---|---|
| Dose | Pre-bleed | Day 5 |
| PBS | 40.9 | 41.8 |
| PBS | 31.5 | 46.2 |
| PBS | 51.4 | 37 |
| PBS | 36.9 | 30.1 |
| PBS | 43.9 | 35.1 |
| 8 μg/kg | 43.9 | 39.1 |
| 8 μg/kg | 41.1 | 38.8 |
| 8 μg/kg | 37.5 | 25.8 |
| 40 μg/kg | 45.4 | 32.7 |
| 40 μg/kg | 37.3 | 28.6 |
| 40 μg/kg | 51 | 42.7 |
| 200 μg/kg | 43.1 | 3.49 |
| 200 μg/kg | 48.6 | 1.56 |
| 200 μg/kg | 41.5 | 0.74 |
| 1 mg/kg | 47.5 | 0 |
| 1 mg/kg | 50.5 | 0 |
| 1 mg/kg | 37.6 | 0 |
| 5 mg/kg | 44.5 | 0 |
| 5 mg/kg | 37.2 | 0 |
| 5 mg/kg | 43 | 0 |

Example 18

In Vitro Study of the Bispecific Antibodies on T-Cell Mediated Killing of EpCAM Positive Tumor Cells This example illustrates the ability of a heterodimeric protein to kill tumor cells mediated by cytotoxic T cells in vitro.

Figure 31A:
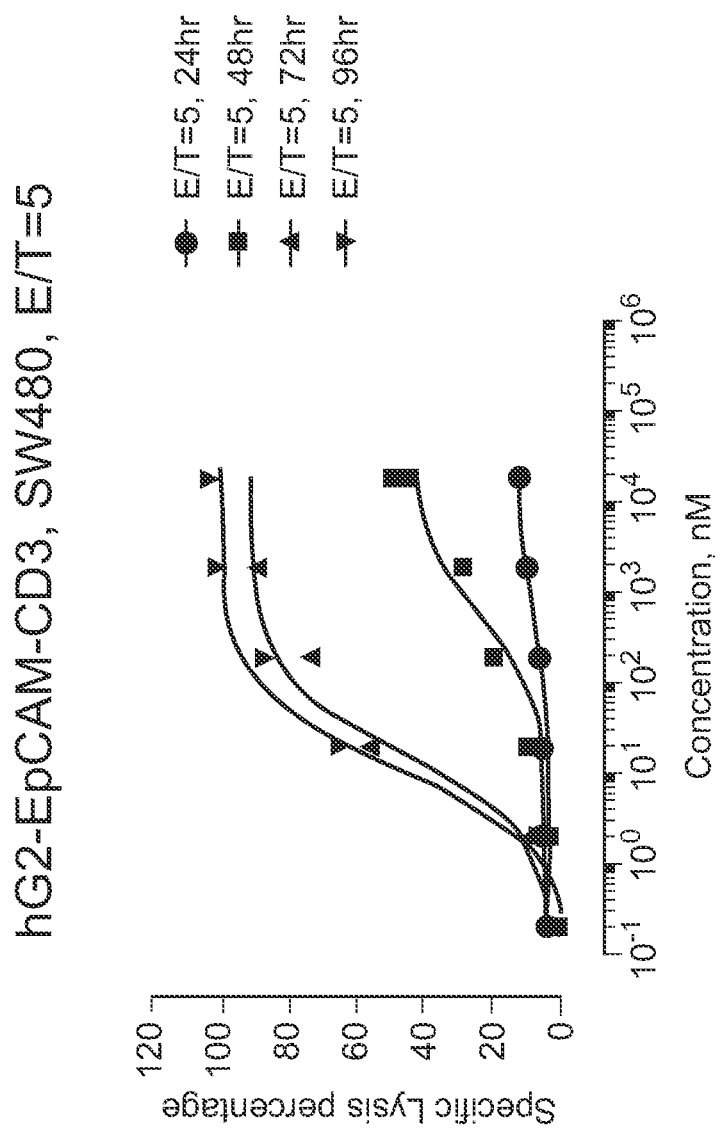
FIGS. 31A and 31B show that the ability of a heterodimeric protein (bispecific EpCAM/CD3 antibody ((labeled as "hG2-EpCAM-CD3" in the figures)) to kill tumor cells (SW480) was mediated by cytotoxic T cells in vitro. E/T denotes the ratio between the effector cells and the target cells.
Figure 31B:
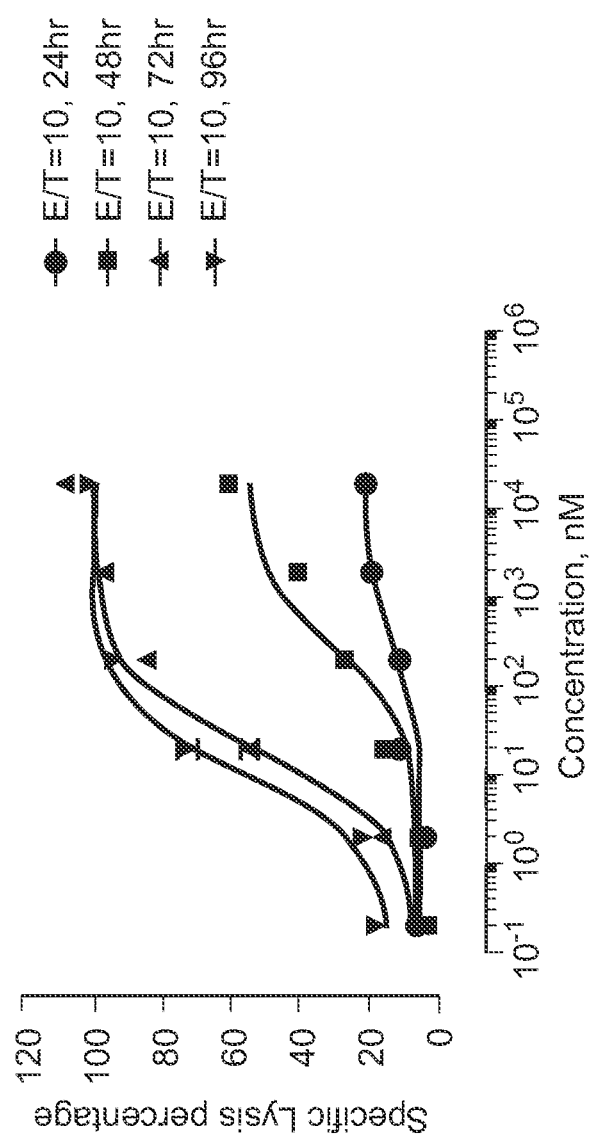

The full-length human bispecific IgG2ΔA antibody specific to EpCAM and CD3 (e.g., hIgG2.EEE.L368E.EpCAM.EpCAM/hIgG2.RRR.K409R.CD3.CD3 (mutations at C223E, E225E, P228E, C223R, E225R, P228R, L368E, and K409R)) were generated using the methods described herein. The efficacy of the bispecific EpCAM/CD3 antibody was determined by using the cell killing assay set at different effector and target cell ratio (e.g., E/T 5 and E/T 10) and a 4-day time course (e.g., measured at 24, 48, 72, 96 hours). The EpCAM positive tumor cells (SW480) were used as the target cells and the PBMC (peripheral blood mononuclear cells) were isolated from healthy donor blood as effector cells. The cytotoxic potential of the bispecific EpCAM/CD3 antibody was assessed by CYTOTOX96® Non-Radioactive Cytotoxicity Assay (Promega, Madison, Wis., USA). FIGS. 31A and 31B show that the bispecific EpCAM/CD3 antibody generated in this example induced the killing of EpCAM positive tumor cells (SW480). More specifically, after co-culturing the SW480 cells with PBMC for at least 72 hours, significant lysis of the SW480 cells was observed after the addition of the bispecific EpCAM/CD3 antibody (labeled as "hG2-EpCAM-CD3" in the figures) at 10 nM. The SW480 cells were quantitatively killed at a concentration greater than 200 nM. Similar cell-lysis results using the bispecific EpCAM/CD3 IgG1 antibody (e.g., hIgG1.EE.L368E.EpCAM.EpCAM/h1gG1.RR.K409R.CD3.CD3; mutations at D221R, P228R, D221E, P228E, L368E, and K409R) were also observed.

Although the disclosed teachings have been described with reference to various applications, methods, and compositions, it will be appreciated that various changes and modifications can be made without departing from the teachings herein and the claimed invention below. The foregoing examples are provided to better illustrate the disclosed teachings and are not intended to limit the scope of the teachings presented herein. While the present teachings have been described in terms of these exemplary embodiments, the skilled artisan will readily understand that numerous variations and modifications of these exemplary embodiments are possible without undue experimentation. All such variations and modifications are within the scope of the current teachings.

All references cited herein, including patents, patent applications, papers, text books, and the like, and the references cited therein, to the extent that they are not already, are hereby incorporated by reference in their entirety. In the event that one or more of the incorporated literature and similar materials differs from or contradicts this application, including but not limited to defined terms, term usage, described techniques, or the like, this application controls.

The foregoing description and Examples detail certain specific embodiments of the invention and describes the best mode contemplated by the inventors. It will be appreciated, however, that no matter how detailed the foregoing may appear in text, the invention may be practiced in many ways and the invention should be construed in accordance with the appended claims and any equivalents thereof.

What is claimed is:

1. A heterodimeric protein comprising:
a hinge region comprising a first immunoglobulin-like hinge polypeptide and a second immunoglobulin-like hinge polypeptide which interact together to form a dimeric hinge interface, wherein electrostatic interactions between one or more charged amino acids within the hinge interface favor interaction between the first and second hinge polypeptides over interaction between two first hinge polypeptides or two second hinge polypeptides, thereby promoting heterodimer formation over homodimer formation, wherein the hinge region is a human IgG2 hinge region, wherein the first hinge polypeptide comprises at least one amino acid modification relative to a wild-type IgG hinge region; wherein the wild-type amino acid in the first hinge polypeptide is replaced with an amino acid having an opposite charge to the corresponding amino acid in the second hinge polypeptide, wherein the amino acid modification in the hinge region is at a position selected from the group consisting of Cys223 and Glu225 as shown at FIG. 6A, and further comprising an immunoglobulin-like CH3 region comprising a first CH3 polypeptide fused to the first hinge polypeptide and a second CH3 polypeptide fused to the second hinge polypeptide, wherein the first CH3 polypeptide and the second CH3 polypeptide comprise at least one amino acid modification relative to a wild-type IgG2 CH3 region sequence at a position selected from the group consisting of Leu368 and Lys409 (EU numbering scheme) as shown at FIG. 10.

2. The heterodimeric protein of claim 1, wherein the amino acid modifications in the hinge region are selected from the group consisting of Lys, Arg, Asp, and Glu.

3. The heterodimeric protein of claim 2, wherein: the first hinge polypeptide comprises Cys223Arg or Cys223Glu, and Glu225Arg or Glu225, and the first CH3 polypeptidee comprises Lys409Arg or Leu368Glu, and the second hinge polypeptide comprises Cys223Arg or Cys223Glu, and Glu225Arg or Glu225, and the second CH3 polypeptide comprises Lys409Arg or Leu368Glu, wherein the amino acids at positions 223 and 225 of the first hinge polypeptide and positions 368 and 409 of the first CH3 polypeptides are not the same as the corresponding amino acids in the second hinge and CH3 polypeptides.

4. The heterodimeric protein of claim 1, wherein the heterodimeric protein is selected from the group consisting of an antibody, a maxibody, a monobody, a peptibody, and an Fc fusion protein.

5. The heterodimeric protein of claim 4, wherein the heterodimeric protein is a monospecific monovalent, a bispecific monovalent, or a bispecific bivalent antibody.

6. A pharmaceutical composition comprising the heterodimeric protein of claim 1 and a carrier.

7. The heterodimeric protein of claim 1, wherein the heterodimeric protein is a full-length human antibody, wherein a first antibody variable domain of the heterodimeric protein is capable of recruiting the activity of a human immune effector cell by specifically binding to an antigen located on the human immune effector cell, wherein a second antibody variable domain of the heterodimeric protein is capable of specifically binding to a target antigen.

8. The heterodimeric protein of claim 3, wherein: the first hinge polypeptide comprises Cys223Arg and Glu225Arg, and the first CH3 polypeptide comprises Lys409Arg or Leu368Glu, and the second hinge polypeptide comprises Cys223Glu and Glu225, and the second CH3 polypeptide comprises Lys409Arg or Leu368Glu, wherein the amino acids at positions 223 and 225 of the first hinge polypeptide and positions 368 and 409 of the first CH3 polypeptides are not the same as the corresponding amino acids in the second hinge and CH3 polypeptides.

9. The heterodimeric protein of claim 3, wherein:
the first hinge polypeptide comprises Cys223Arg or Cys223Glu, and Glu225Arg, and the first CH3 polypeptide comprises Lys409Arg or Leu368Glu, the second hinge polypeptide comprises Cys223Arg or Cys223Glu, and Glu225, and the second CH3 polypeptide comprises Lys409Arg or Leu368Glu, wherein the amino acids at positions 223 and 225 of the first hinge polypeptide and positions 368 and 409 of the first CH3 polypeptides are not the same as the corresponding amino acids in the second hinge and CH3 polypeptides.

10. The heterodimeric protein of claim 3, wherein the first hinge polypeptide further comprises Pro228Arg or Pro228Glu as shown at FIG. 6A.

* * * * *

```
                         SEQUENCE LISTING

<160> NUMBER OF SEQ ID NOS: 60

<210> SEQ ID NO 1
<211> LENGTH: 989
<212> TYPE: DNA
<213> ORGANISM: Artificial Sequence
<220> FEATURE:
<223> OTHER INFORMATION: lgG2 Delta A

<400> SEQUENCE: 1
gcctccacca agggcccatc tgtcttccca ctggccccat gctcccgcag cacctccgag      60
agcacagccg ccctgggctg cctggtcaag gactacttcc cagaacctgt gaccgtgtcc     120
tggaactctg gcgctctgac cagcggcgtg cacaccttcc cagctgtcct gcagtcctca     180
ggtctctact ccctcagcag cgtggtgacc gtgccatcca gcaacttcgg cacccagacc     240
tacacctgca acgtagatca caagccaagc aacaccaagg tcgacaagac cgtggagaga     300
aagtgttgtg tggagtgtcc accttgtcca gcccctccag tggccggacc atccgtgttc     360
ctgttccctc caaagccaaa ggacaccctg atgatctcca gaacccagac ggtgacctgt     420
gtggtggtgg acgtgtccca cgaggaccca gaggtgcagt tcaactggta tgtggacgga     480
gtggaggtgc acaacgccaa gaccaagcca agagaggagc agttcaactc caccttcaga     540
gtggtgagcg tgctgaccgt ggtgcaccag gactggctga acggaaagga gtataagtgt     600
aaggtgtcca caagggact gccatccagc atcgagaaga ccatctccaa gaccaaggga     660
cagccaagag agccacaggt gtataccctg cccccatcca gagaggagat gaccaagaac     720
caggtgtccc tgacctgtct ggtgaaggga ttctatccat ccgacatcgc cgtggagtgg     780
gagtccaacg gacagccaga gaacaactat aagaccaccc ctccaatgct ggactccgac     840
ggatccttct tcctgtattc caagctgacc gtggacaagt ccagatggca gcagggaaac     900
gtgttctctt gttccgtgat gcacgaggcc ctgcacaacc actatacccc gaagagcctg     960
tccctgtctc cgggtaaata ggcggccgc                                      989

<210> SEQ ID NO 2
<211> LENGTH: 20
<212> TYPE: DNA
<213> ORGANISM: Artificial Sequence
<220> FEATURE:
<223> OTHER INFORMATION: PCR primer

<400> SEQUENCE: 2
gcctccacca agggcccatc                                                 20

<210> SEQ ID NO 3
<211> LENGTH: 19
```

<212> TYPE: DNA
<213> ORGANISM: Artificial Sequence
<220> FEATURE:
<223> OTHER INFORMATION: PCR primer

<400> SEQUENCE: 3
ctttctctcc acggtcttg                                         19

<210> SEQ ID NO 4
<211> LENGTH: 60
<212> TYPE: DNA
<213> ORGANISM: Artificial Sequence
<220> FEATURE:
<223> OTHER INFORMATION: PCR primer

<400> SEQUENCE: 4
acaagaccgt ggagagaaag tgtgasgtgg agtgtccaar gtgtccagcc cctccagtgg    60

<210> SEQ ID NO 5
<211> LENGTH: 35
<212> TYPE: DNA
<213> ORGANISM: Artificial Sequence
<220> FEATURE:
<223> OTHER INFORMATION: PCR primer

<400> SEQUENCE: 5
atacaagcgg ccgcctattt acccggagac aggga                       35

<210> SEQ ID NO 6
<211> LENGTH: 60
<212> TYPE: DNA
<213> ORGANISM: Artificial Sequence
<220> FEATURE:
<223> OTHER INFORMATION: PCR primer

<400> SEQUENCE: 6
acaagaccgt ggagagaaag tgtgasgtgg agtgtccaga stgtccagcc cctccagtgg    60

<210> SEQ ID NO 7
<211> LENGTH: 60
<212> TYPE: DNA
<213> ORGANISM: Artificial Sequence
<220> FEATURE:
<223> OTHER INFORMATION: PCR primer

<400> SEQUENCE: 7
acaagaccgt ggagagaaag tgtgasgtga rgtgtccaga stgtccagcc cctccagtgg    60

<210> SEQ ID NO 8
<211> LENGTH: 60
<212> TYPE: DNA
<213> ORGANISM: Artificial Sequence
<220> FEATURE:
<223> OTHER INFORMATION: PCR primer

<400> SEQUENCE: 8
acaagaccgt ggagagaaag tgtarggtga rgtgtccaga stgtccagcc cctccagtgg    60

<210> SEQ ID NO 9
<211> LENGTH: 60
<212> TYPE: DNA
<213> ORGANISM: Artificial Sequence
<220> FEATURE:
<223> OTHER INFORMATION: PCR primer

<400> SEQUENCE: 9
acaagaccgt ggagagaaag tgtarggtga rgtgtccaar gtgtccagcc cctccagtgg    60

<210> SEQ ID NO 10
<211> LENGTH: 60
<212> TYPE: DNA
<213> ORGANISM: Artificial Sequence
<220> FEATURE:
<223> OTHER INFORMATION: PCR primer

<400> SEQUENCE: 10
acaagaccgt ggagagaaag tgtarggtgg agtgtccaar gtgtccagcc cctccagtgg    60

<210> SEQ ID NO 11
<211> LENGTH: 1000
<212> TYPE: DNA
<213> ORGANISM: Artificial Sequence
<220> FEATURE:
<223> OTHER INFORMATION: PCR primer

<400> SEQUENCE: 11
gcgtccacca agggcccatc ggtcttcccc ctggcaccct cctccaagag cacctctggg    60
ggcacagcgg ccctgggctg cctggtcaag gactacttcc ccgaaccggt gacggtgtcg   120
tggaactcag gcgccctgac cagcggcgtg cacaccttcc cggctgtcct acagtcctca   180
ggactctact ccctcagcag cgtggtgacc gtgccctcca gcagcttggg cacccagacc   240
tacatctgca acgtgaatca caagcccagc aacaccaagg tcgacaagaa agttgagccc   300
aaatcttgtg acaaaactca cacatgccca ccgtgcccag cacctgaact cctggggga   360
ccgtcagtct tcctcttccc cccaaaaccc aaggacaccc tcatgatctc ccggacccct   420
gaggtcacat gcgtggtggt ggacgtgagc cacgaagacc ctgaggtcag gttcaactgg   480
tacgtggacg gcgtggaggt gcataatgcc aagacaaagc cgcgggagga gcagtacaac   540
agcacgtacc gtgtggtcag cgtcctcacc gtcctgcacc aggactggct gaatggcaag   600
gagtacaagt gcaaggtctc caacaaagcc ctcccagccc ccatcgagaa aaccatctcc   660
aaagccaaag gcagccccg agaaccacag gtgtacaccc tgcccccatc ccgggatgag   720
ctgaccaaga accaggtcag cctgacctgc ctggtcaaag gcttctatcc cagcgacatc   780
gccgtggagt gggagagcaa tgggcagccg gagaacaact acaagaccac gcctcccgtg   840
ctggactccg acggctcctt cttcctctac agcaagctca ccgtggacaa gagcaggtgg   900
cagcagggga acgtcttctc atgctccgtg atgcatgagg ctctgcacaa ccactacacg   960
cagaagagcc tctccctgtc cccgggtaaa tagcggccgc                         1000

<210> SEQ ID NO 12
<211> LENGTH: 1000
<212> TYPE: DNA
<213> ORGANISM: Artificial Sequence
<220> FEATURE:
<223> OTHER INFORMATION: PCR primer

<400> SEQUENCE: 12
gcgtccacca agggcccatc ggtcttcccc ctggcaccct cctccaagag cacctctggg    60
ggcacagcgg ccctgggctg cctggtcaag gactacttcc ccgaaccggt gacggtgtcg   120
tggaactcag gcgccctgac cagcggcgtg cacaccttcc cggctgtcct acagtcctca   180
ggactctact ccctcagcag cgtggtgacc gtgccctcca gcagcttggg cacccagacc   240
tacatctgca acgtgaatca caagcccagc aacaccaagg tcgacaagaa agttgagccc   300
aaatcttgtg acaaaactca cacatgccca ccgtgcccag cacctgaact cctgggggga   360

```
ccgtcagtct tcctcttccc cccaaaaccc aaggacaccc tcatgatctc ccggacccct      420
gaggtcacat gcgtggtggt ggacgtgagc cacgaagacc ctgaggtcag gttcaactgg      480
tacgtggacg gcgtggaggt gcataatgcc aagacaaagc cgcggggagga gcagtacaac    540 agcacgtacc gtgtggtcag cgtcctcacc gtcctgcacc aggactggct gaatggcaag     600
gagtacaagt gcaaggtctc caacaaagcc ctcccagccc ccatcgagaa aaccatctcc     660
aaagccaaag gcagccccg agaaccacag gtgtacaccc tgcccccatc ccgggatgag      720
ctgaccaaga accaggtcag cctgacctgc ctggtcaaag gcttctatcc cagcgacatc    780
gccgtggagt gggagagcaa tgggcagccg gagaacaact acaagaccac gcctcccgtg     840
ctggactccg acggctcctt cttcctctac agcaagctca ccgtggacaa gagcaggtgg    900
cagcagggga acgtcttctc atgctccgtg atgcatgagg ctctgcacaa ccactacacg     960
cagaagagcc tctccctgtc cccgggtaaa tagcggccgc                          1000
```

```
<210> SEQ ID NO 13
<211> LENGTH: 20
<212> TYPE: DNA
<213> ORGANISM: Artificial Sequence
<220> FEATURE:
<223> OTHER INFORMATION: PCR primer

<400> SEQUENCE: 13
gcctccacca agggcccatc                                                  20

<210> SEQ ID NO 14
<211> LENGTH: 37
<212> TYPE: DNA
<213> ORGANISM: Artificial Sequence
<220> FEATURE:
<223> OTHER INFORMATION: PCR primer

<400> SEQUENCE: 14
atacaagcgg ccgcctattt acccagagac agggaga                               37

<210> SEQ ID NO 15
<211> LENGTH: 50
<212> TYPE: DNA
<213> ORGANISM: Artificial Sequence
<220> FEATURE:
<223> OTHER INFORMATION: PCR primer

<400> SEQUENCE: 15
gagtccaaat atggtccccc atgcccaarg tgcccagcac ctgagttcct                 50

<210> SEQ ID NO 16
<211> LENGTH: 50
<212> TYPE: DNA
<213> ORGANISM: Artificial Sequence
<220> FEATURE:
<223> OTHER INFORMATION: PCR primer

<400> SEQUENCE: 16
gagtccaaat atggtccccc atgcccagas tgcccagcac ctgagttcct                 50

<210> SEQ ID NO 17
<211> LENGTH: 20
<212> TYPE: DNA
<213> ORGANISM: Artificial Sequence
<220> FEATURE:
<223> OTHER INFORMATION: PCR primer
```

<400> SEQUENCE: 17
tgggggacca tatttggact                                            20

<210> SEQ ID NO 18
<211> LENGTH: 20
<212> TYPE: DNA
<213> ORGANISM: Artificial Sequence
<220> FEATURE:
<223> OTHER INFORMATION: PCR primer

<400> SEQUENCE: 18
gcctccacca agggcccatc                                            20

<210> SEQ ID NO 19
<211> LENGTH: 35
<212> TYPE: DNA
<213> ORGANISM: Artificial Sequence
<220> FEATURE:
<223> OTHER INFORMATION: PCR primer

<400> SEQUENCE: 19
atacaagcgg ccgcctattt acccggagac aggga                           35

<210> SEQ ID NO 20
<211> LENGTH: 65
<212> TYPE: DNA
<213> ORGANISM: Artificial Sequence
<220> FEATURE:
<223> OTHER INFORMATION: PCR primer

<400> SEQUENCE: 20
gaaagttgag cccaaatctt gtgagaaaac tcacacatgc ccagagtgcc cagcacctga    60
actcc                                                            65

<210> SEQ ID NO 21
<211> LENGTH: 65
<212> TYPE: DNA
<213> ORGANISM: Artificial Sequence
<220> FEATURE:
<223> OTHER INFORMATION: PCR primer

<400> SEQUENCE: 21
gaaagttgag cccaaatctt gtaggaaaac tcacacatgc ccaaggtgcc cagcacctga    60
actcc                                                            65

<210> SEQ ID NO 22
<211> LENGTH: 22
<212> TYPE: DNA
<213> ORGANISM: Artificial Sequence
<220> FEATURE:
<223> OTHER INFORMATION: PCR primer

<400> SEQUENCE: 22
acaagatttg ggctcaactt tc                                         22

<210> SEQ ID NO 23
<211> LENGTH: 27
<212> TYPE: DNA
<213> ORGANISM: Artificial Sequence
<220> FEATURE:
<223> OTHER INFORMATION: PCR primer

<400> SEQUENCE: 23
ccccgagaac cagaggtgta caccctg                                    27

```
<210> SEQ ID NO 24
<211> LENGTH: 27
<212> TYPE: DNA
<213> ORGANISM: Artificial Sequence
<220> FEATURE:
<223> OTHER INFORMATION: PCR primer

<400> SEQUENCE: 24
cagggtgtac acctctggtt ctcgggg                                    27

<210> SEQ ID NO 25
<211> LENGTH: 30
<212> TYPE: DNA
<213> ORGANISM: Artificial Sequence
<220> FEATURE:
<223> OTHER INFORMATION: PCR primer

<400> SEQUENCE: 25
gagaaccaca ggtggagacc ctgcccccat                                 30

<210> SEQ ID NO 26
<211> LENGTH: 30
<212> TYPE: DNA
<213> ORGANISM: Artificial Sequence
<220> FEATURE:
<223> OTHER INFORMATION: PCR primer

<400> SEQUENCE: 26
atgggggcag ggtctccacc tgtggttctc                                 30

<210> SEQ ID NO 27
<211> LENGTH: 30
<212> TYPE: DNA
<213> ORGANISM: Artificial Sequence
<220> FEATURE:
<223> OTHER INFORMATION: PCR primer

<400> SEQUENCE: 27
aaccacaggt gtacgagctg cccccatccc                                 30

<210> SEQ ID NO 28
<211> LENGTH: 30
<212> TYPE: DNA
<213> ORGANISM: Artificial Sequence
<220> FEATURE:
<223> OTHER INFORMATION: PCR primer

<400> SEQUENCE: 28
gggatggggg cagctcgtac acctgtggtt                                 30

<210> SEQ ID NO 29
<211> LENGTH: 30
<212> TYPE: DNA
<213> ORGANISM: Artificial Sequence
<220> FEATURE:
<223> OTHER INFORMATION: PCR primer

<400> SEQUENCE: 29
cacaggtgta caccgagccc ccatcccggg                                 30

<210> SEQ ID NO 30
<211> LENGTH: 30
<212> TYPE: DNA
<213> ORGANISM: Artificial Sequence
<220> FEATURE:
```

```
<223> OTHER INFORMATION: PCR primer

<400> SEQUENCE: 30
cccgggatgg gggctcggtg tacacctgtg                                    30

<210> SEQ ID NO 31
<211> LENGTH: 30
<212> TYPE: DNA
<213> ORGANISM: Artificial Sequence
<220> FEATURE:
<223> OTHER INFORMATION: PCR primer

<400> SEQUENCE: 31
ccaggtcagc ctggagtgcc tggtcaaagg                                    30

<210> SEQ ID NO 32
<211> LENGTH: 30
<212> TYPE: DNA
<213> ORGANISM: Artificial Sequence
<220> FEATURE:
<223> OTHER INFORMATION: PCR primer

<400> SEQUENCE: 32
cctttgacca ggcactccag gctgacctgg                                    30

<210> SEQ ID NO 33
<211> LENGTH: 30
<212> TYPE: DNA
<213> ORGANISM: Artificial Sequence
<220> FEATURE:
<223> OTHER INFORMATION: PCR primer

<400> SEQUENCE: 33
cagcctgacc tgcgaggtca aaggcttcta                                    30

<210> SEQ ID NO 34
<211> LENGTH: 30
<212> TYPE: DNA
<213> ORGANISM: Artificial Sequence
<220> FEATURE:
<223> OTHER INFORMATION: PCR primer

<400> SEQUENCE: 34
tagaagcctt tgacctcgca ggtcaggctg                                    30

<210> SEQ ID NO 35
<211> LENGTH: 30
<212> TYPE: DNA
<213> ORGANISM: Artificial Sequence
<220> FEATURE:
<223> OTHER INFORMATION: PCR primer

<400> SEQUENCE: 35
tgacctgcct ggtcgagggc ttctatccca                                    30

<210> SEQ ID NO 36
<211> LENGTH: 30
<212> TYPE: DNA
<213> ORGANISM: Artificial Sequence
<220> FEATURE:
<223> OTHER INFORMATION: PCR primer

<400> SEQUENCE: 36
tgggatagaa gccctcgacc aggcaggtca                                    30
```

```
<210> SEQ ID NO 37
<211> LENGTH: 30
<212> TYPE: DNA
<213> ORGANISM: Artificial Sequence
<220> FEATURE:
<223> OTHER INFORMATION: PCR primer

<400> SEQUENCE: 37
ggagaacaac tacgagacca cgcctcccgt                                30

<210> SEQ ID NO 38
<211> LENGTH: 30
<212> TYPE: DNA
<213> ORGANISM: Artificial Sequence
<220> FEATURE:
<223> OTHER INFORMATION: PCR primer

<400> SEQUENCE: 38
acgggaggcg tggtctcgta gttgttctcc                                30

<210> SEQ ID NO 39
<211> LENGTH: 30
<212> TYPE: DNA
<213> ORGANISM: Artificial Sequence
<220> FEATURE:
<223> OTHER INFORMATION: PCR primer

<400> SEQUENCE: 39
caactacaag accgagcctc ccgtgctgga                                30

<210> SEQ ID NO 40
<211> LENGTH: 30
<212> TYPE: DNA
<213> ORGANISM: Artificial Sequence
<220> FEATURE:
<223> OTHER INFORMATION: PCR primer

<400> SEQUENCE: 40
tccagcacgg gaggctcggt cttgtagttg                                30

<210> SEQ ID NO 41
<211> LENGTH: 30
<212> TYPE: DNA
<213> ORGANISM: Artificial Sequence
<220> FEATURE:
<223> OTHER INFORMATION: PCR primer

<400> SEQUENCE: 41
gaccacgcct cccgagctgg actccgacgg                                30

<210> SEQ ID NO 42
<211> LENGTH: 30
<212> TYPE: DNA
<213> ORGANISM: Artificial Sequence
<220> FEATURE:
<223> OTHER INFORMATION: PCR primer

<400> SEQUENCE: 42
ccgtcggagt ccagctcggg aggcgtggtc                                30

<210> SEQ ID NO 43
<211> LENGTH: 30
<212> TYPE: DNA
<213> ORGANISM: Artificial Sequence
<220> FEATURE:
<223> OTHER INFORMATION: PCR primer
```

```
<400> SEQUENCE: 43
acgcctcccg tggaggactc cgacggctcc                                    30

<210> SEQ ID NO 44
<211> LENGTH: 30
<212> TYPE: DNA
<213> ORGANISM: Artificial Sequence
<220> FEATURE:
<223> OTHER INFORMATION: PCR primer

<400> SEQUENCE: 44
ggagccgtcg gagtcctcca cgggaggcgt                                    30

<210> SEQ ID NO 45
<211> LENGTH: 30
<212> TYPE: DNA
<213> ORGANISM: Artificial Sequence
<220> FEATURE:
<223> OTHER INFORMATION: PCR primer

<400> SEQUENCE: 45
gacggctcct tcgagctgta cagcaagctc                                    30

<210> SEQ ID NO 46
<211> LENGTH: 30
<212> TYPE: DNA
<213> ORGANISM: Artificial Sequence
<220> FEATURE:
<223> OTHER INFORMATION: PCR primer

<400> SEQUENCE: 46
gagcttgctg tacagctcga aggagccgtc                                    30

<210> SEQ ID NO 47
<211> LENGTH: 29
<212> TYPE: DNA
<213> ORGANISM: Artificial Sequence
<220> FEATURE:
<223> OTHER INFORMATION: PCR primer

<400> SEQUENCE: 47
ctccttcttc ctcgagagca agctcaccg                                     29

<210> SEQ ID NO 48
<211> LENGTH: 29
<212> TYPE: DNA
<213> ORGANISM: Artificial Sequence
<220> FEATURE:
<223> OTHER INFORMATION: PCR primer

<400> SEQUENCE: 48
cggtgagctt gctctcgagg aagaaggag                                     29

<210> SEQ ID NO 49
<211> LENGTH: 31
<212> TYPE: DNA
<213> ORGANISM: Artificial Sequence
<220> FEATURE:
<223> OTHER INFORMATION: PCR primer

<400> SEQUENCE: 49
ttcctctaca gcgagctgac cgtggacaag a                                  31

<210> SEQ ID NO 50
<211> LENGTH: 31
```

```
<212> TYPE: DNA
<213> ORGANISM: Artificial Sequence
<220> FEATURE:
<223> OTHER INFORMATION: PCR primer

<400> SEQUENCE: 50
tcttgtccac ggtcagctcg ctgtagagga a                              31

<210> SEQ ID NO 51
<211> LENGTH: 31
<212> TYPE: DNA
<213> ORGANISM: Artificial Sequence
<220> FEATURE:
<223> OTHER INFORMATION: PCR primer

<400> SEQUENCE: 51
ttcctctaca gcaggctgac cgtggacaag a                              31

<210> SEQ ID NO 52
<211> LENGTH: 31
<212> TYPE: DNA
<213> ORGANISM: Artificial Sequence
<220> FEATURE:
<223> OTHER INFORMATION: PCR primer

<400> SEQUENCE: 52
tcttgtccac ggtcagcctg ctgtagagga a                              31

<210> SEQ ID NO 53
<211> LENGTH: 25
<212> TYPE: PRT
<213> ORGANISM: Artificial Sequence
<220> FEATURE:
<223> OTHER INFORMATION: N-terminus 3xFLAG tag

<400> SEQUENCE: 53

Asp Tyr Lys Asp His Asp Gly Asp Tyr Lys Asp His Asp Ile Asp Tyr
1               5                   10                  15

Lys Asp Asp Asp Asp Lys Gly Leu Glu
            20                  25

<210> SEQ ID NO 54
<211> LENGTH: 11
<212> TYPE: PRT
<213> ORGANISM: Artificial Sequence
<220> FEATURE:
<223> OTHER INFORMATION: N-terminus HA tag

<400> SEQUENCE: 54

Tyr Pro Tyr Asp Val Pro Asp Tyr Ala Leu Glu
1               5                   10

<210> SEQ ID NO 55
<211> LENGTH: 12
<212> TYPE: PRT
<213> ORGANISM: Homo sapiens

<400> SEQUENCE: 55

Glu Ser Lys Tyr Gly Pro Pro Cys Pro Ser Cys Pro
1               5                   10

<210> SEQ ID NO 56
<211> LENGTH: 12
<212> TYPE: PRT
<213> ORGANISM: Homo sapiens
```

<400> SEQUENCE: 56

Glu Arg Lys Cys Cys Val Glu Cys Pro Pro Cys Pro
1               5                   10

<210> SEQ ID NO 57
<211> LENGTH: 15
<212> TYPE: PRT
<213> ORGANISM: Homo sapiens

<400> SEQUENCE: 57

Glu Pro Lys Ser Cys Asp Lys Thr His Thr Cys Pro Pro Cys Pro
1               5                   10                  15

<210> SEQ ID NO 58
<211> LENGTH: 107
<212> TYPE: PRT
<213> ORGANISM: Homo sapiens

<400> SEQUENCE: 58

Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 59
<211> LENGTH: 107
<212> TYPE: PRT
<213> ORGANISM: Homo sapiens

<400> SEQUENCE: 59

Gly Gln Pro Arg Glu Pro Gln Val Tyr Thr Leu Pro Pro Ser Arg Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Met Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 60
<211> LENGTH: 107
<212> TYPE: PRT
<213> ORGANISM: Homo sapiens

```
<400> SEQUENCE: 60

Gly Gln Pro Arg Glu Pro Gln Val Tyr Thr Leu Pro Pro Ser Gln Glu
1               5                   10                  15

Glu Met Thr Lys Asn Gln Val Ser Leu Thr Cys Leu Val Lys Gly Phe
                20                  25                  30

Tyr Pro Ser Asp Ile Ala Val Glu Trp Glu Ser Asn Gly Gln Pro Glu
            35                  40                  45

Asn Asn Tyr Lys Thr Thr Pro Pro Val Leu Asp Ser Asp Gly Ser Phe
        50                  55                  60

Phe Leu Tyr Ser Arg Leu Thr Val Asp Lys Ser Arg Trp Gln Glu Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Leu Gly Lys
                100             105
```